United States Patent [19]

Rosenbush et al.

[11] Patent Number: 4,607,337

[45] Date of Patent: Aug. 19, 1986

[54] INTERPROBE ELECTROSTATIC ENGINE DIAGNOSTICS CORRELATION

[75] Inventors: David M. Rosenbush, Granby; Philip E. Zwicke, South Glastonbury, both of Conn.; Robert P. Couch, Palm Beach Gardens, Fla.

[73] Assignee: United Technologies Corporation, Hartford, Conn.

[21] Appl. No.: 453,964

[22] Filed: Dec. 28, 1982

[51] Int. Cl.[4] .......................................... G01M 15/00
[52] U.S. Cl. ................... 364/431.02; 364/551; 73/116
[58] Field of Search ............... 364/431.01–431.02, 364/424, 487, 507–508, 550, 551; 324/80, 464; 73/35, 116, 660

[56] References Cited

U.S. PATENT DOCUMENTS

| | | | |
|---|---|---|---|
| 4,027,532 | 6/1977 | Trussell et al. | 364/431.01 |
| 4,135,246 | 1/1979 | McMannis | 73/116 |
| 4,179,922 | 12/1979 | Bouvenie et al. | 73/116 |
| 4,215,412 | 7/1980 | Bernier et al. | 73/116 |
| 4,249,238 | 2/1981 | Spang, III et al. | 364/431.02 |
| 4,394,742 | 7/1983 | Crummer et al. | 364/487 |
| 4,418,388 | 10/1983 | Allgor et al. | 364/431.01 |
| 4,456,883 | 6/1984 | Bullis et al. | 73/116 |

*Primary Examiner*—Gary Chin
*Assistant Examiner*—Thomas G. Black
*Attorney, Agent, or Firm*—M. P. Williams

[57] ABSTRACT

The quality factors (Q) indicative of the likelihood of the waveshape (FIGS. 57–80) of signals produced by electrostatic probes (1, 2, 3, FIG. 1) disposed in the gas stream of a gas turbine engine are combined for certain categories of sets of the probes which will simultaneously sense the same engine event (FIGS. 9, 12a, 12b). The likelihood of signals correlating to particular engine event as a function of positive and negative threshold crossings (FIG. 83) is correlated as between pairs of probes, both digitally (FIGS. 85 and 86) and by analog hardware (FIGS. 87 and 88).

3 Claims, 99 Drawing Figures

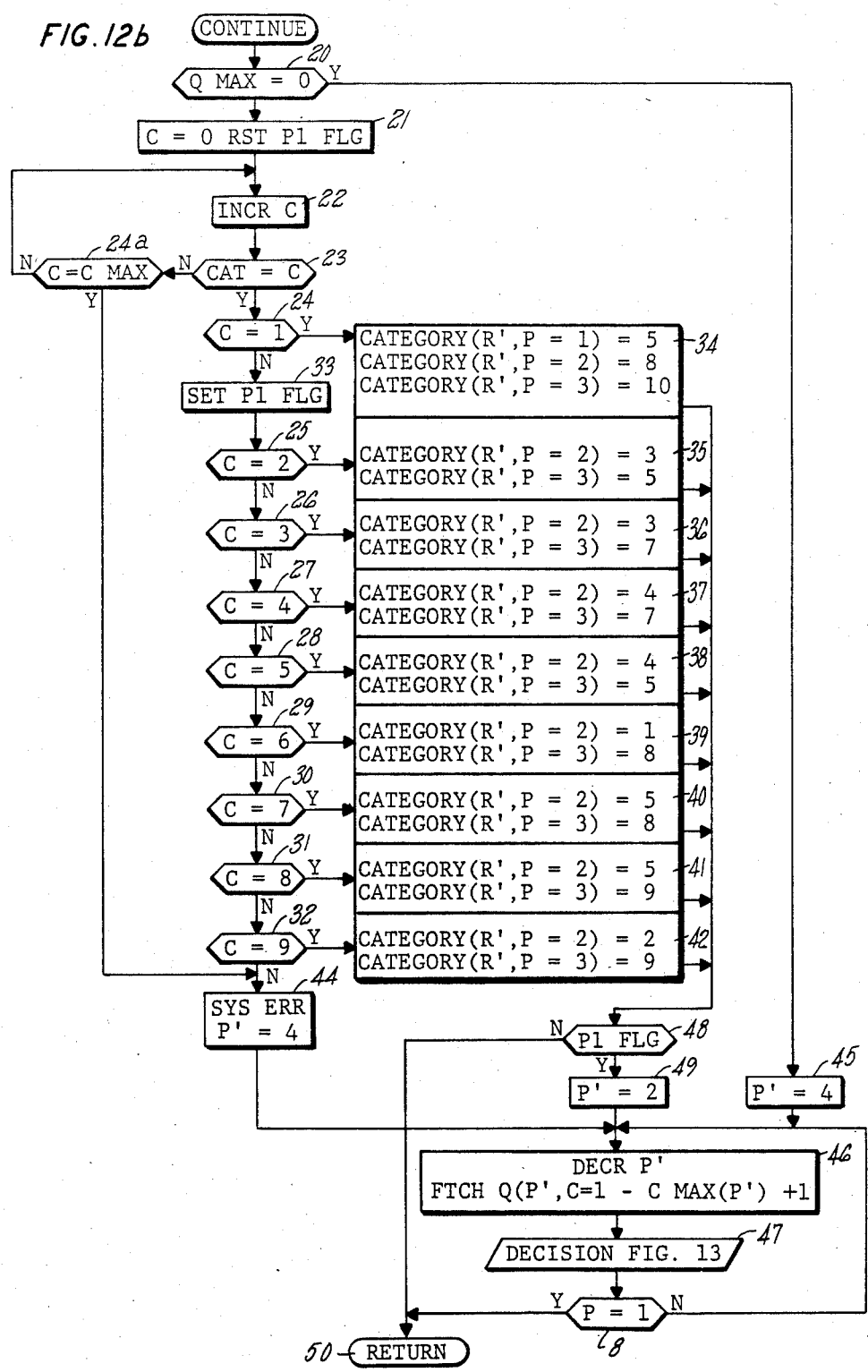

SEPRATN ≤ OPOS SEP LO LIM

SEPRATN > OPOS SEP LO LIM

SEPRATN < SAME SEP LO LIM

SEPRATN > SEPRATN HI LIM

DEGRADE

WIDTH > FOLWNG PULS WIDTH LIM

PRE R.M.S. TOO HIGH

PRE R.M.S. AND POST R.M.S. TOO HIGH

FIG. 35
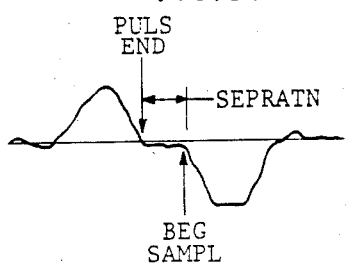
FIG. 36
FIG. 37
FIG. 38
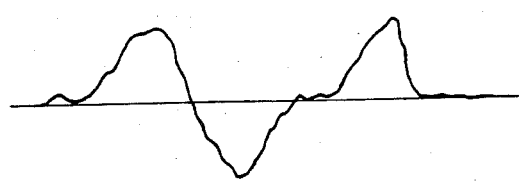
FIG. 39
FIG. 40
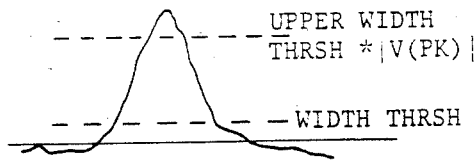
FIG. 41
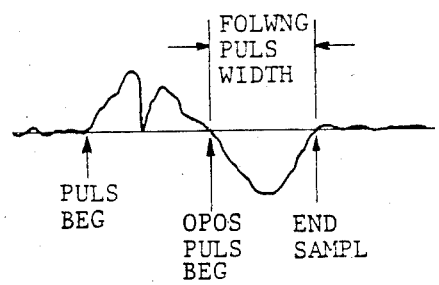
FIG. 42
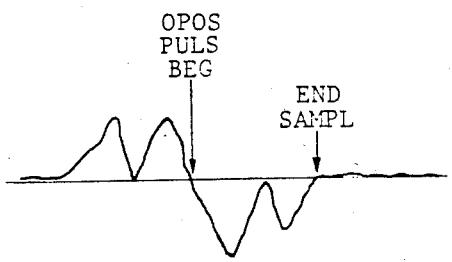

FIG. 54c

```
          (CONTINUE)
               │
               ▼
┌──────────────────────────────────────────┐ ─37
│ HI NOISE LIM = HI NOISE LIM * [HI NOISE INTVL / MAX SAMPL]       │
│                                                                   │
│ HI NOISE NOMNL = HI NOISE NOMNL* [HI NOISE INTVL / MAX SAMPL]    │
│                                                                   │
│ LO NOISE LIM = LO NOISE LIM* [LO NOISE INTVL / MAX SAMPL]        │
│                                                                   │
│ LO NOISE NOMNL = LO NOISE NOMNL* [LO NOISE INTVL / MAX SAMPL]    │
└──────────────────────────────────────────┘
               │
               ▼                           ─38
       ◁ HI NOISE ZERO CROSNGS < HI NOISE LIM ▷──Y──┐
               │N                                    │
               ▼                           ─40       │
┌─────────────────────────────────┐                  │
│ MEASRD = HI NOISE ZERO CROSNGS  │                  │
│ NOMNL = HI NOISE NOMNL          │                  │
│ DGRDN = ZERO CROS EXP           │                  │
│ SENSTVTY = ZERO CROS DVSR       │                  │
└─────────────────────────────────┘                  │
               │                                      │
               ▼                           ─41        │
        / DEGRADE FIG.24 /                            │
               │                                      │
               ▼                           ─42        │
       ◁ LO NOISE ZERO CROSNGS > LO NOISE LIM ▷──Y──┤
               │N                                    │
               │                                   ─39│
               │                                  (RETURN)
               ▼                           ─44
┌─────────────────────────────────┐
│ MEASRD = LO NOISE ZERO CROSNGS  │
│ NOMNL = LO NOISE NOMNL          │
│ DGRDN = ZERO CROS EXP           │
│ SENSTVTY = ZERO CROS DVSR       │
└─────────────────────────────────┘
               │
               ▼                           ─45
        / DEGRADE FIG.24 /
               │
               ▼                           ─46
     ┌────────────────────────────┐
     │ Q = 1.0 (DEGRADE/DEGRADE MAX) │
     └────────────────────────────┘
               │
               ▼          ─47
         Y ◁ Q < 0 ▷
         │    N │
         ▼─48   ▼─49
      [Q(C)=0] [Q(C)=Q]
         │      │
         └──┬───┘
            ▼  ─50
         (RETURN)
```

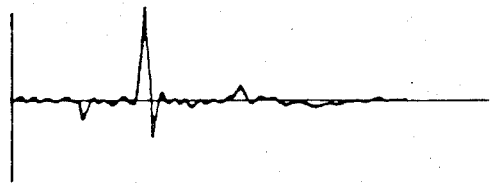
FIG. 57  PROB 1, CAT. 1
CMPRSR
METL/ABRAD. RUB
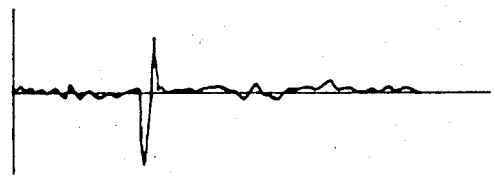
FIG. 58  PROB 1, CAT. 2
CMPRSR
METL/METL RUB
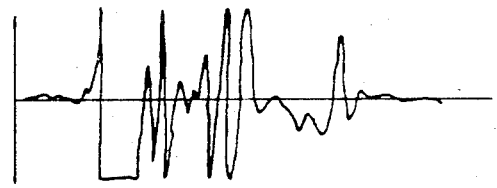
FIG. 59  PROB 1, CAT. 3
SURGE
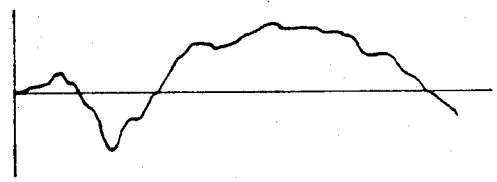
FIG. 60  PROB 1, CAT. 4
PROB 2, CAT. 6
LOOSE PROB
ELECTRODE
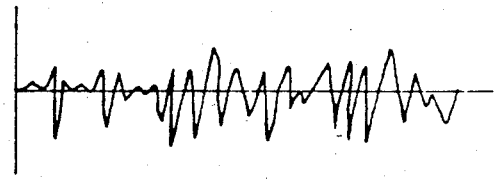
FIG. 61  PROB 1, CAT. 5
PROB 2, CAT. 7
LOOSE PROB
FIG. 62  PROB 1, CAT. 6
PROB 2, CAT. 8
PROB 3, CAT. 10
RUB STRIP
(ABRAD. SEAL)

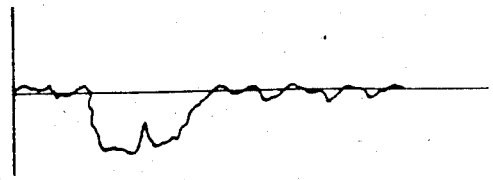
FIG. 63　PROB 2, CAT. 1
1ST HI TURB BLADE EROSN
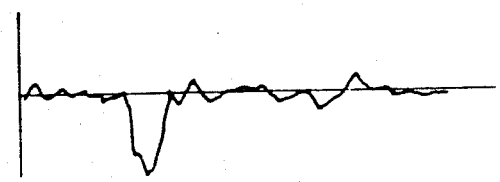
FIG. 64　PROB 2, CAT. 2
1ST HI TURB VANE EROSN
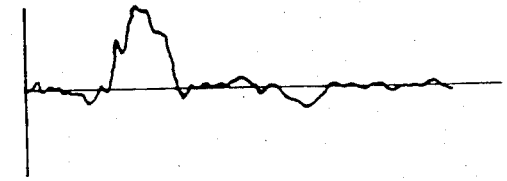
FIG. 65　PROB 2, CAT. 3
1ST HI TURB RUB
FIG. 66　PROB 2, CAT. 4
2ND HI TURB RUB
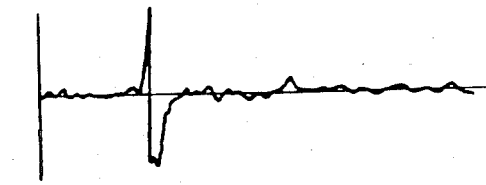
FIG. 67　PROB 2, CAT. 5
2ND HI TURB BLADE OR VANE EROSN

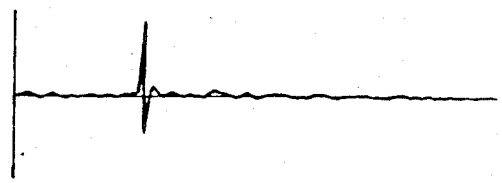
FIG. 68  PROB 3, CAT. 1  FLAMING DEBRIS
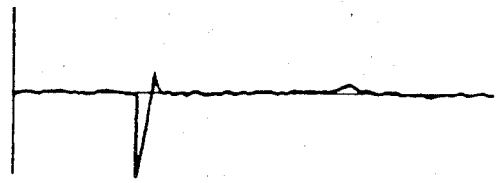
FIG. 69  PROB 3, CAT. 2  A/B NOZL LINER EROSN
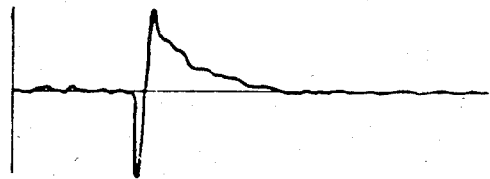
FIG. 70  PROB 3, CAT. 3  UNCORRELATED-1
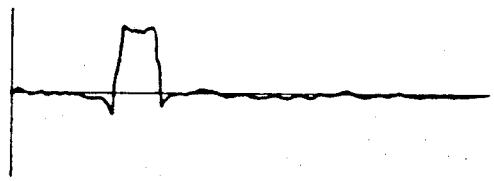
FIG. 71  PROB 3, CAT. 4  UNCORRELATED-2
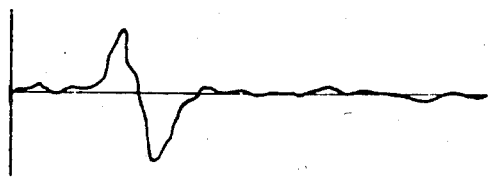
FIG. 72  PROB 3, CAT. 5  HI TURB RUB
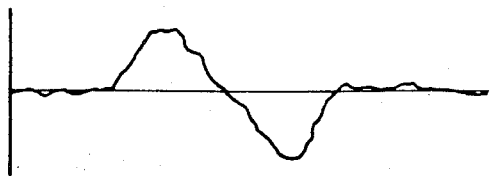
FIG. 73  PROB 3, CAT. 6  LO TURB RUB
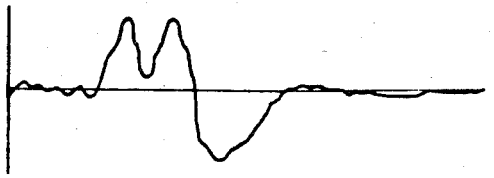
FIG. 74  PROB 3, CAT. 7  HI OR LO TURB IMPACT-INDUCED RUB FIG. 75  PROB 3, CAT. 8
HI TURB BLADE
EROSN
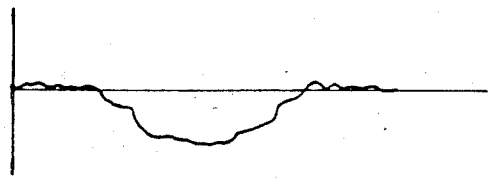
FIG. 76  PROB 3, CAT. 9
HI TURB VANE
EROSN
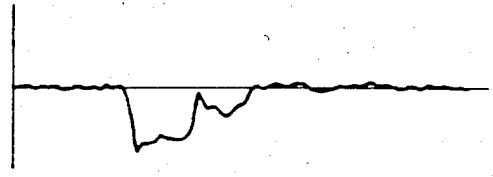
FIG. 77  PROB 3, CAT. 11
START OF
ABNORMAL
A/B CHOP
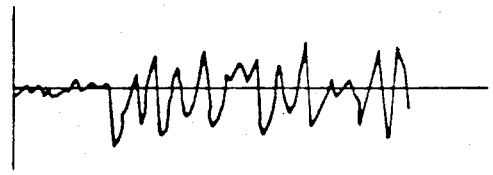
FIG. 78  PROB 3, CAT. 12
END OF
ABNORMAL
A/B CHOP
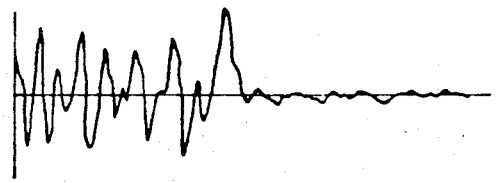
FIG. 79  PROB 3, CAT. 13
NORMAL
A/B CHOP
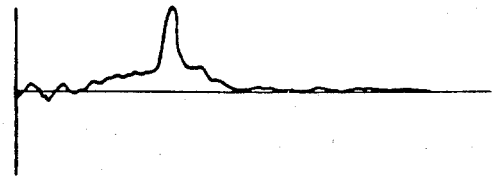
FIG. 80  PROB 3, CAT. 14
ACEL/DECEL
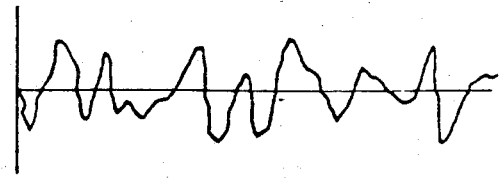

INTERPROBE ELECTROSTATIC ENGINE DIAGNOSTICS CORRELATIONCL TECHNICAL FIELD

This invention relates to monitoring of gas turbine engines by discrimination of waveshapes of corresponding electrostatic signals produced on a plurality of probes disposed in the gas path of such engines, and more particularly to discrimination of waveshapes by correlation between probes.

BACKGROUND ART

There are a variety of methods known for generally determining the health of gas turbine engines, particularly aircraft engines. General engine condition, as well as an indication of engine life expectancy and need for overhaul, is provided by trending systems which utilize engine parameters such as various temperatures, pressures and control parameters associated therewith to determine current engine operating condition and impute engine health. However, such systems do not recognize isolated events within the engine which can be indicative of severe engine distress or impending engine component failure from a particular causal event.

Certain engine conditions can be determined visually, such as through borescopes, without tearing down the engine. As examples, severe blade erosion (high temperature corrosion), loss of abradable seal segments, or excessive rubbing can frequently be detected by borescope inspection methods. Additonally, periodic teardown of an engine allows inspection of far more components, much more reliably. Because engine teardown is such a complex and expensive proposition, various schemes are employed to determine when engine teardown should be performed. Tearing engines down too frequently is, of course, an extreme waste of time and money. Failure to tear down an engine when it may have problems could result in engines malfunctioning while in use. Because of the complexity and expense involved, any improvement in diagnostic methodology is of great value.

In the past decade, monitoring of the electrical characteristics of gas flowing through a jet engine has been studied as a possible indication of engine deterioration. Apparatus disclosed in U.S. Pat. No. 3,775,763 utilizes an electrostatic probe positioned in the exhaust of the jet engine, such as through the tail pipe wall. Abnormal conditions were thought to be coupled with small particles striking the probe and causing spikes of ion current of a relatively large magnitude. Subsequently, as reported by Couch, R.P.: "Detecting Abnormal Turbine Engine Deterioration Using Electrostatic Methods", *Journal of Aircraft*, Vol. 15, October 1978, pp 692-695, it was theorized that the signals did not result from individual particles of metal hitting the probe, but rather that the signals were indicative of Trichel pulses (a form of repetitive corona discharge) created by high potential pockets of excess charge. A probe set including circular insulated segments within the gas turbine engine tail pipe and a triangle of wire extending through the tail pipe exhaust gas path were developed. With these probes, a normalized count of large signals (probe current, or voltage developed across an impedance, in excess of a threshold magnitude) over a period of time definitely correlated with impending engine component malfunctions or severe deterioration. As reported in the aforementioned article, however, the use of normalized counts of large magnitude signals from the ring and grid probe was thought to provide reliable prediction of only two out of three gas-path failures, at best, and distinction between possible causes thereof was highly experimental, as described below.

In a commonly owned, copending U.S. patent application entitled "Waveform Discriminated, Electrostatic Engine Diagnostics", Ser. No. 454,124, filed contemporaneously herewith by Zwicke et al, characteristics of the waveshape of signals developed on an electrostatic probe disposed for response to electrostatic charge in the gas stream of a gas turbine engine are utilized to discriminate waveshapes correlated to particular engine events or conditions, or classes thereof, from other waveshapes not having those characteristics or having other characteristics, which are thereby identified as different, whether correlated with other events and conditions or not.

In the waveshape-discriminated diagnostic system disclosed in the aforementioned application, it is shown that a number of electrostatic events in the gas stream of a gas turbine engine which are indicative of abnormal engine component wear cause electrostatic signals on more than one probe. It is also shown that there is a great deal of similarity between some signals on one probe that relate to particular engine events and other signals on the same probe that relate to different engine events. Naturally, the degree to which accurate waveform discrimination of electrostatic signals for correlation to particular engine events can be successful is dependent upon the degree to which similar pulses on the same probe can be discriminated.

DISCLOSURE OF INVENTION

Objects of the invention include improvements in discrimination of waveshapes related to causal electrostatic activity in the gas stream of a gas turbine engine; improvement of certainty as to the event which caused electrostatic signals on probes disposed on the gas stream of a gas turbine engine; and provision of simple, relatively low cost electrostatic gas turbine engine diagnostics.

According to the present invention, a plurality of electrostatic probes are disposed at different points along the gas stream of a gas turbine engine, the signals thereon resulting from electrostatic activity within the engine, some of which correlates directly to abnormal wear of engine components, is discriminated by correlating the signal produced by one probe with that produced by another probe displaced therefrom along the gas stream, with respect to engine events which provide classifiable electrostatic signals on a plurality of probes.

The present invention is particularly well suited to detecting and/or discriminating signals relating to turbine blade or vane erosion (high temperature corrosion), blade rubbing, and other engine events which are clearly detectable at various stations along the gas path of the gas engine, such as an abradable seal (rub strip) which has peeled off from the compressor.

In one embodiment of the invention, the waveform discrimination apparatus of the aforementioned application is modified to provide combination of quality factor values (indicative of the likelihood of a particular signal relating to a particular engine event), of a plurality of probes, before a decision as to the causal event is made. In other embodiments of the invention, waveshapes are not utilized, simply the occurrence and polarity of threshold crossings on a plurality of probes is utilized to determine the likelihood of the causal event. In one of the simpler forms, digital processing of a simple variety is employed. In another of these forms, simple analog signal processing is employed. The invention provides additional correlation/discrimination which is helpful in classifying the electrostatic signals in terms of likely causal event.

The present invention is disclosed herein as implemented by means of suitable programming of a microprocessor (or other programmable, digital signal processing system). The invention utilizes characteristics of waveshapes to discriminate signals which correlate to unique causal events or conditions, as in our aforementioned application. Although the signals which appear on any given probe have different waveshapes in dependence upon the characteristics of the probe and the particular orientation with respect to the gas stream of the jet engine, the wide variety of different signal types which are distinguished by characteristics thereof herein is indicative of the wide use to which the present invention may be made, in addition to that disclosed particularly herein as an exemplar.

The foregoing, and various other objects, features and advantages of the present invention will become more apparent in the light of the detailed description of exemplary embodiments thereof, as illustrated in the accompanying drawings.

Figure 3:
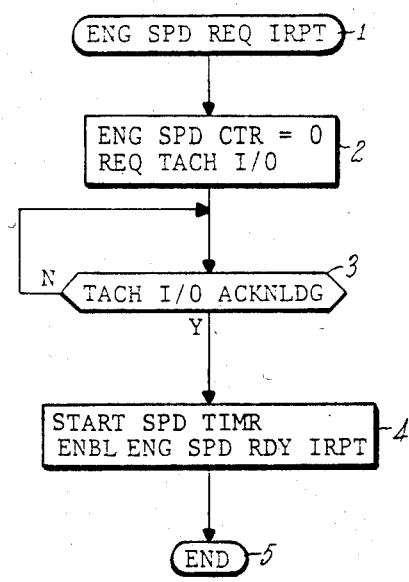
Figure 4:
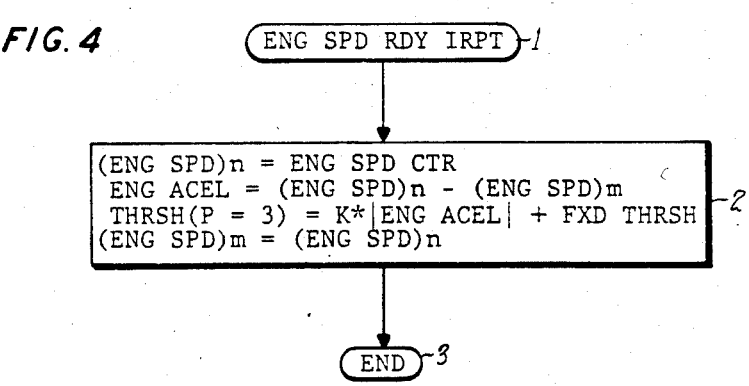
Figure 5:
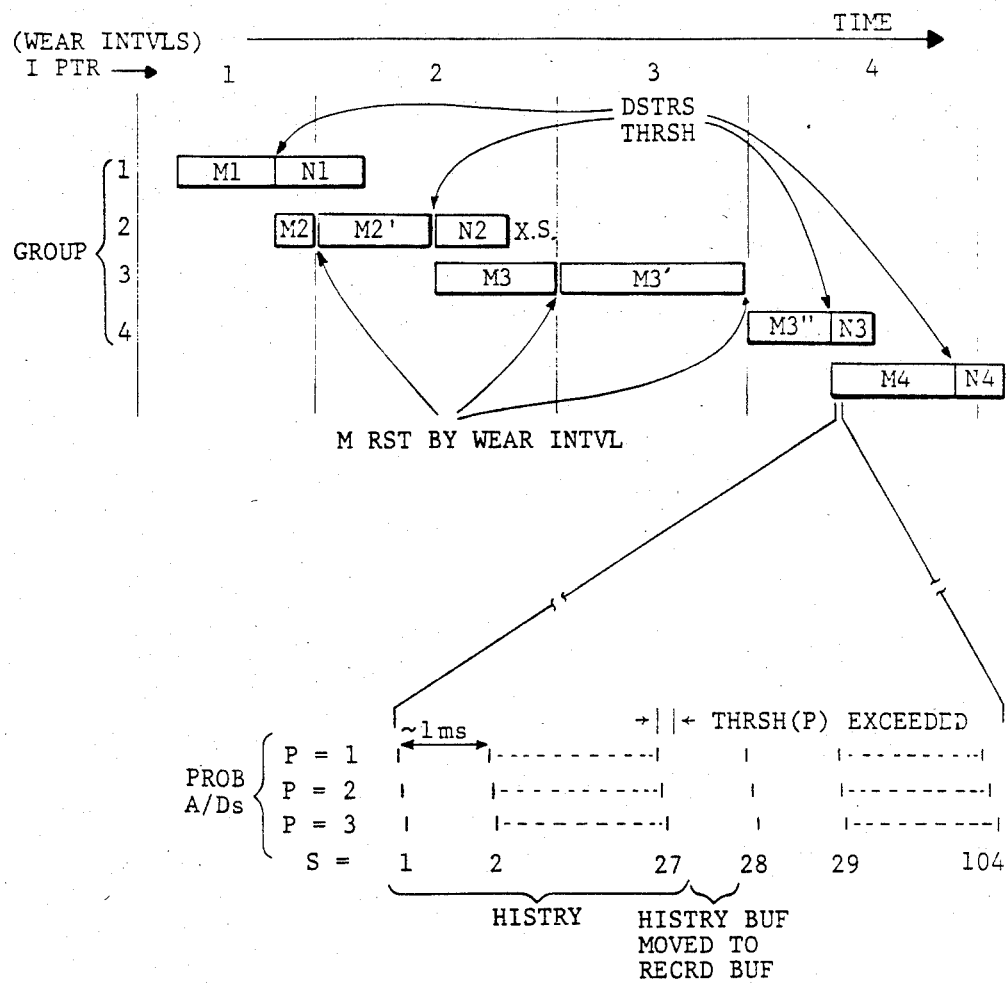
Figure 6:
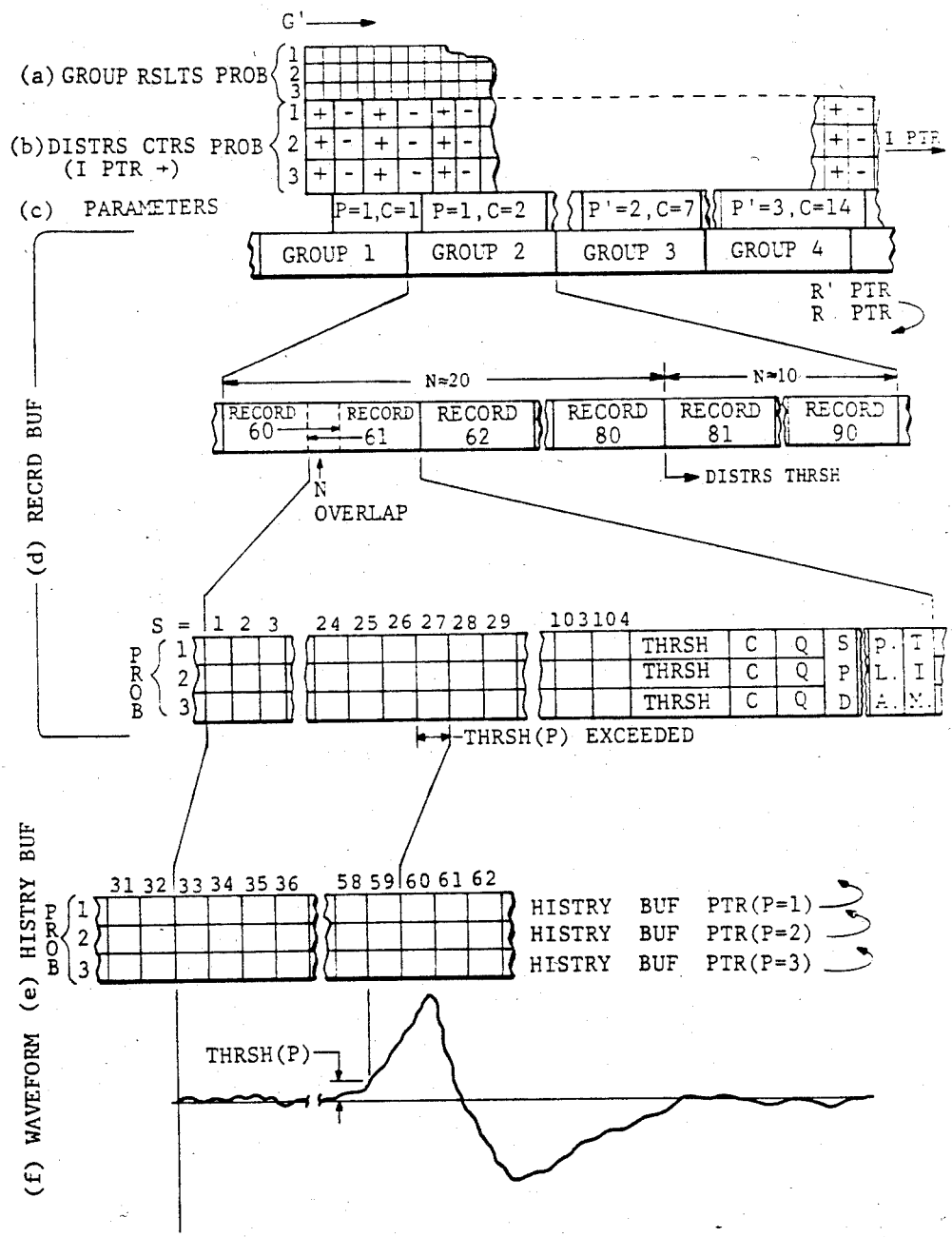
Figure 7:
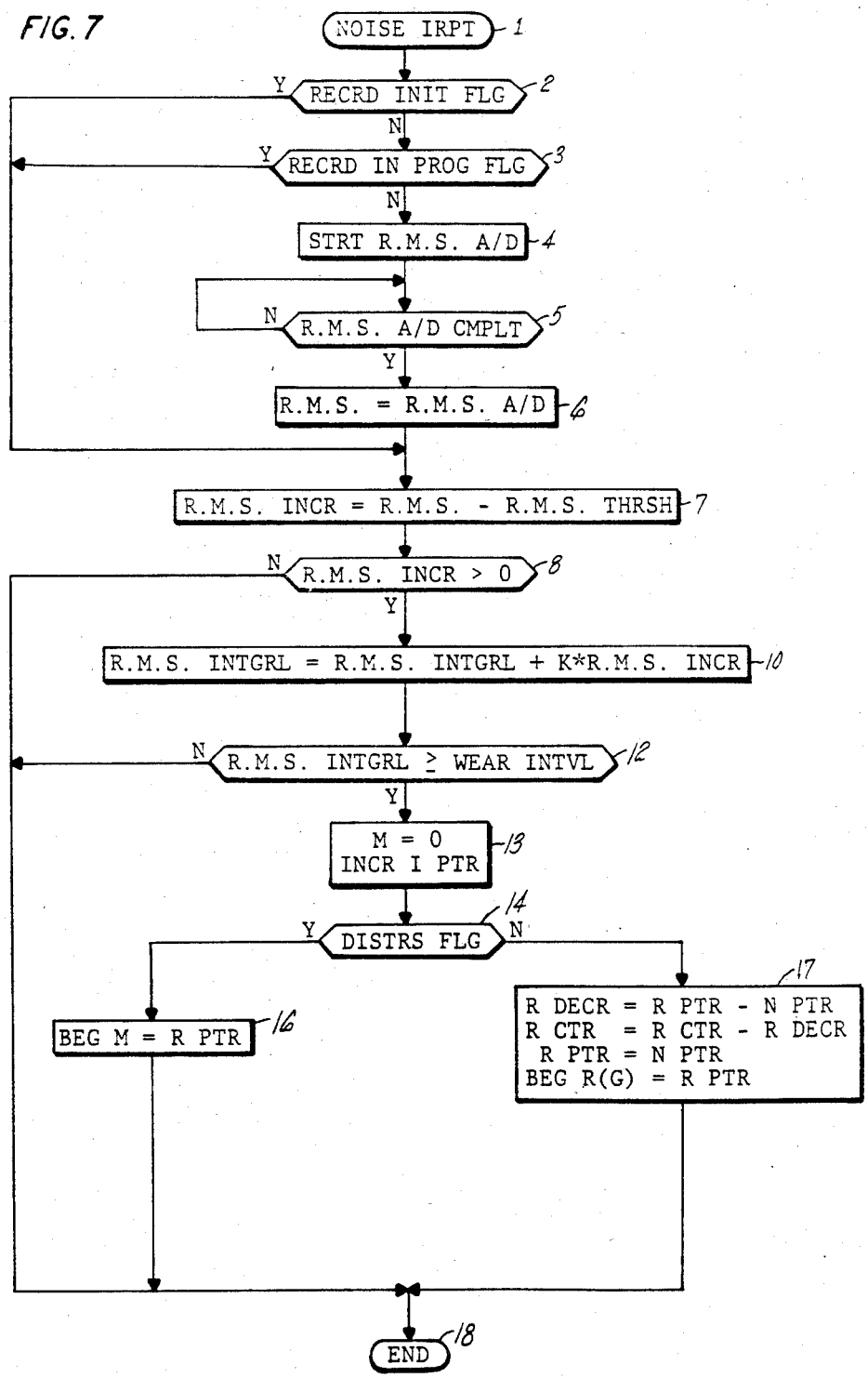
Figure 8:
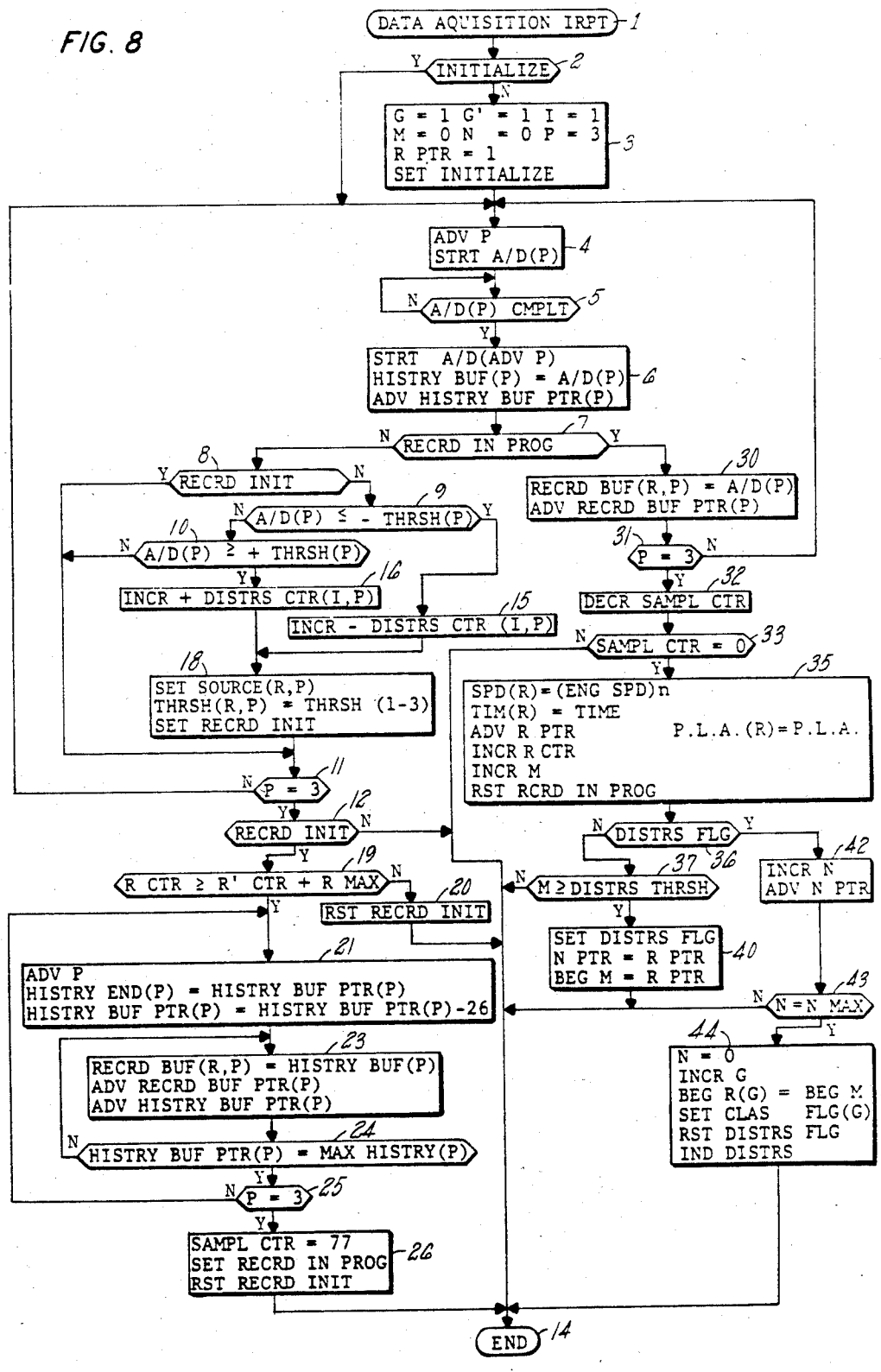
Figure 9:
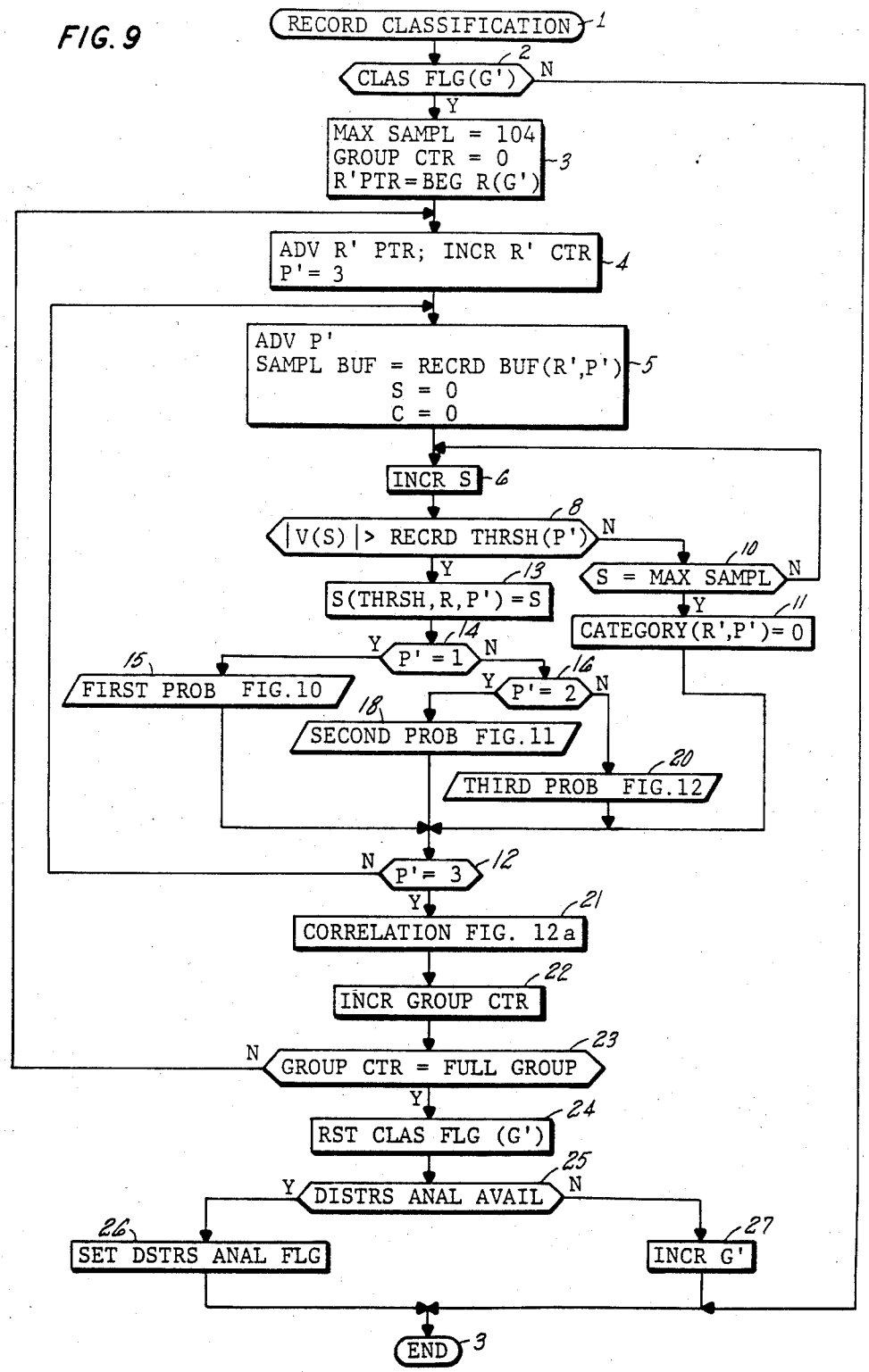
Figure 10:
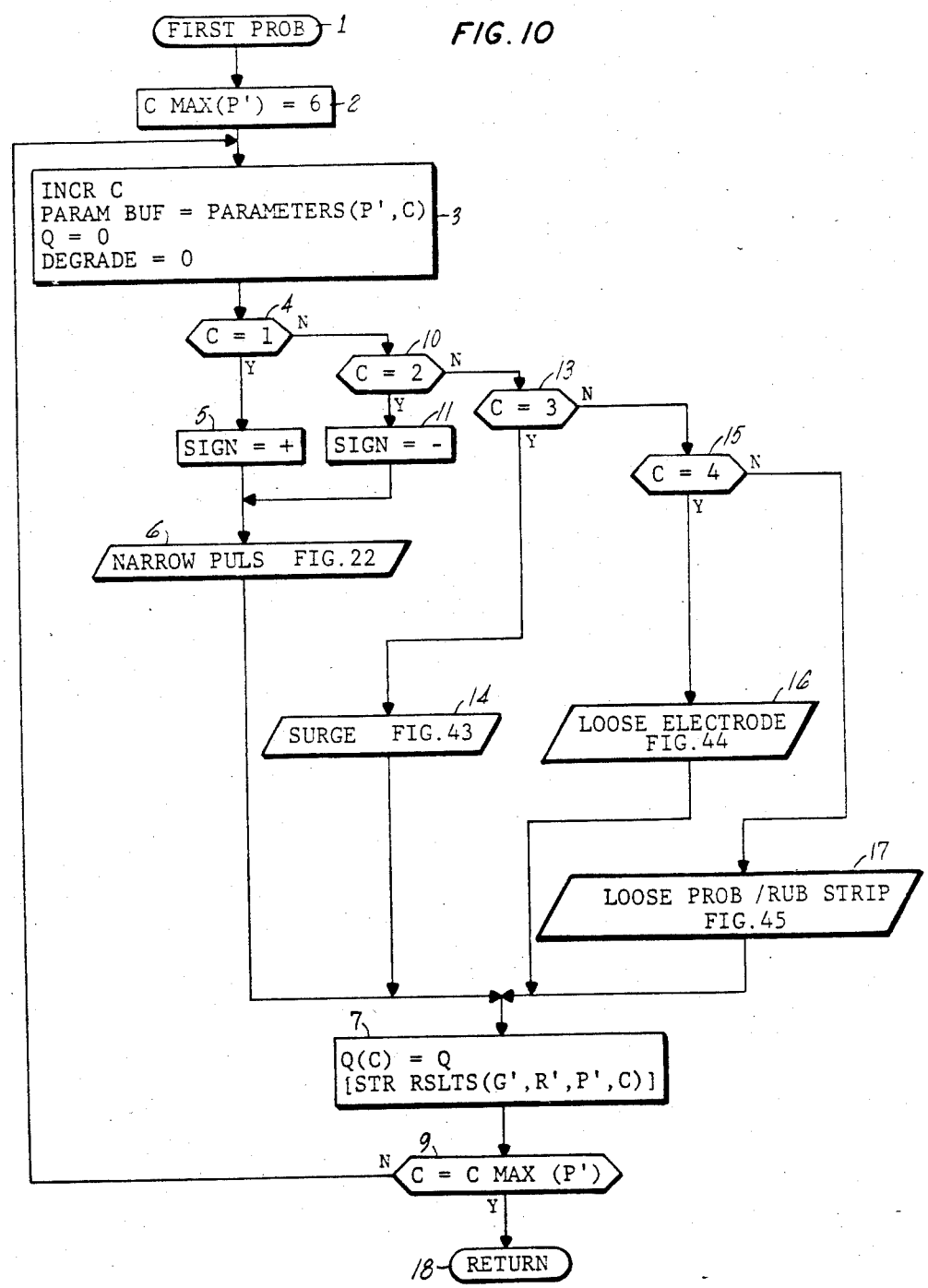
Figure 11:
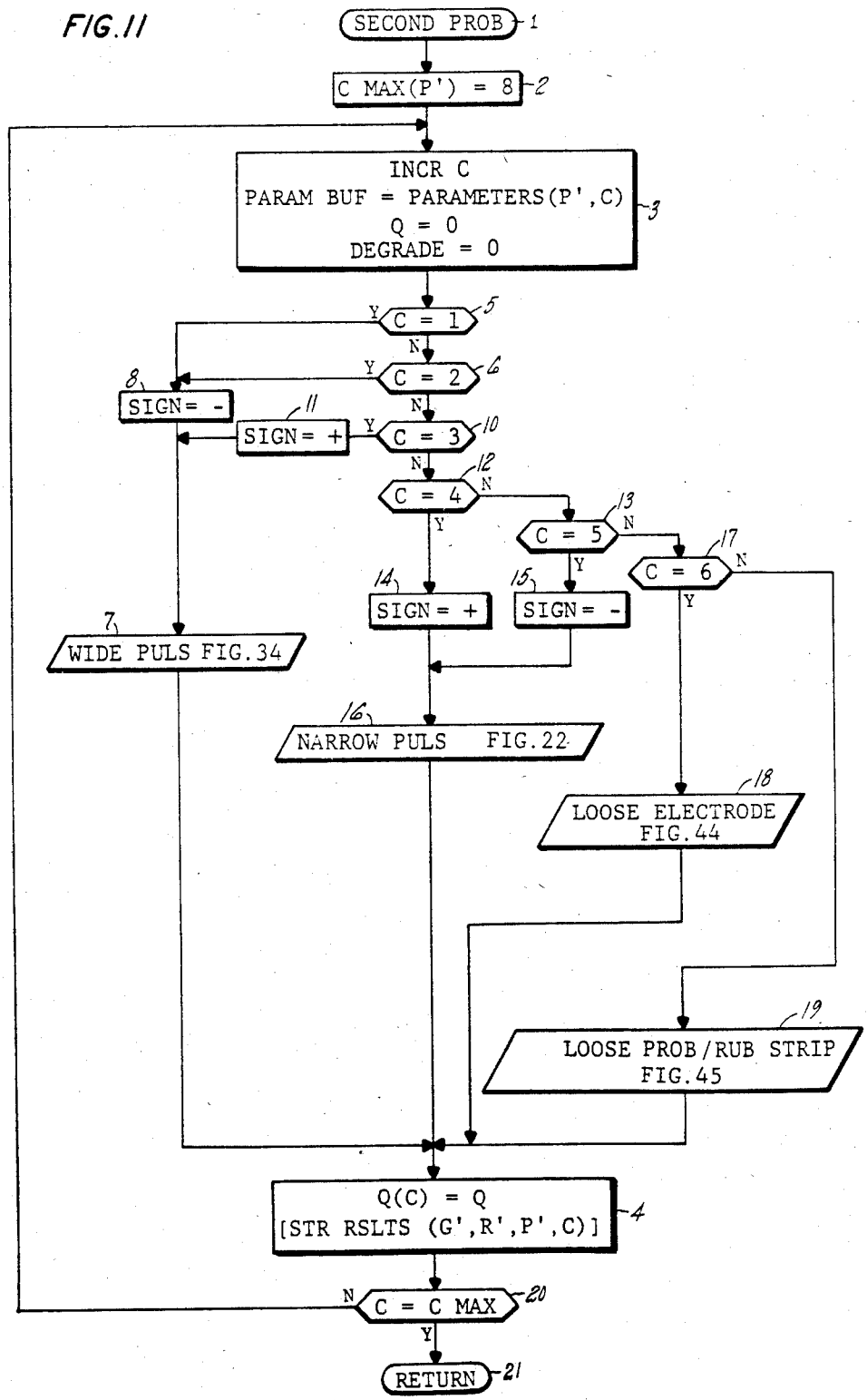
Figure 12:
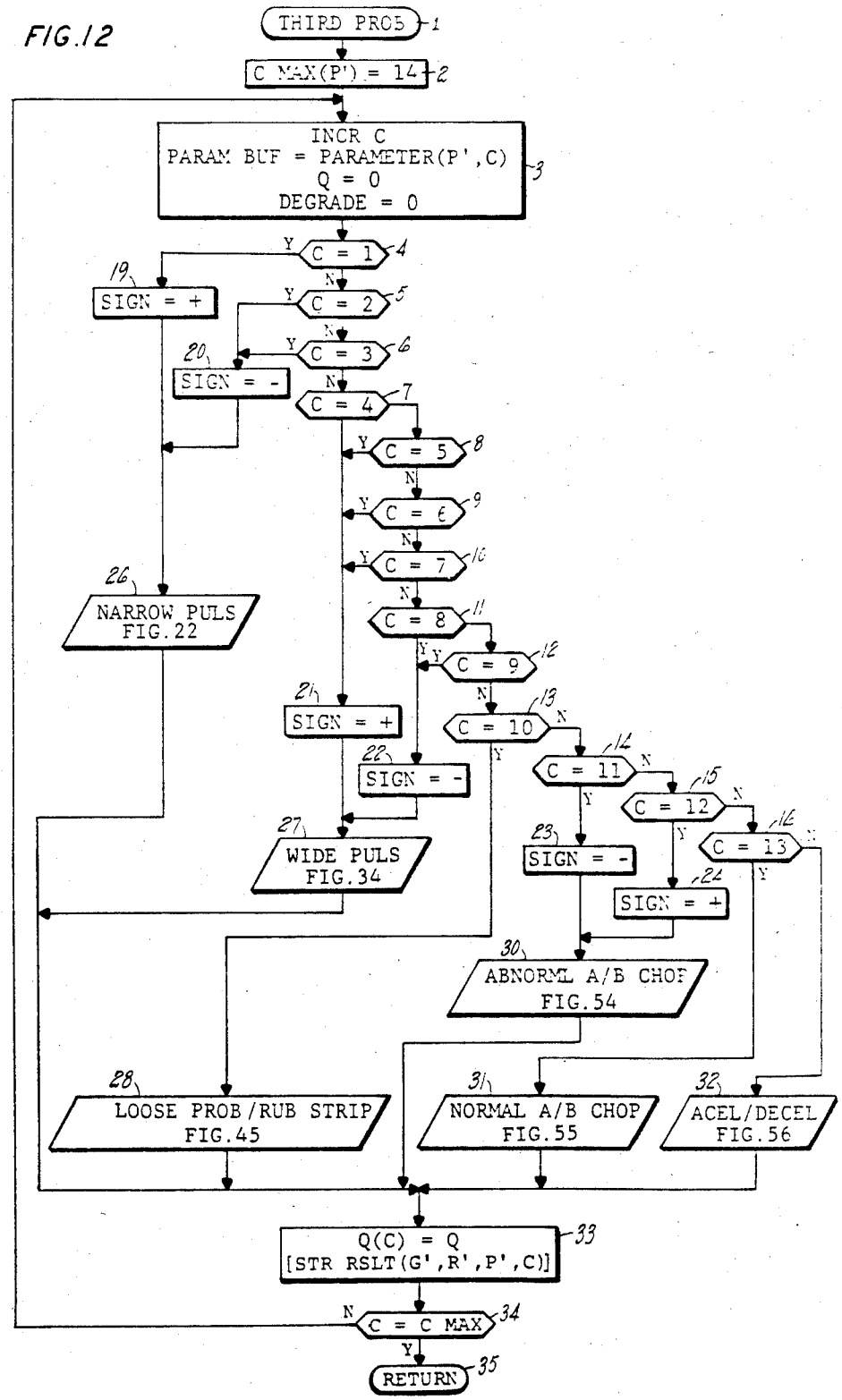
Figure 12A:
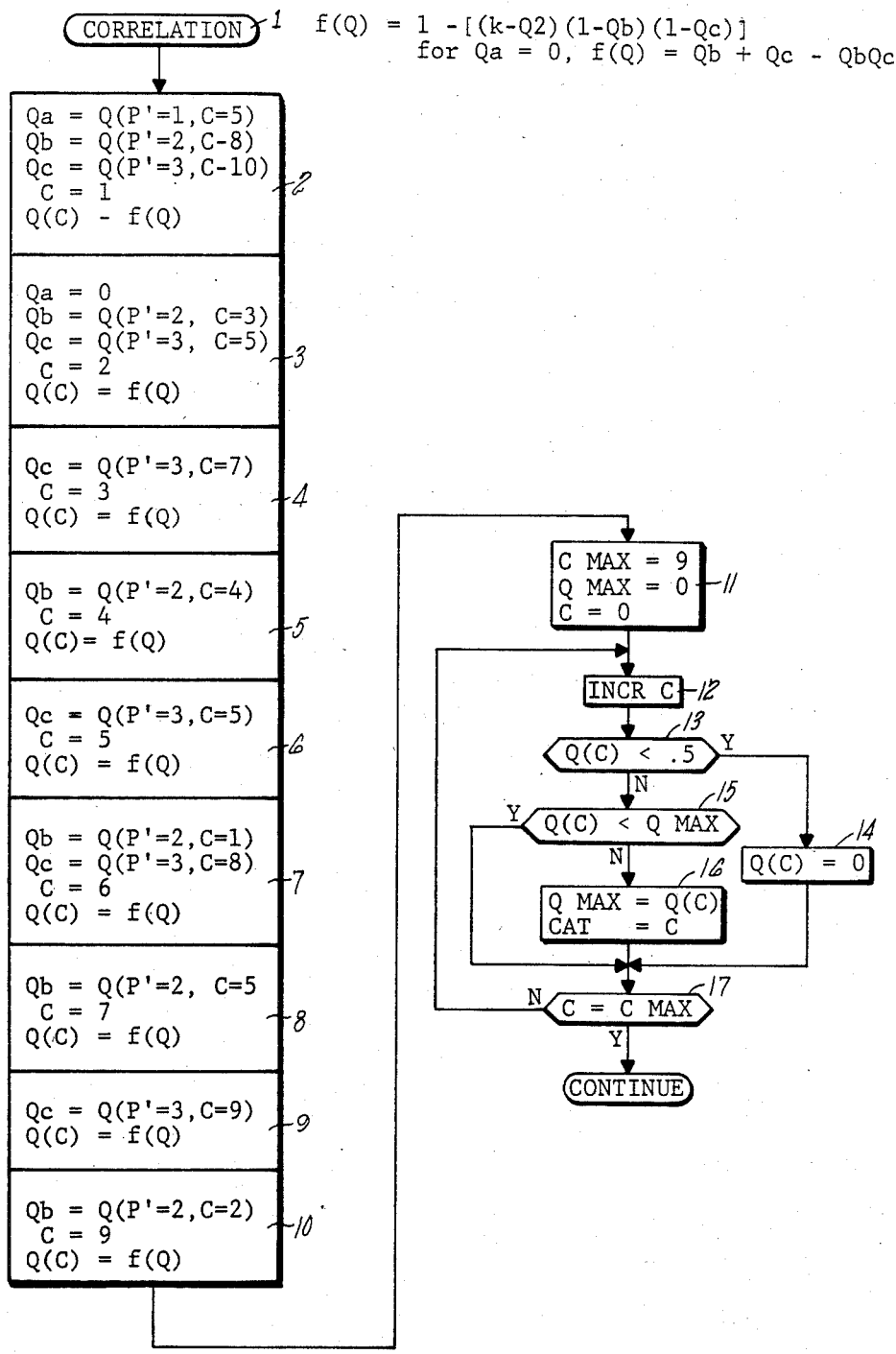
Figure 14:
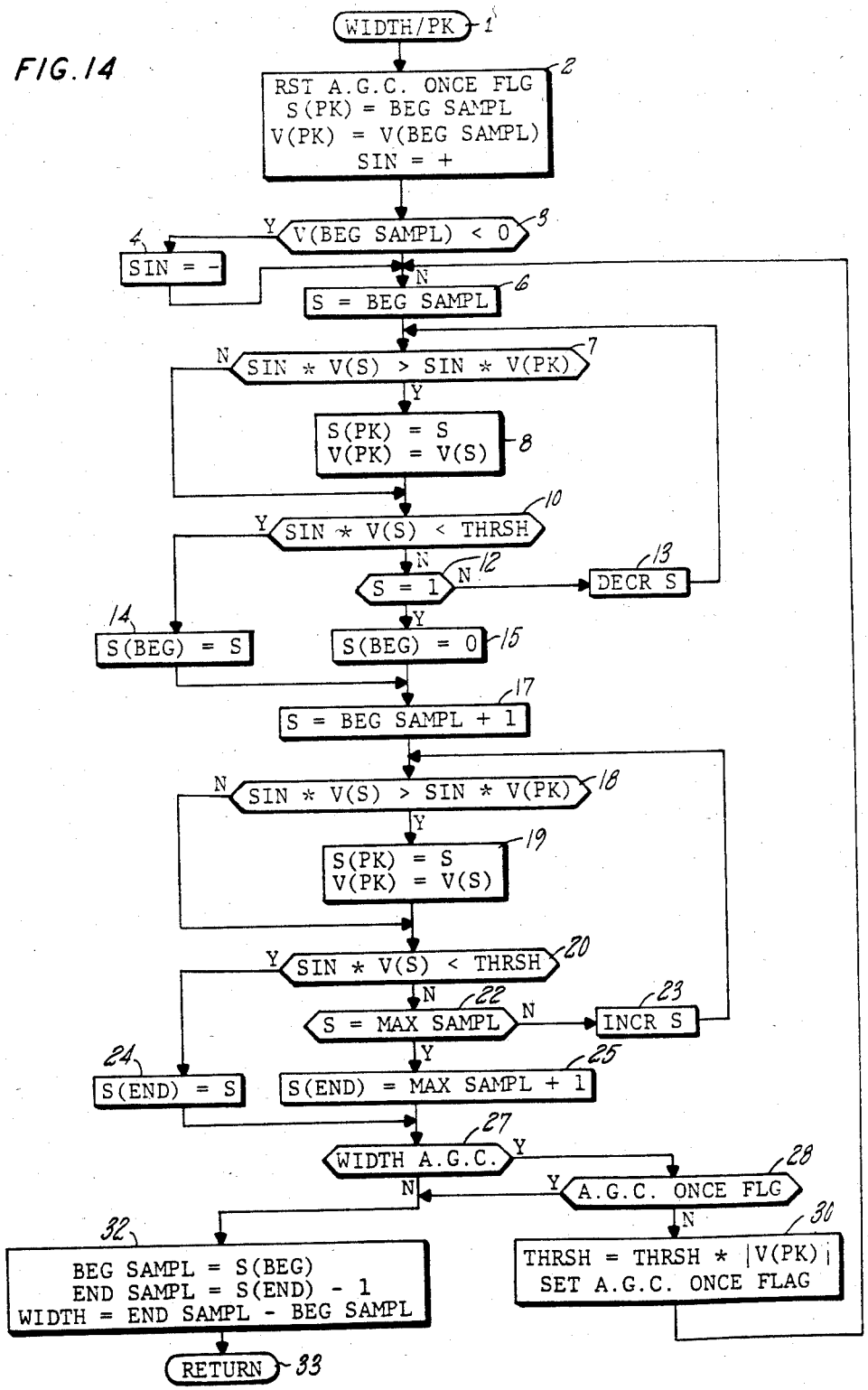
Figure 15:
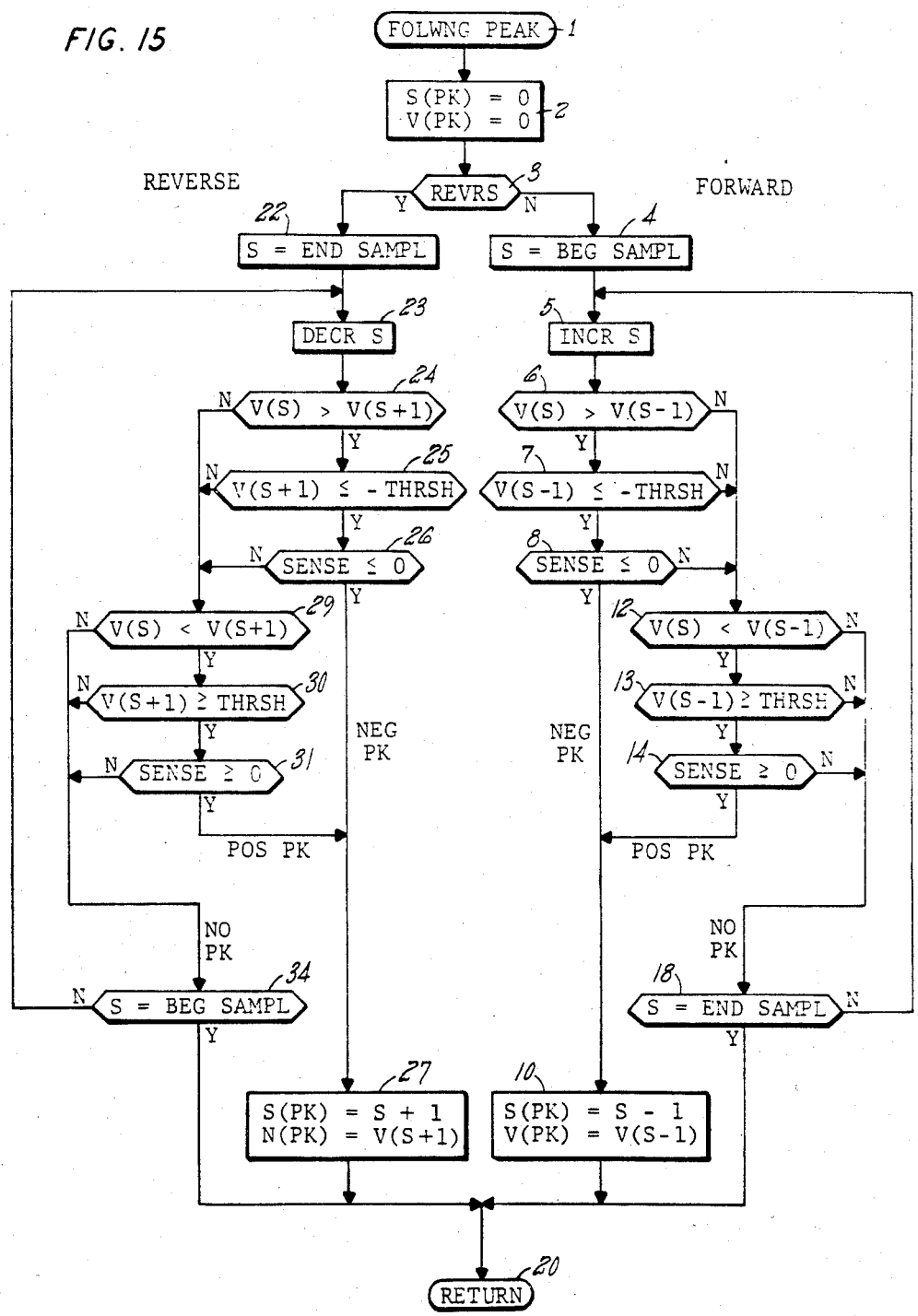
Figure 16:
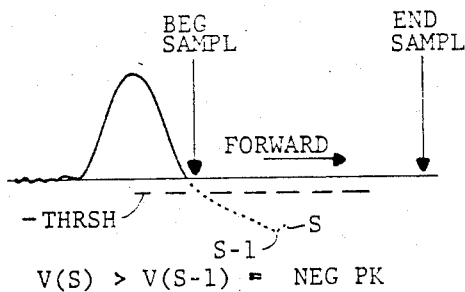
Figure 17:
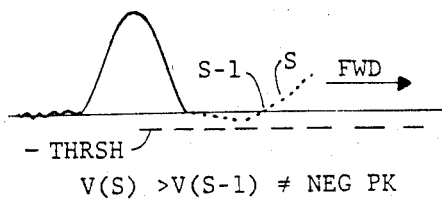
Figure 18:
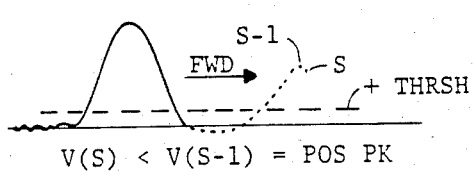
Figure 19:
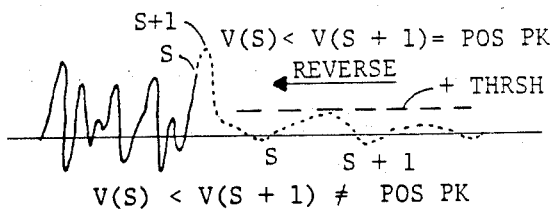
Figure 21:
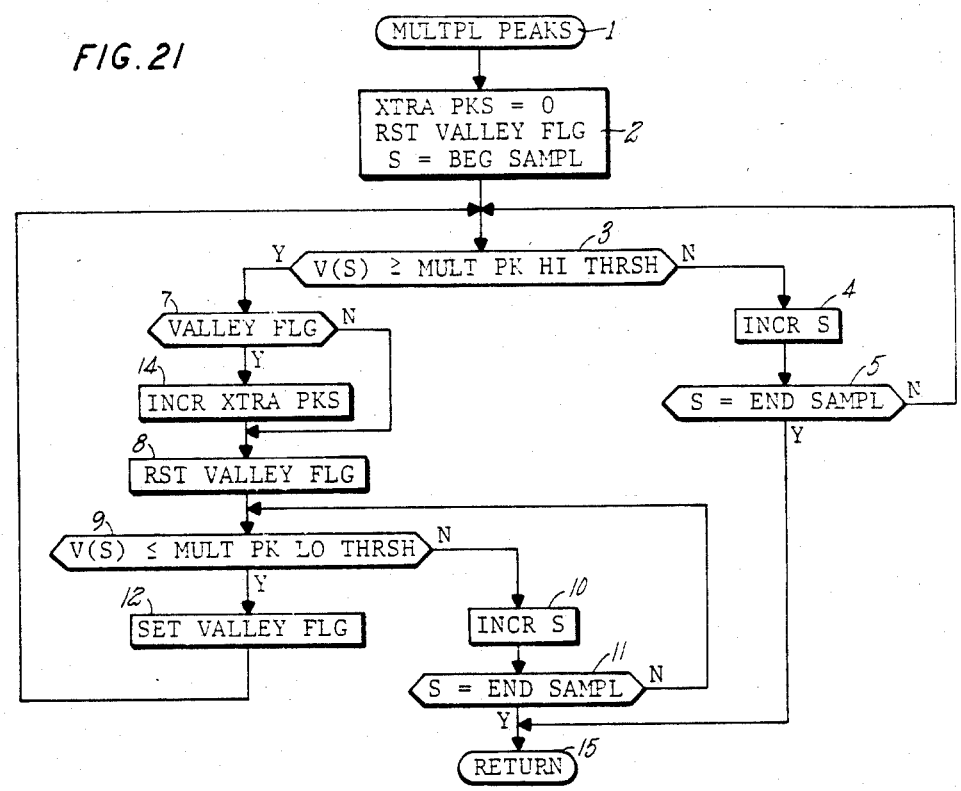
Figure 22:
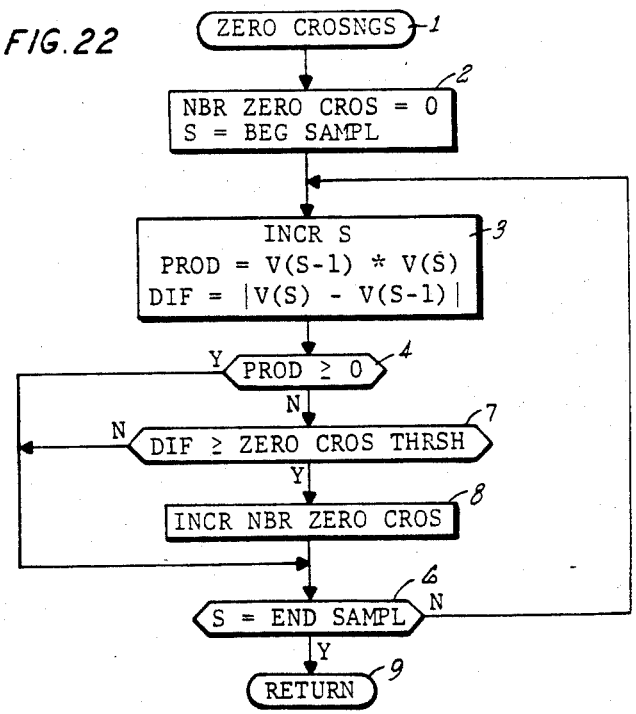
Figure 23:
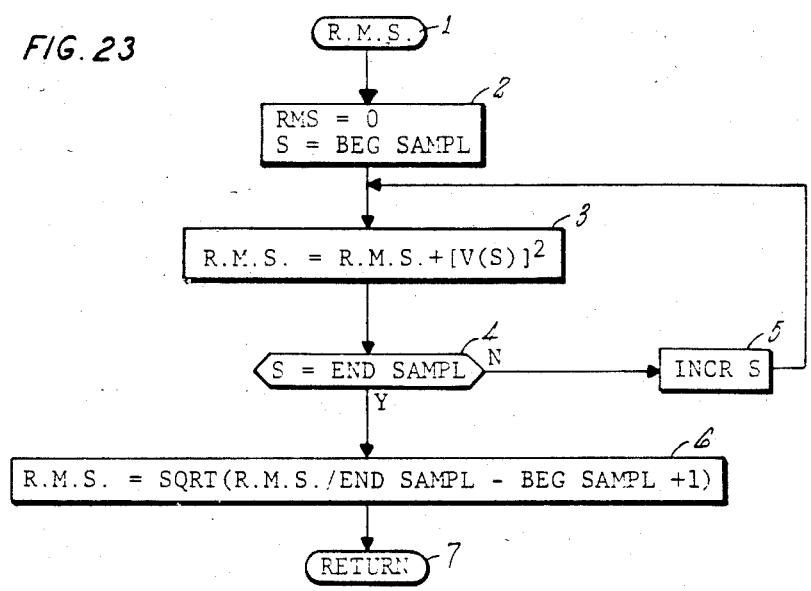
Figure 24:
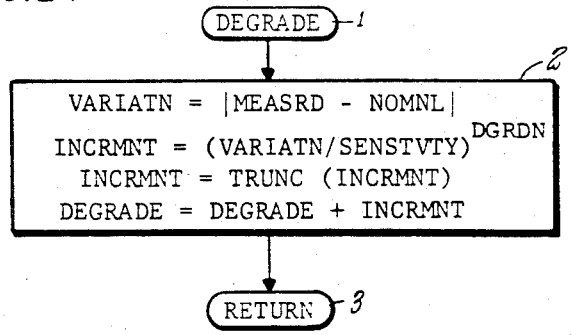
Figure 25A:
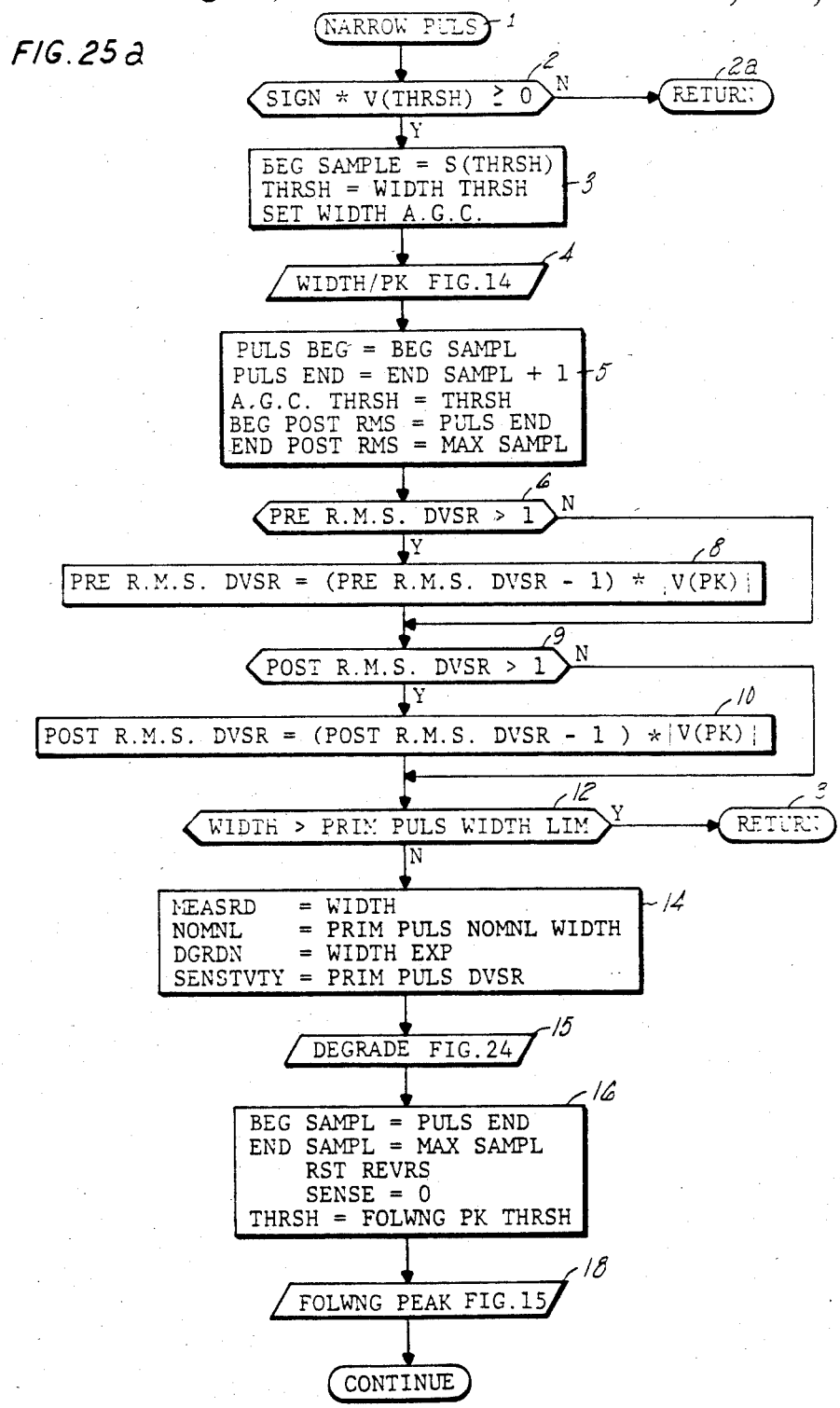
Figure 25B:
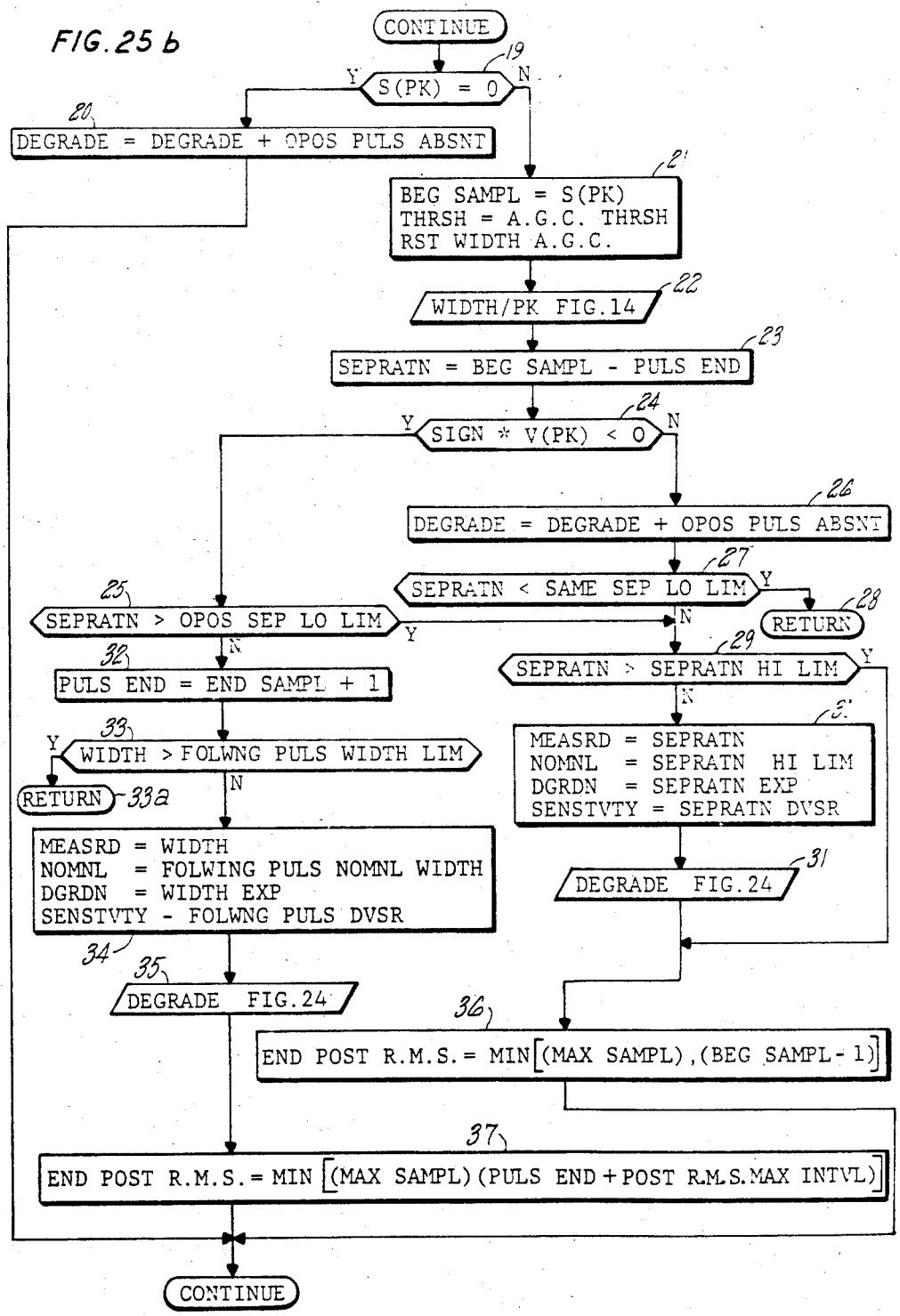
Figure 25C:
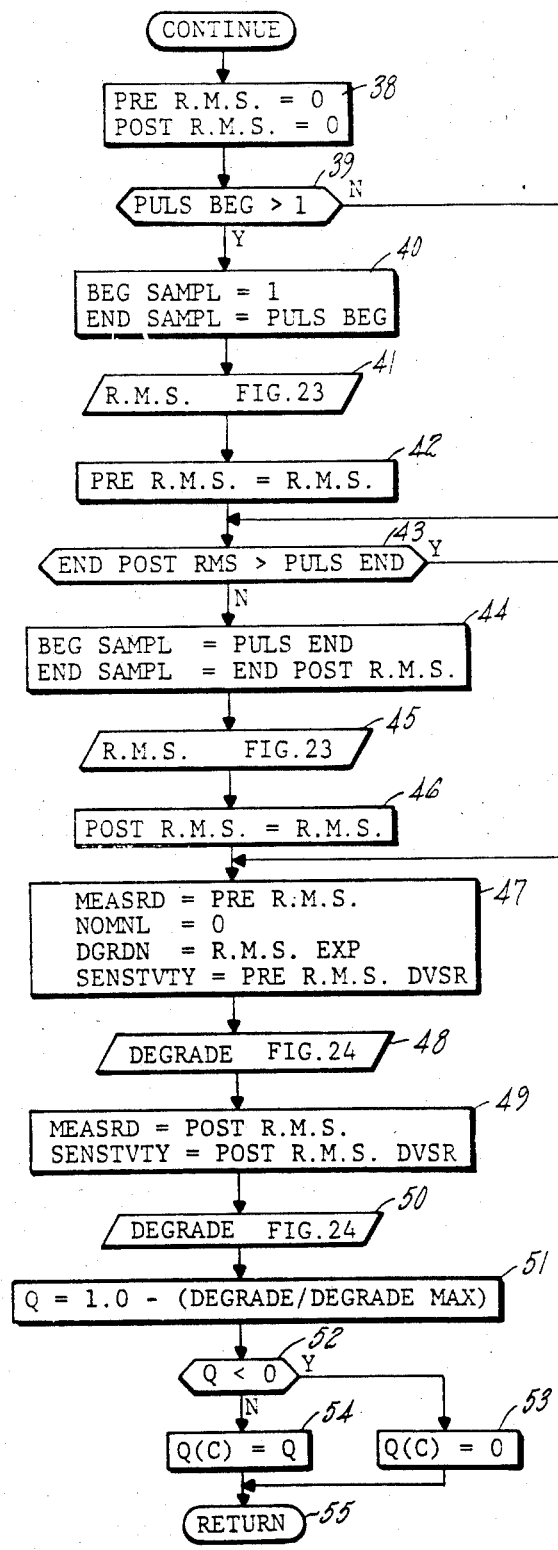
Figure 43:
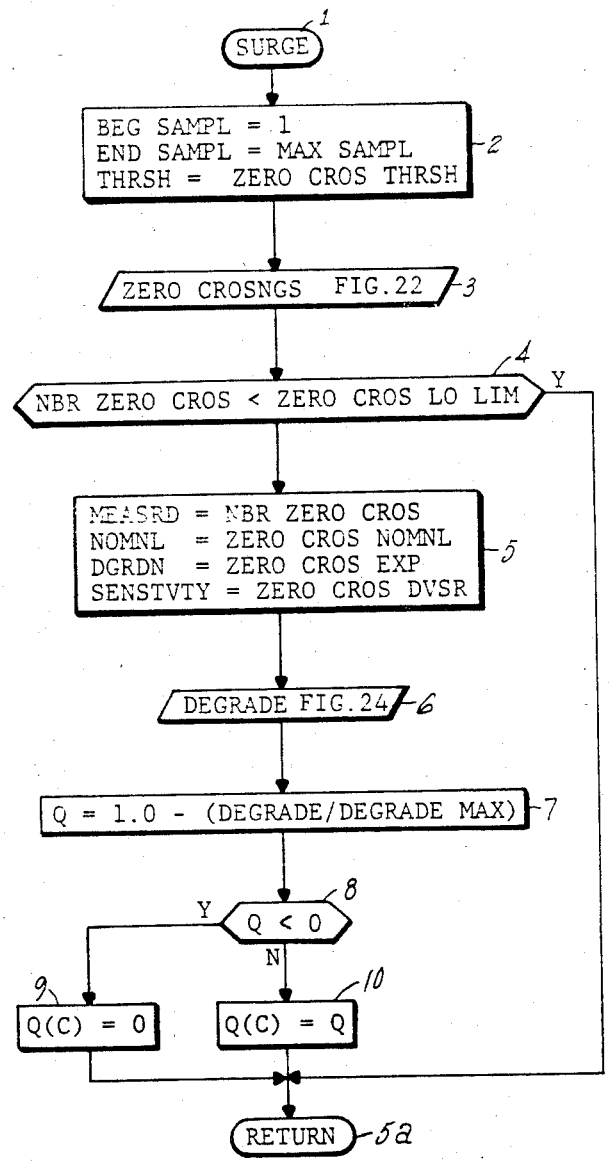
Figure 44:
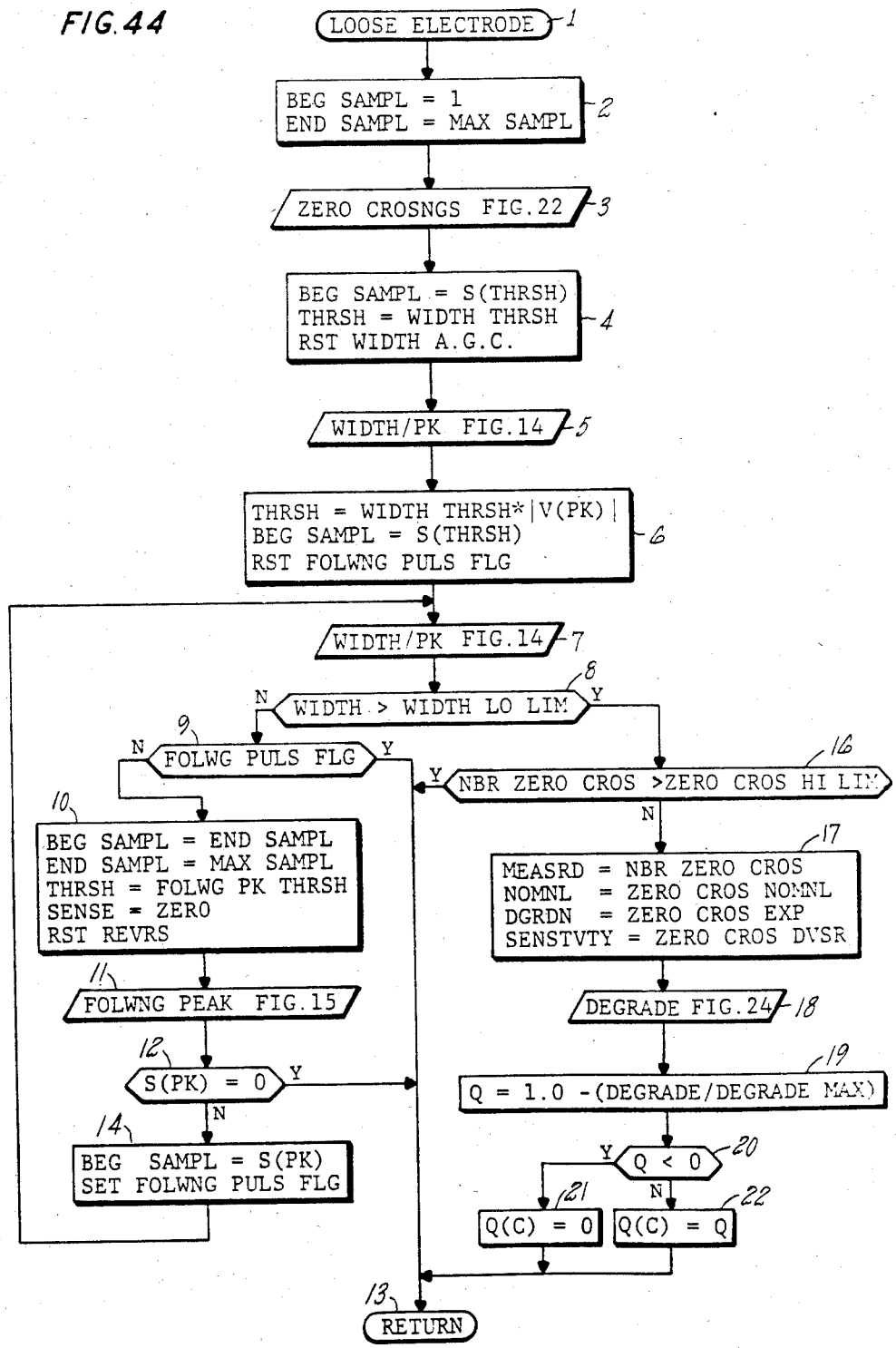
Figure 45A:
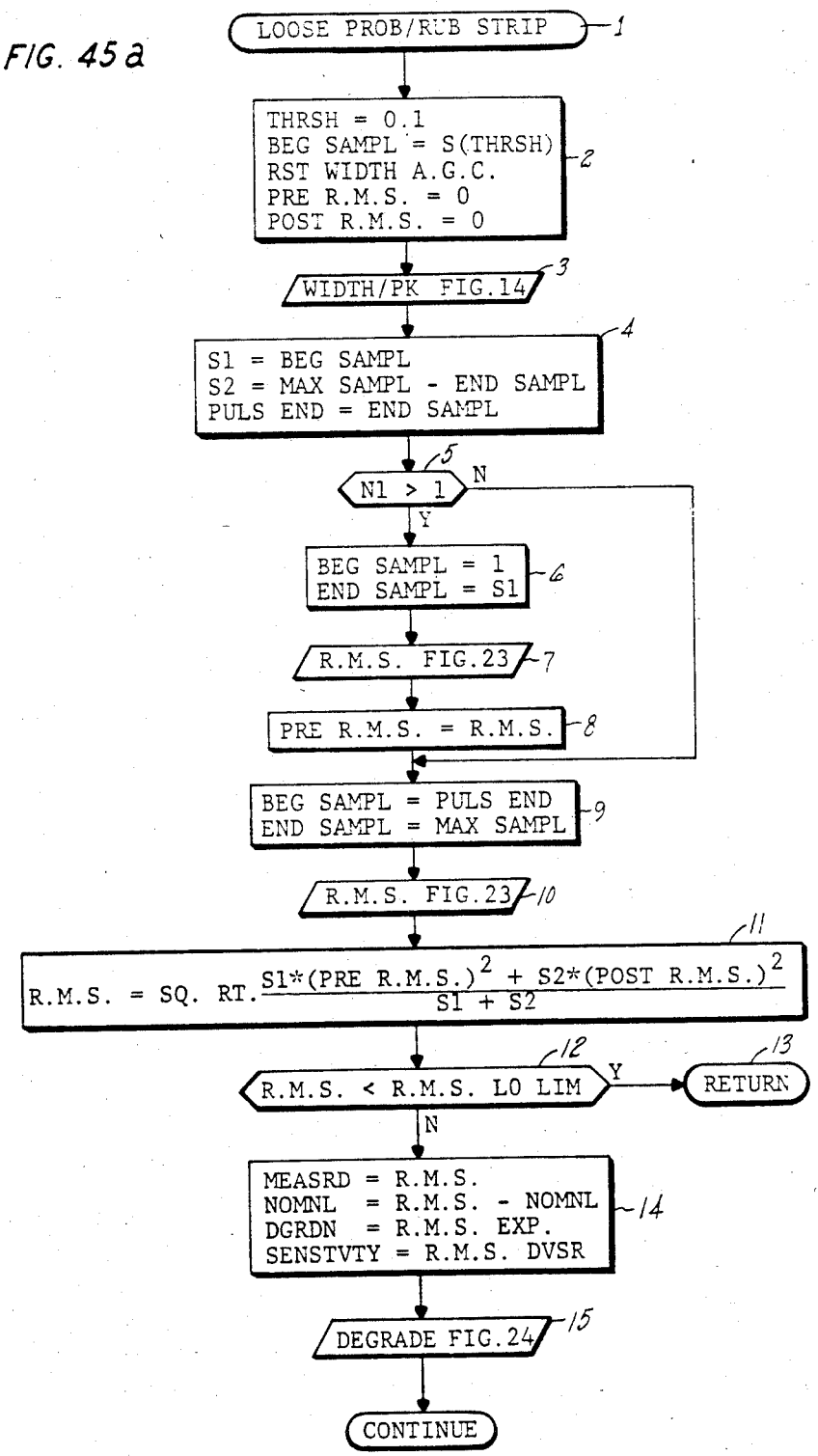
Figure 45B:
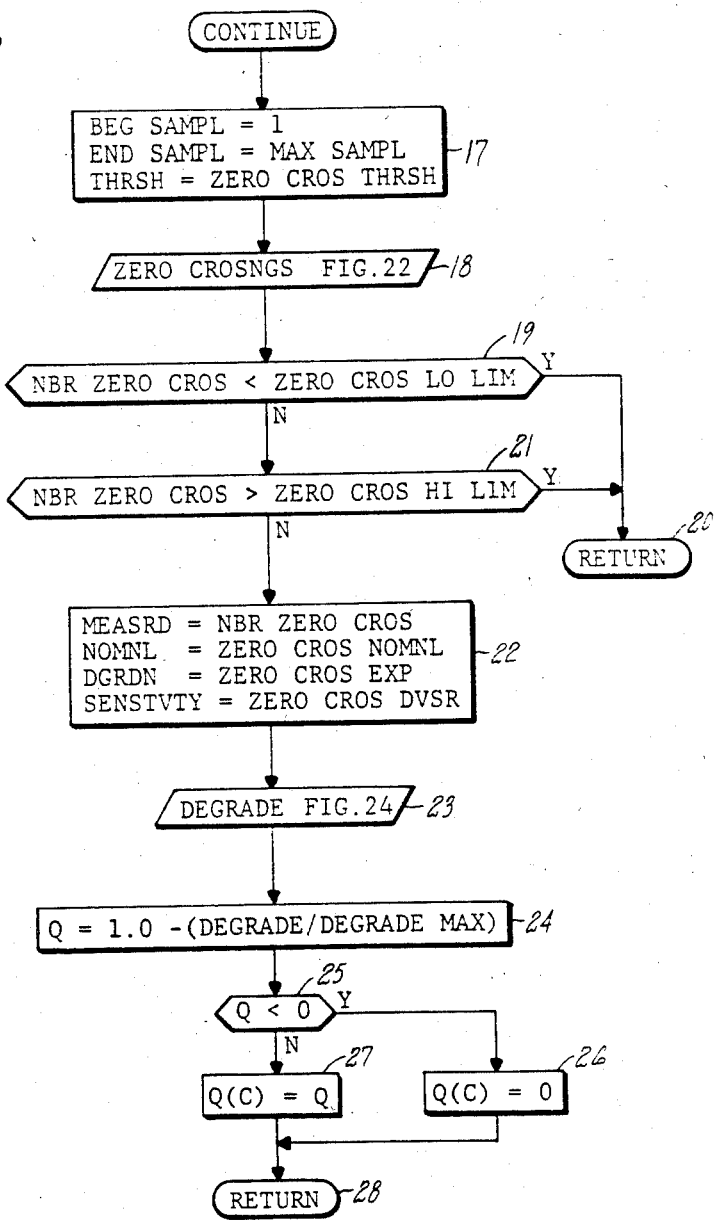
Figure 54A:
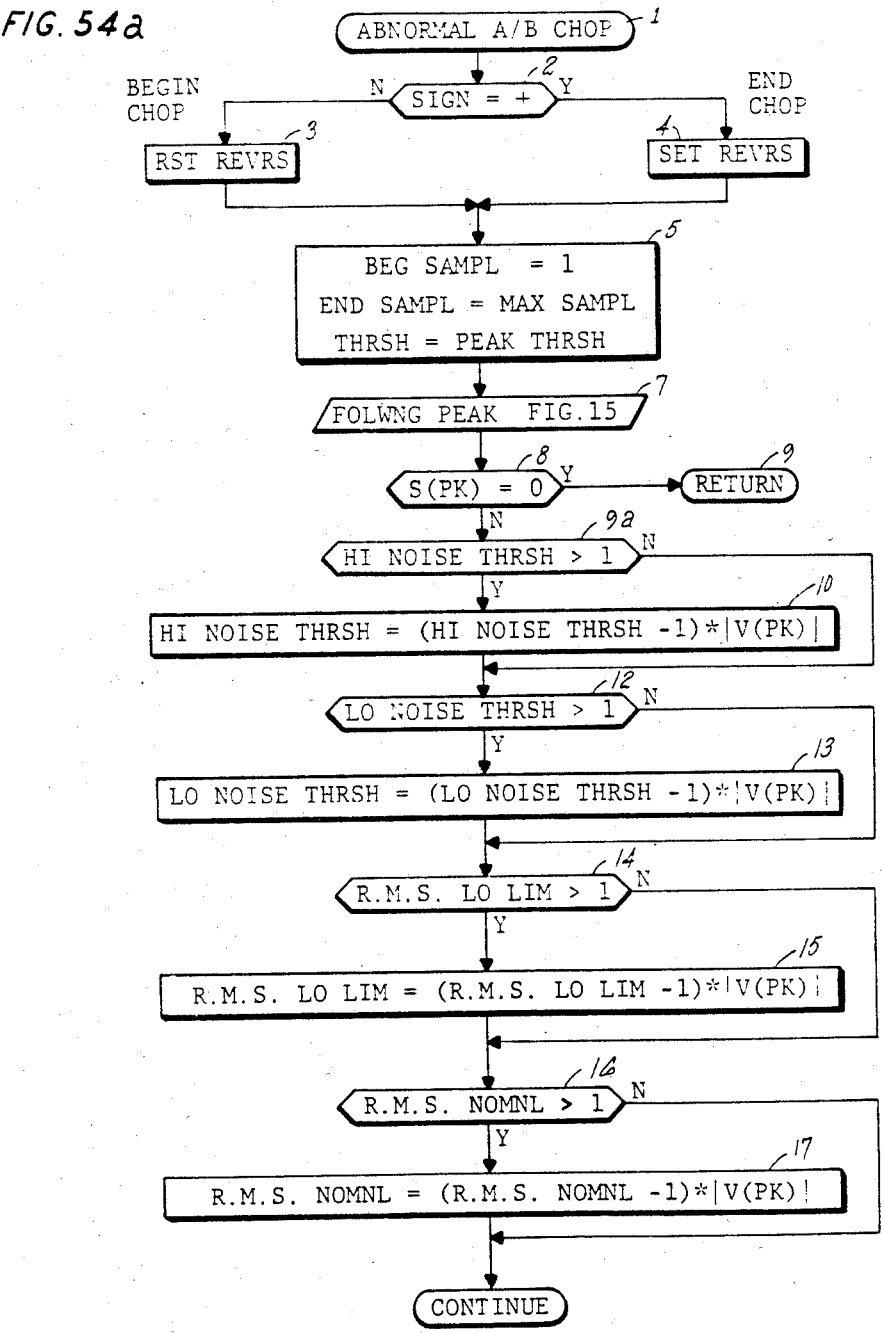
Figure 54B:
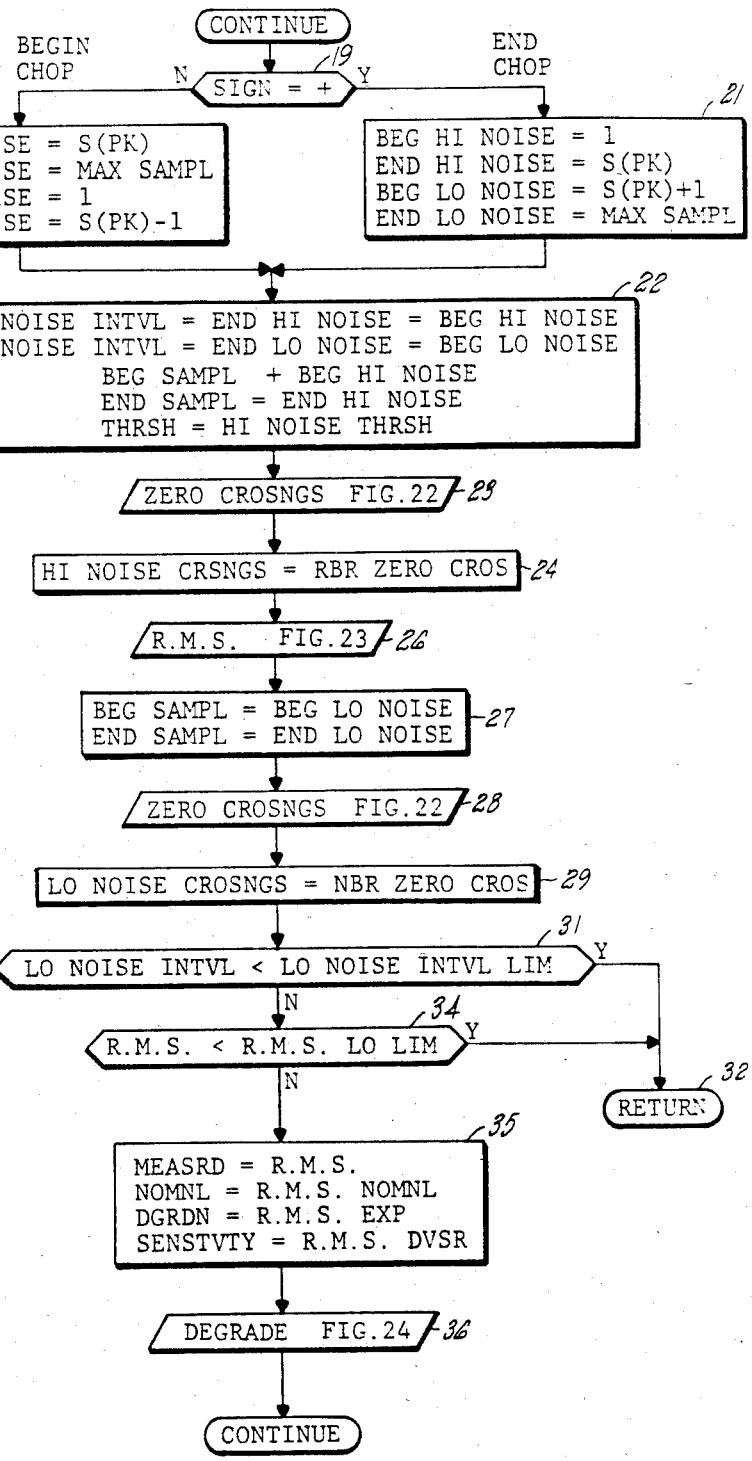
Figure 55A:
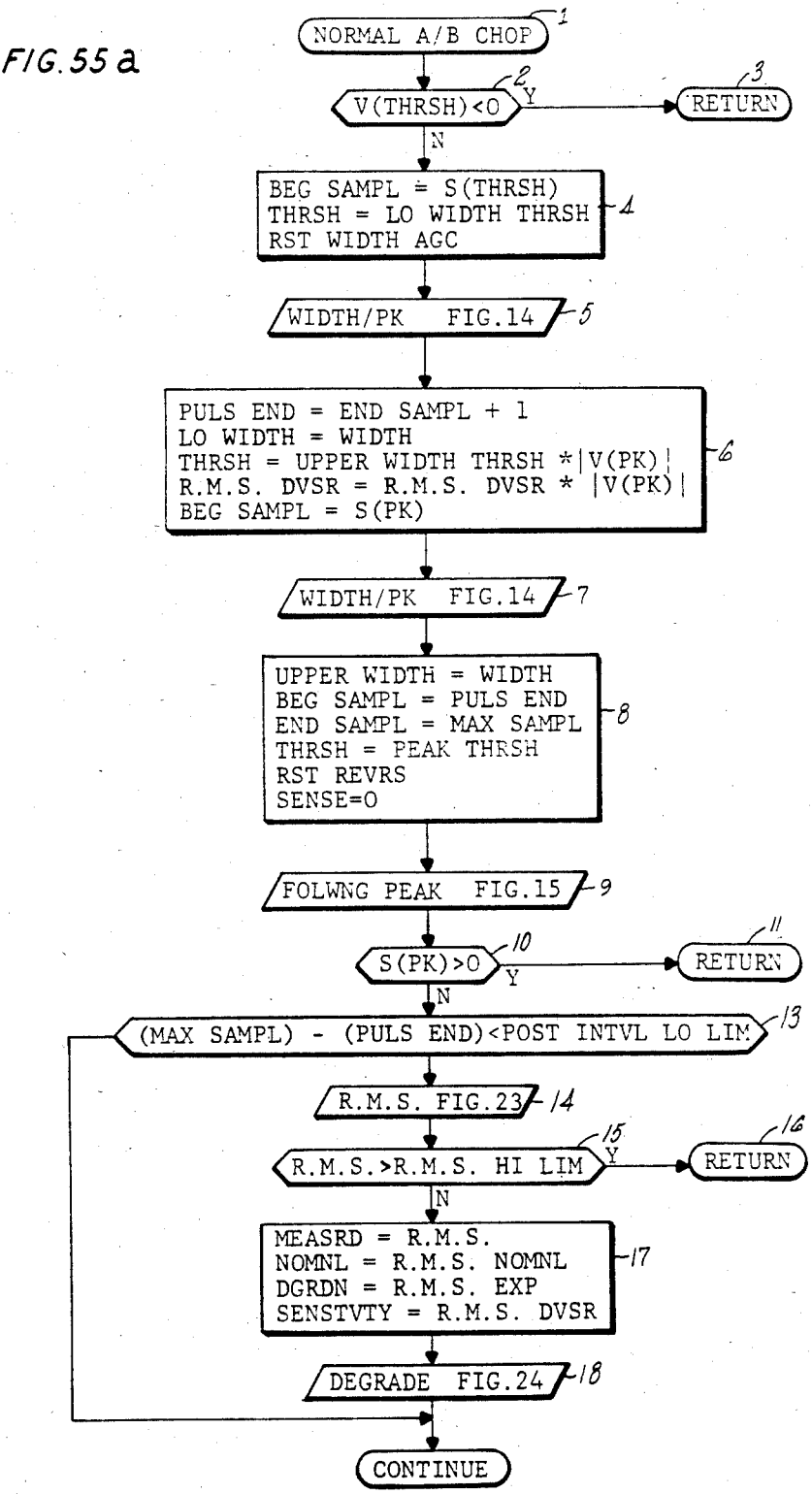
Figure 55B:
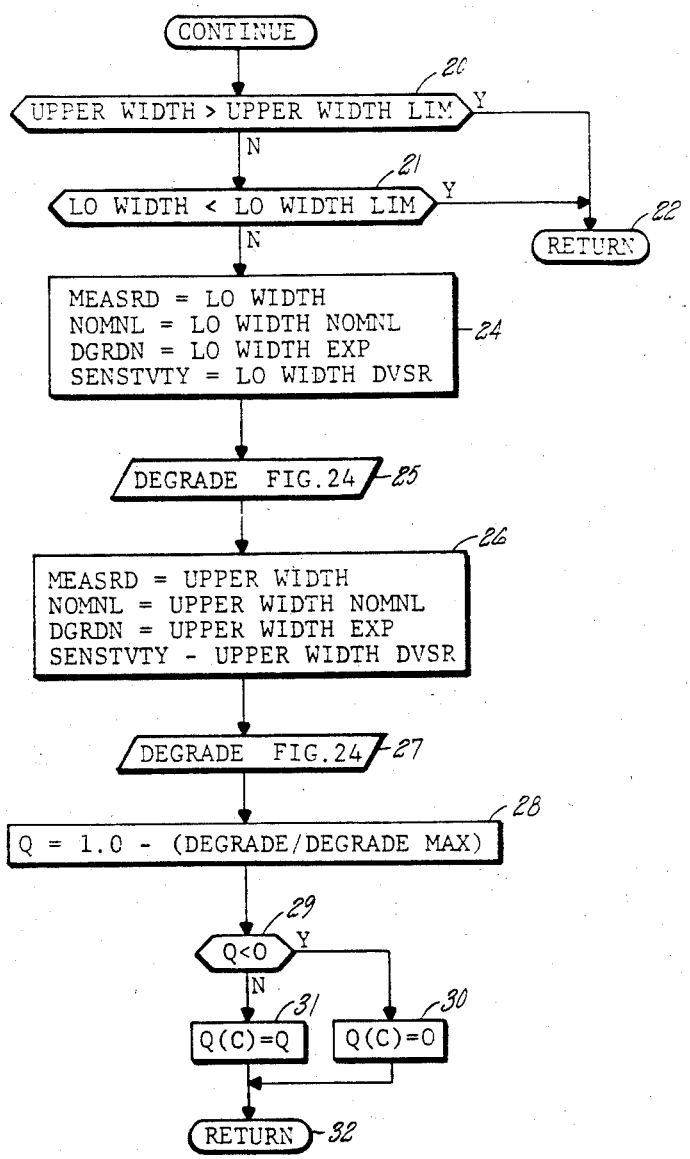
Figure 56:
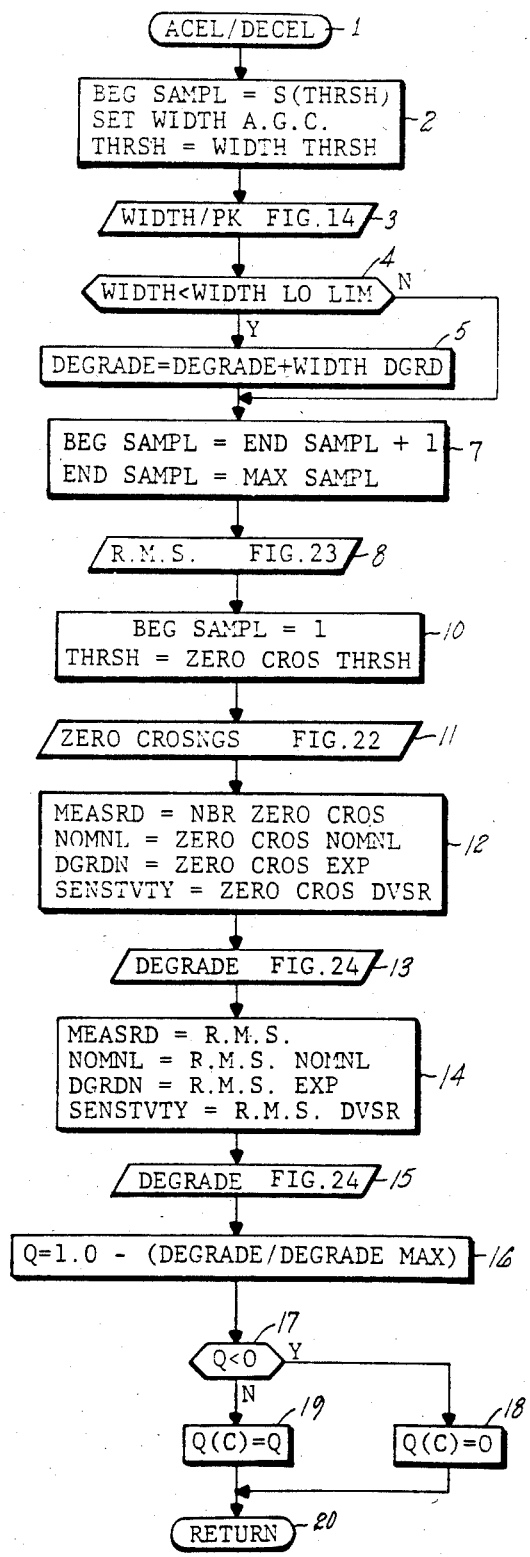
Figure 81:
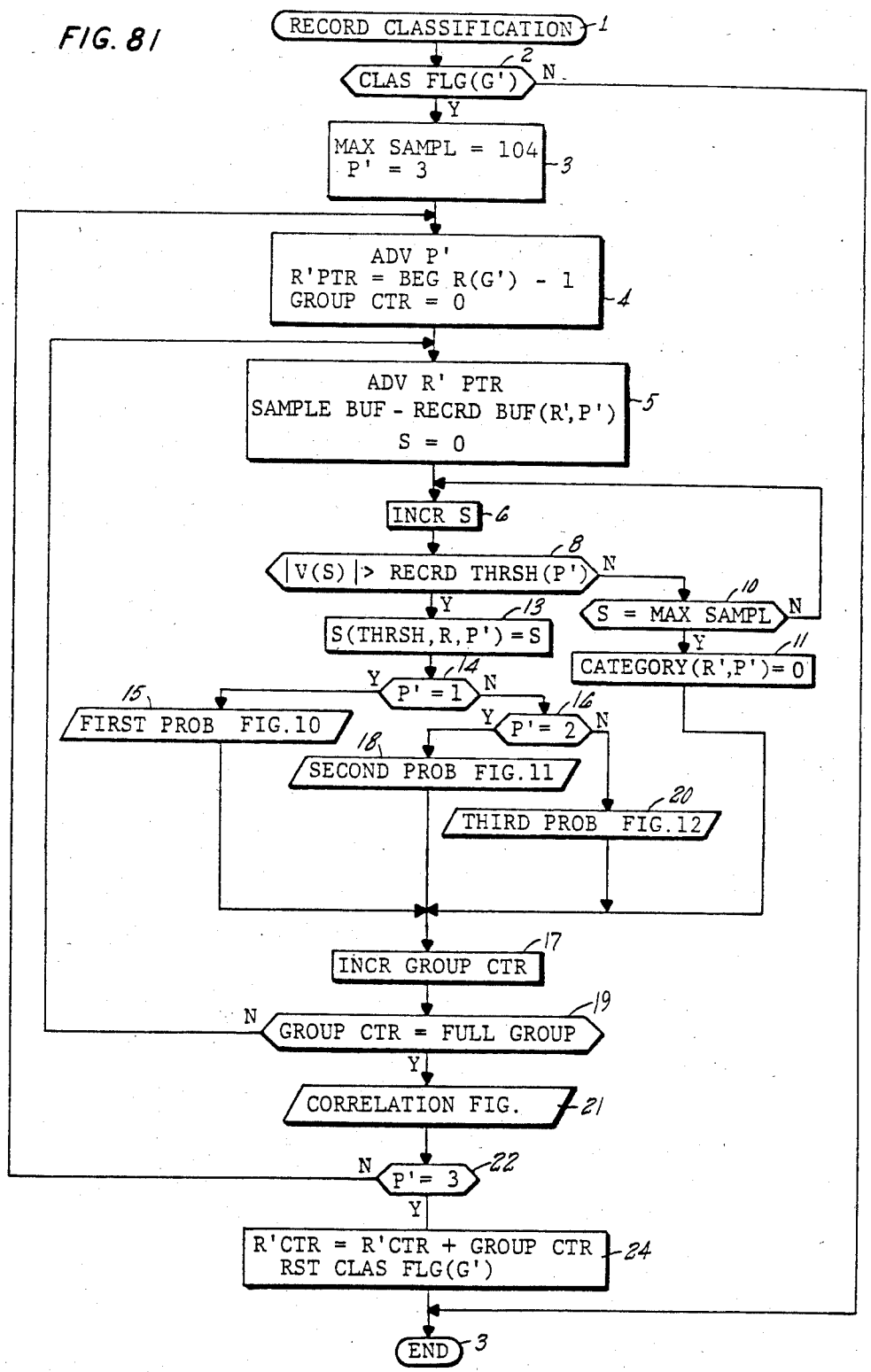
Figure 82:
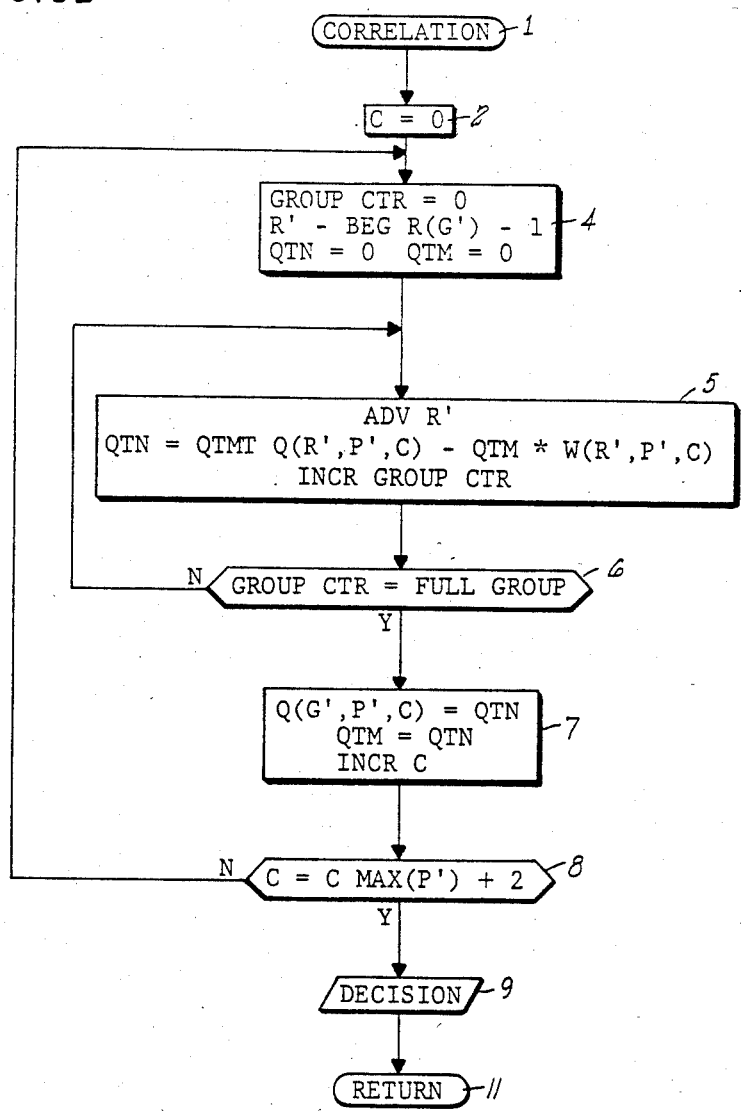

The following are logic flow diagrams of exemplary computer program routines:

FIG. 3—engine speed request interrupt;
FIG. 4—engine speed ready interrupt;
FIG. 5 and FIG. 6 are illustrative diagrams of data acquisition and data storage;

The following are logic flow diagrams of exemplary computer program routines:

FIG. 7—noise interrupt;
FIG. 8—data acquisition interrupt of prior art;
FIG. 9—record classification;
FIG. 10—first probe;
FIG. 11—second probe;
FIG. 12—third probe;
FIG. 12a, 12b—correlation
FIG. 13—decision;
FIG. 14—width/peak;
FIG. 15—following peak;
FIG. 16 through FIG. 20 are illustrative waveforms useful in understanding the subroutines;

The following are logic flow diagrams of exemplary computer program routines:

FIG. 21—multiple peaks;
FIG. 22—zero crossings;
FIG. 23—R.M.S.;
FIG. 24—degrade;
FIGS. 25a, and 25b, and 25c,—narrow pulse;
FIG. 26 through FIG. 33 are illustrative waveforms useful in understanding the subroutines;

The following is a logic flow diagram of an exemplary computer program routine:

FIGS. 34a, 34b, 34c, and 34d,—wide pulse;
FIG. 35 through FIG. 42 are illustrative waveforms useful in understanding the subroutines;

The following are logic flow diagrams of exemplary computer program routines:

FIG. 43—surge;
FIG. 44—loose electrode;
FIGS. 45a, and 45b—loose connector/rub strip;
FIG. 46 through FIG. 53 are illustrative waveforms useful in understanding the subroutines;

The following are logic flow diagrams of exemplary computer program routines:

FIGS. 54a, 54b, and 54c—abnormal A/B chop;
FIGS. 55a and 55b—normal A/B chop;
FIG. 56—acel/decel;

The following are diagrams of exemplary waveshapes resulting from electrostatic activity in the gas path of the engine, which are discriminated in this embodiment with the probe (P) and category (C) numbers:

FIG. 57—compressor metal/abradable rub (P 1, C 1);
FIG. 58—compressor metal/metal rub (P 1, C 2);
FIG. 59—surge (P 1, C 3);
FIG. 60—loose probe electrode (P 1, C 1; P 2, C 6);
FIG. 61—loose probe connector (P 1, C 5; P 2, C 7);
FIG. 62—rub strip (P 1, C 6; P 2, C 8; P 3, C 10);
FIG. 63—first high turbine blade erosion (P 2, C 1);
FIG. 64—first high turbine vane erosion (P 2, C 2);
FIG. 65—first high turbine rub (P 2, C 3);
FIG. 66—second high turbine rub (P 2, C 4);
FIG. 67—second high turbine blade or vane erosion (P 2, C 5);
FIG. 68—flaming debris (P 3, C 1);
FIG. 69—A/B nozzle liner erosion (P 3, C 2);
FIG. 70—uncorrelated—1 (P 3, C 3);
FIG. 71—uncorrelated—2 (P 3, C 4);
FIG. 72—high turbine rub (P 3, C 5);
FIG. 73—low turbine rub (P 3, C 6);
FIG. 74—high or low turbine impact-induced rub (P 3, C 7);
FIG. 75—high turbine blade erosion (P 3, C 8);
FIG. 76—high turbine vane erosion (P 3, C 9);
FIG. 77—start of abnormal A/B chop (P 3, C 11);
FIG. 78—end of abnormal A/B chop (P 3, C 12);
FIG. 79—normal A/B chop (P 3, C 13); and
FIG. 80—acel/decel (P 3, C 14);

FIGS. 81 and 82 are illustrative waveforms useful in understanding the embodiment of FIGS. 83-88.

Figure 83:
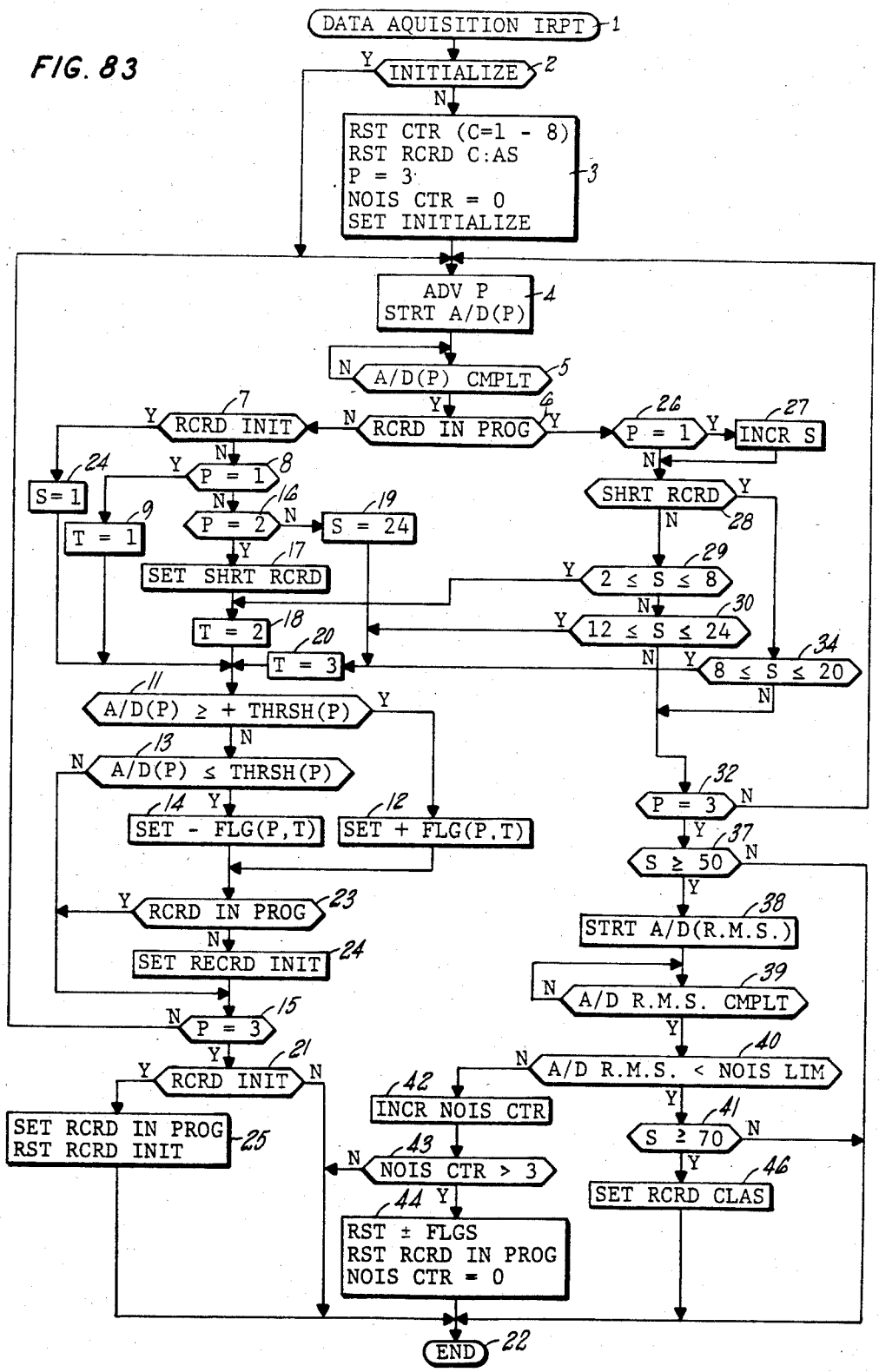
Figure 84:
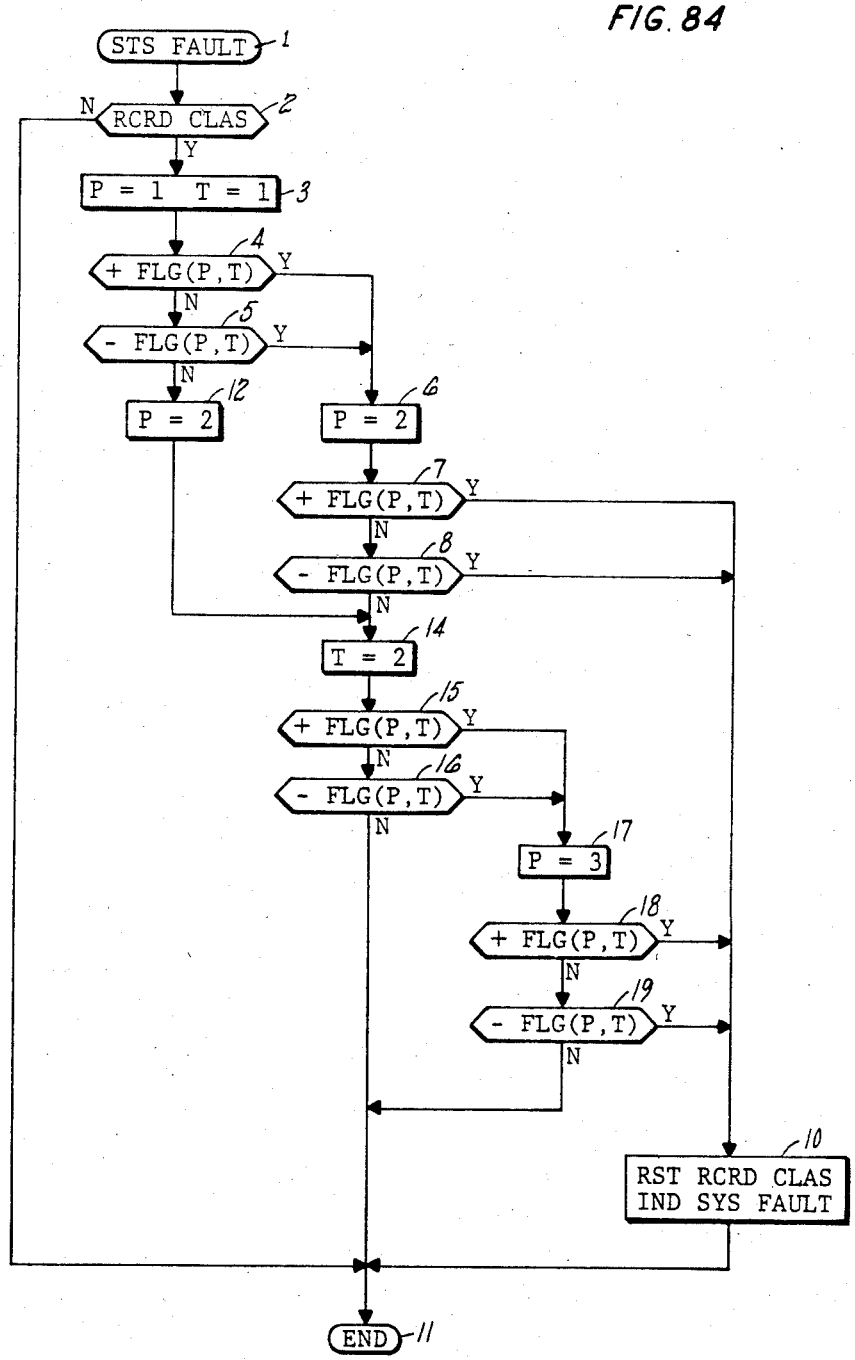
Figure 85:
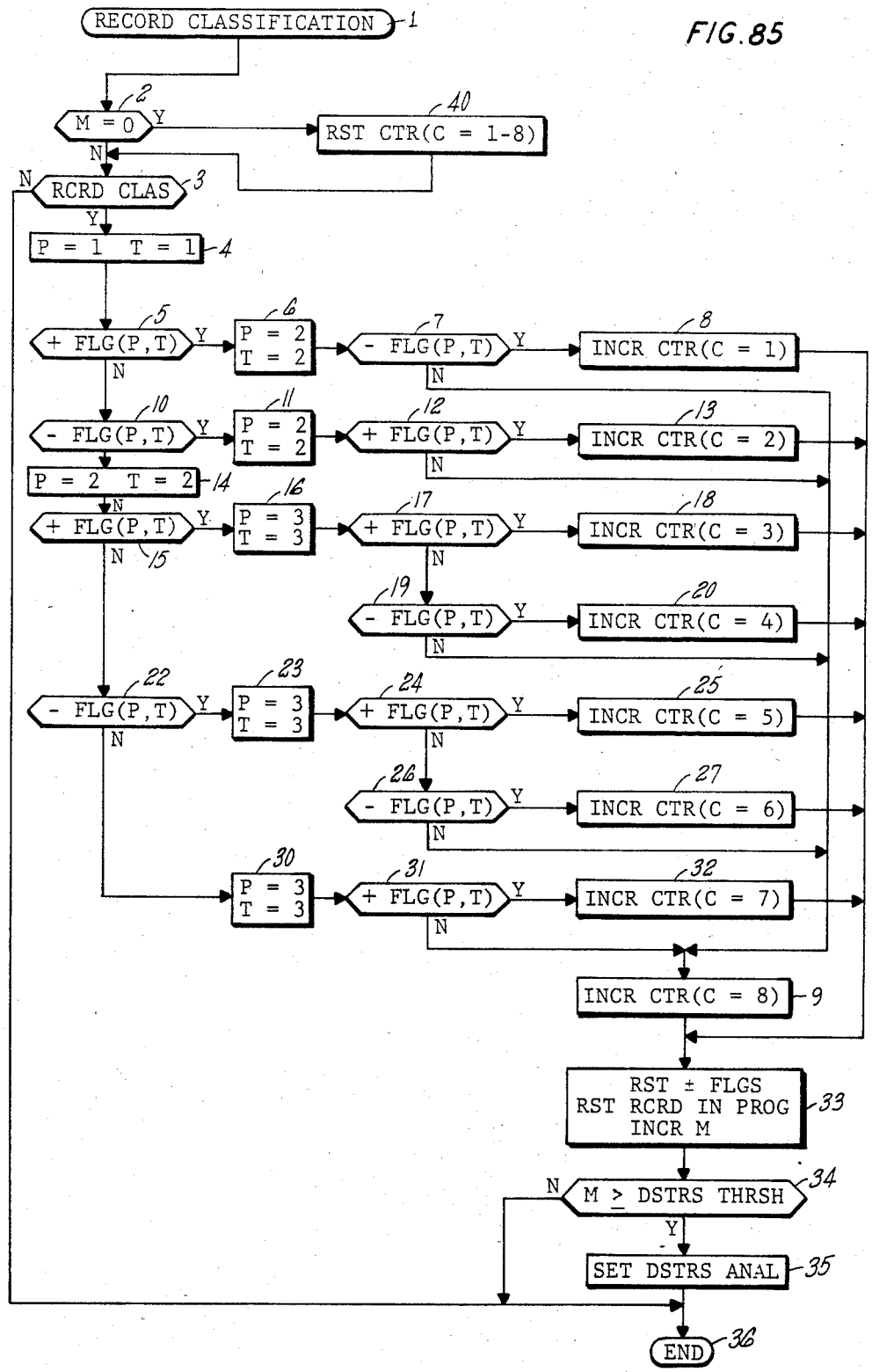
Figure 86:
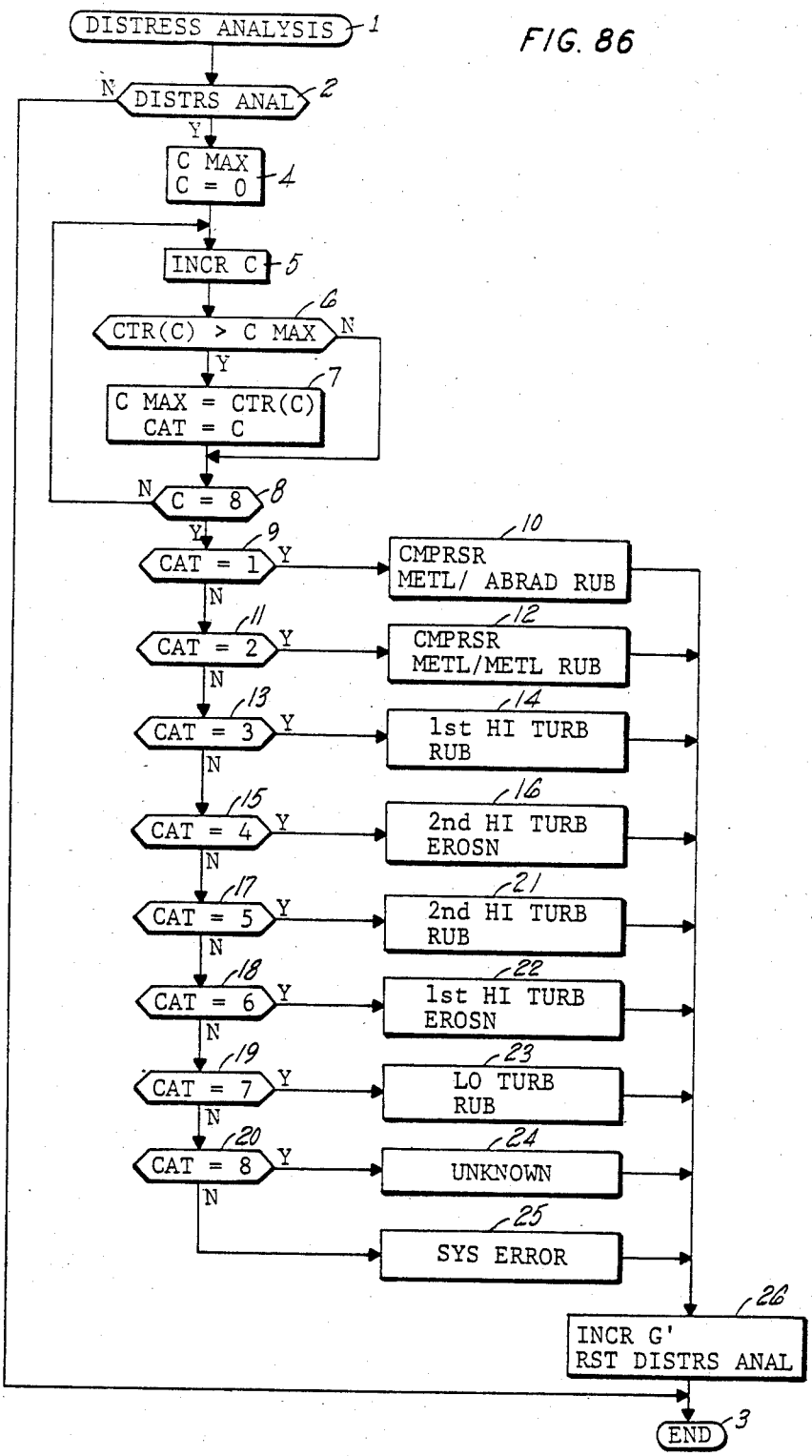
Figure 87:
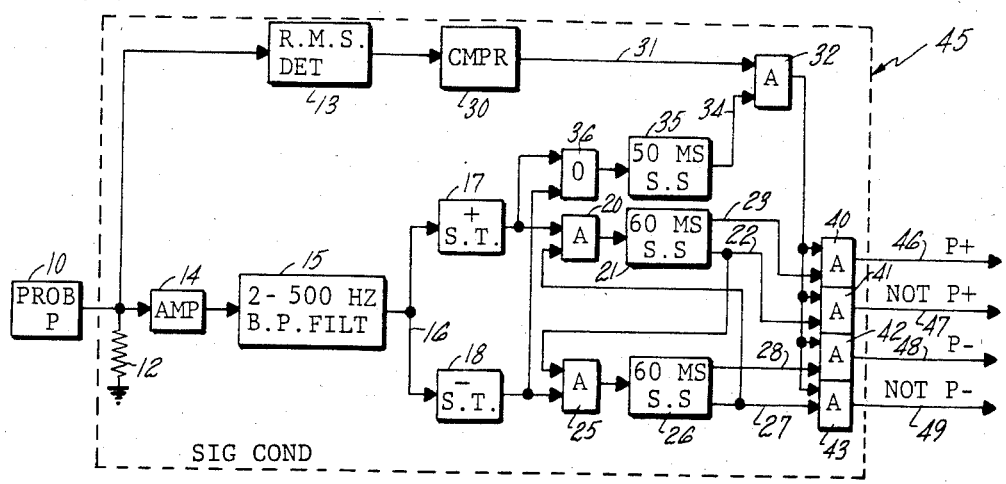
Figure 88:
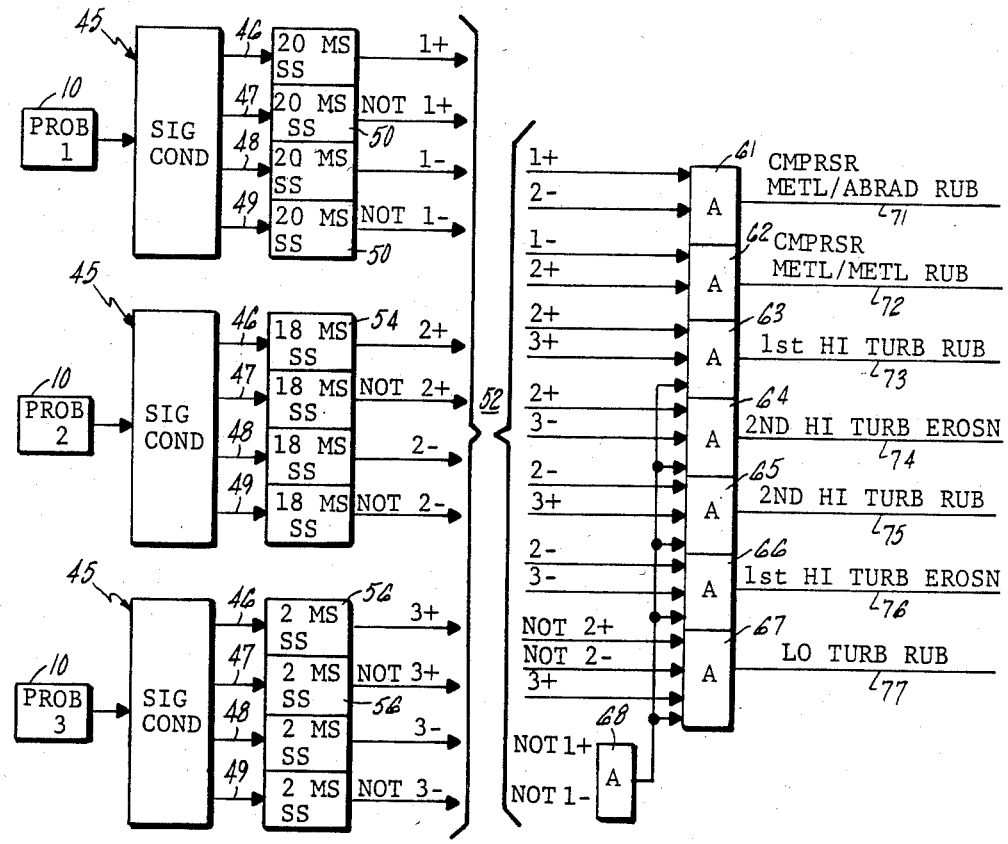

The following are logic flow diagrams of a second digital embodiment of the invention:

FIG. 83—data acquisition interrupt;
FIG. 84—fault;
FIG. 85—correlation;
FIG. 86—distress analysis;

FIGS. 87 and 88 are simplified schematic diagrams of a simple analog embodiment of the invention.

BEST MODE FOR CARRYING OUT THE INVENTION

DIAGNOSTIC SYSTEM—FIG. 1

Figure 1:
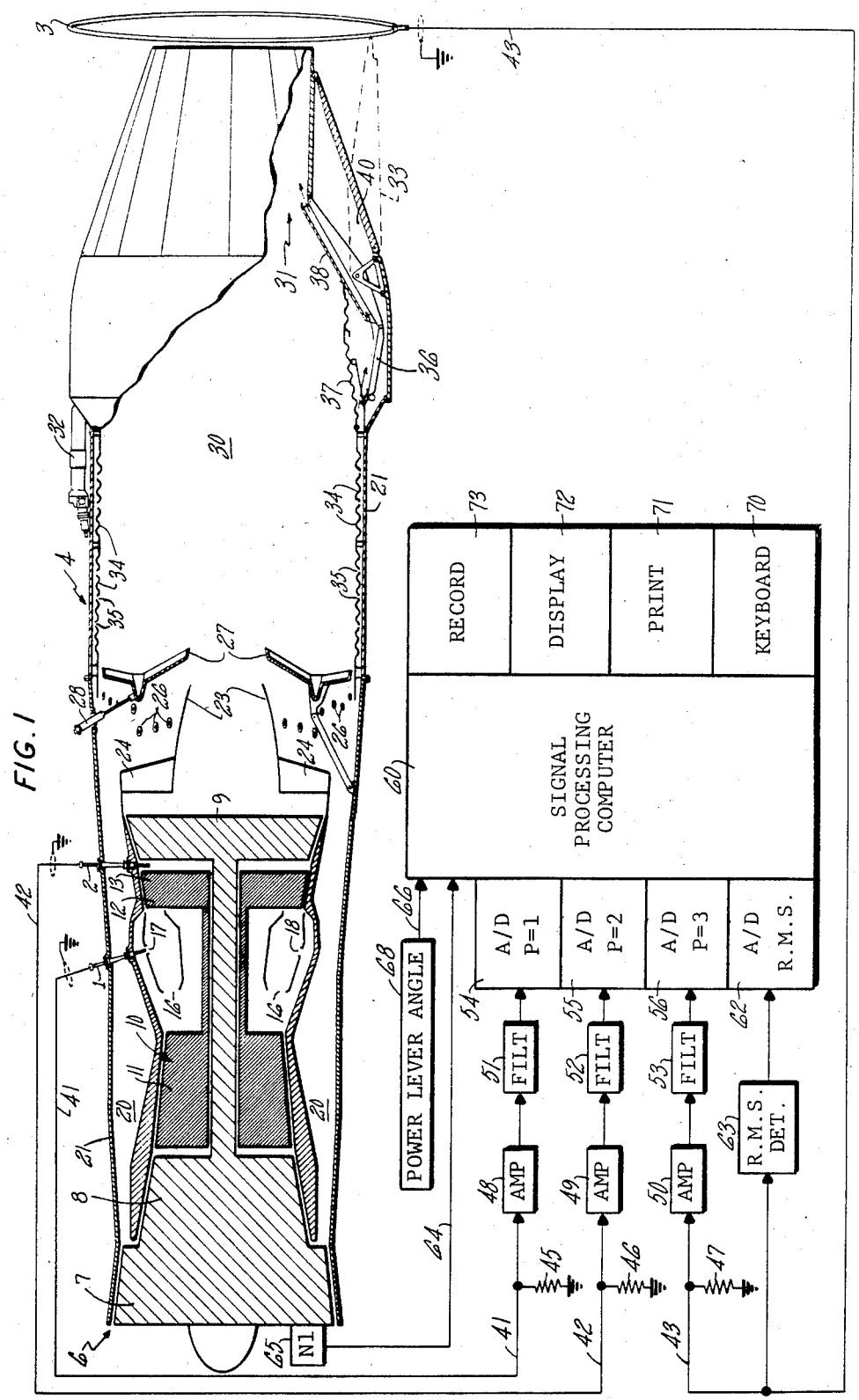
FIG. 1 is a simplified, sectioned side elevation view of an afterburning gas turbine engine together with a simplified schematic block diagram of electrostatic engine diagnostic apparatus attached thereto, in which the present invention may be implemented.

Referring to FIG. 1, a plurality of probes 1, 2, 3 are disposed for response to electrostatic charge in the gas stream of an afterburning gas turbine engine 4. The engine 4 is shown in an simplified fashion for illustrative purposes only; the invention may be utilized as well with engines which do not have an afterburner, or engines with slightly different characteristics than those implied by the description herein. As shown, the engine 4 has a low pressure spool 6 including a fan 7, a low pressure compressor 8, and a low pressure turbine 9. A high pressure spool 10 includes a high pressure compressor 11 and a high pressure turbine including first blades 12 and second blades 13 (downstream of and separated from the first blades 12 by vanes, not shown). The probe 2 is inserted at the vanes between the high pressure turbine blades 13 and the low pressure turbine 9. The engine includes an annular burner can 16 having dilution air inlet holes 17, 18 therein, the probe 1 being inserted with its tip in the dilution air inlet hole 17. The core engine 6-17 is surrounded by an annular fan duct 20, the outer wall of which is the engine wall 21. An exhaust cone 23 is supported by suitable struts 24. A plurality of spray rings 26 (shown only schematically herein) provide fuel mist to the afterburner of the engine, the essential part of which is a flameholder 27 coupled with an igniter 28. The tail pipe of the engine 30 includes a variable nozzle 31 which is shown in the closed position herein, but which when moved by actuators, illustrated by an actuator 32, can assume the position shown by the dotted lines 33. The tail pipe 30 has an afterburner liner 34 with a plurality of cooling air outflow holes 35 therein; fan air enters between the liner 34 and the engine wall 21 in the vicinity of the flameholder 27 to cool the engine wall and avoid burnthrough. One of the tests herein is determining erosion of the nozzle liner 34. The cooling air continues to flow aft between a balance flap 36 and a movable nozzle liner extension called a balance flap seal 37 which makes rubbing contact with a balance flap link 38 under which the air flows. Several tests described hereinafter are related to rubbing of the seal 37 which precedes a burnthrough thereof that allows the hot afterburner gases to proceed from the tail pipe 30 into the spaces 40 beneath the plate 39, causing nozzle damage.

Each of the probes 1-3 is connected by a suitable conductor 41-43, which may preferably be coaxial cable with grounded sheaths, to respective terminating impedances 45-47 which may be on the order of 100 kilohms, although the impedance 47 related to the probe 3 may be somewhat smaller, in some cases, in dependence upon the particular manner in which the present invention is utilized. As electrostatic charge passes by any of the probes 1-3, depending upon the polarity of the charge, current flows into and out of the probe, causing corresponding voltages across the impedances 45-47. The voltage developed across the impedances 45-47 are fed to corresponding amplifiers 48-50, the outputs of which are fed to corresponding filters 51-53 to have the high frequency, high voltage Trichel pulses, and other noise signals eliminated. The filters preferably are band-pass filters having an upper cut-off frequency on the order of about 600 Hz, although cut-off in the range of 400 to 1,000 Hz are suitable. The filters may have a lower cut-off frequency of 1-5 Hz, to eliminate some drift and other D.C. phenomenon in the waveshapes being examined. In fact, the exemplary waveshapes described herein and illustrated by the exemplars of FIGS. 57-80 were achieved utilizing band-pass filters having a sharp cut-off at 490 Hz.

Each of the filters 51-53 feeds a corresponding analog-to-digital (A/D) converter 54-56 connected with a signal processing computer 60. As described more fully hereinafter, the A/D converters are operated to sample the filter outputs (the probe signals) once about every millisecond, the A/D converters being read in rapid succession, within about 10 microseconds of each other. However, the exemplary waveforms illustrated in FIGS. 57-80 herein were obtained by sampling at a 1.3 KHz rate. And the parameters given for use in various subroutines to discriminate the various waveforms from each other set forth in Tables 2-9 hereinafter are related to the utilization of the 1.3 KHz rate, there being 26 historical samples prior to the sample which crosses a threshold (as described hereinafter) in a 20 millisecond history period and 77 additional samples across a 60 millisecond post threshold crossing interval, totaling 104 samples in an 80 millisecond record which each of the waveshapes of FIGS. 57-80 comprise.

For pockets of sufficient charge to be of interest, current in the probe 1 may be on the order of 0.10 microamperes; current in the probe 2 may be on the order of 0.20 microamperes; and current in the probe 3 may be on the order of 2.5 microamperes. Within impedances of about 100 kilohms, the gain of amplifiers 48 and 49 may be about 100, and the gain of amplifier 50 may be about 10. This results in signals of interest of between one and ten volts, with an occasional higher signal. The D/A converters need only respond to 10 volts, any saturation from higher voltages being unimportant. With the aforementioned gains, thresholds (described with respect to FIG. 8, hereinafter) may be 1 volt for probe 1, 2 volts for probe 2 and $2\frac{1}{2}$ volts for probe 3, if fixed thresholds are used. This, of course, will vary depending on how the invention is utilized. If desired, the impedances and voltage scaling can be changed to suit different A/D converters.

The signal processing computer 60 may also have an R.M.S. A/D 62, the input of which is a conventional R.M.S. detector 63 which is connected to the probe 3 because probe 3 has no contact with the engine exhaust, and therefore has no D.C. component and very low noise, as described in the aforementioned Couch application, Ser. No. 432,507. The R.M.S. detector preferably includes, or is fed by, an isolation amplifier (not shown). As described hereinafter, R.M.S. noise is utilized in the present embodiment as an indicator of a normal wear interval. The signal processing computer 60 may also have an engine speed input on a line 64 provided by a tachometer 65 responsive to the low pressure spool 6 (N1). In the present embodiment, the engine speed signal is used to provide an acceleration variation of threshold. The signal processing computer 60 may also be provided with a signal on a line 66 provided by a power lever angle transducer 68. In the present embodiment, this simply provides historical information to accompany the data which is otherwise acquired and analyzed. The signal processing computer 60 may have conventional input/output devices attached thereto in order to derive the useful information provided thereby: these may include a keyboard 70, a printer 71, a display unit 72 and a recording device 73, such as a magnetic floppy disc or a magnetic tape cassette, or the like, as desired. If the invention is utilized in an airborne environment (necessitating use of a different probe than the hoop probe 3), the conventional input/output devices 70-73 would not be used; instead, a nonvolatile storage module would be used to collect data in the air, the content of which would be displayed and analyzed in ground-base signal processing apparatus.

The signal processing computer 60 may be selected from a wide variety of commercially available signal processors. Such computers may be as small as an Intel 8080, or may be larger, such as the Texas Instruments 9900 series. Or, in dependence upon the speed and amount of information which is desired to be retained during any given operation, a mini-computer such as a Digital Equipment Corp. PDP/11 series may be used. Of course, any larger computer may be used if desired. Or, two microprocessor C.P.U.s may be used: one for data acquisition and one for data waveform classification and/or analysis. The particular nature of the particular computer used, the input/output equipment disposed thereon, sampling rates and other things can be varied to suit any implementation of the present invention, utilizing readily available hardware and suitable common programming techniques, which are well within the skill of the art in the light of the teachings which follow hereinfter.

In the description which follows hereinafter, it should be understood that various features set forth and claimed in other commonly owned, copending U.S. patent applications are disclosed. These are disclosed herein for simplicity in illustrating the best mode of the present invention, which may be utilized in conjunction with such other features, and for simplicity in presenting the manner in which the other features may be incorporated herewith. However, the present invention relates to the discrimination by waveshape of electrical signals produced by electrostatic effects in the engine gas stream, and which correlate in major part with known events or conditions of the engine.

Abbreviations, some or all of which are used herein, are set forth in Table I.

TABLE I

| | |
|---|---|
| A/B = afterburner | MEASRD = measured |
| ABNORML = abnormal | MIN = minimum |
| ABSNT = absent | MULT = multiple |
| ACEL = acceleration | NEG = negative |
| A/D = analog-to-digital | NOMNL = nominal |
| ADV = advance | OPOS = opposite |
| BEG = beginning | P = PROB = probe |
| BUF = buffer | PARAM = parameter |
| C = CAT = category | PK = peak |
| CLAS = classification | P.L.A. = power lever angle |
| CONECTR = connector | POST = post-pulse |
| CROS = CROSNGS = crossings | PRE = pre-pulse |
| CTR = counter | PRIM = primary |
| DECEL = deceleration | PROG = progress |
| DECR = decrement | PTR = pointer |
| DGRD = degrade | PULS = pulse |
| DGRDN = degradation | Q = quality factor |
| DIF = difference | R = RCRD = record |
| DISTRS = distress | RDY = ready |
| DVSR = divisor | REQ = request |
| ENBL = enable | REVRS = reverse |
| ENG = engine | R.M.S. = root-mean-squared |
| EXP = exponent | RSLTS = results |
| FLG = flag | RST = reset |
| FOLWNG = following | S = SAMPL = sample |
| FXD = fixed | SENSTVTY = sensivity |
| G = group | SEPRATN = separation |
| HI = high | SIN = sign |
| HISTRY = history | SPD = speed |
| INCR = increment | SQRT = square root |
| INIT = initialize | STR = store |
| INTGRL = integral | STRT = start |
| INTVL = interval | TACH = tachometer |
| IRPT = interrupt | THRSH = threshold |
| LIM = limit | V = value, volts |
| LO = low | VARIATN = variation |
| MAX = maximum | ( ) = of; or grouping |

PROGRAM STRUCTURE—FIG. 2

Figure 2:
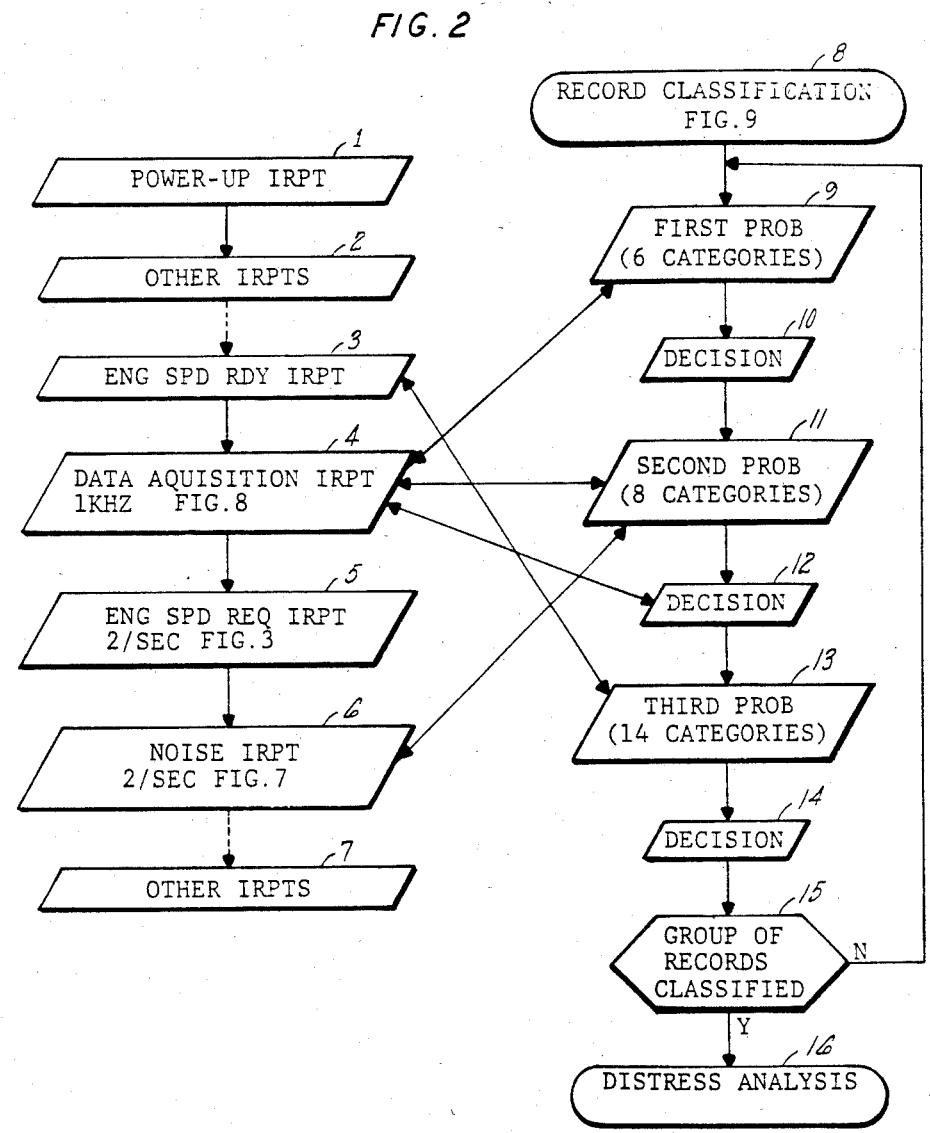
FIG. 2 is a simplified, logic flow diagram of a program structure which may be utilized in programming a suitable data processing system for implementing the present invention.

Referring now to FIG. 2, a simplified illustration of an exemplary program structure for acquiring and classifying data provided from the probes 1-3 disposed for response to the engine includes utilization of interrupts to acquire data and utilization of background programs (which may be interrupted for data acquisition) for classifying, analyzing, and correlating the data. The program structure is exemplary merely, and other structures may be utilized in dependence upon the size and type of data processing system used to implement the present invention. Typically, systems are initialized on power-up by a power-up interrupt routine 1 which is automatically reached by the highest ordered interrupt in an interrupt priority scheme. Other interrupts 2 may be utilized, such as for sending and receiving data to auxiliary storage devices (such as cassettes and floppy discs) or sending data to a printer. Then a medium priority interrupt 3 may reach an engine speed ready interrupt program to read engine speed, as described more fully hereinafter with respect to FIG. 4. A next higher order interrupt 4 may reach a data acquisition interrupt program for actually reading the data from the probes disposed with the engine, as described more fully hereinafter with respect to FIG. 8. And an interrupt 5 of a relatively lower priority may reach an engine speed request interrupt program, for initiating the reading of engine speed, as described with respect to FIG. 3 hereinafter. A relatively still lower priority interrupt 6 may reach a noise interrupt program for reading R.M.S. noise on one of the probes, as is described more fully hereinafter with respect to FIG. 7. Then, other interrupts 7 of still lower ordered priority may be utilized such as to control tape transport real time delays and to handle display and keyboard character exchange. All such other interrupts are those which will suit any given implementation of the invention, in dependence upon the particular system in which the invention is embodied and the design requirements thereof.

In FIG. 2, as an example only, a record clasification program, described in detail with respect to FIG. 9, is called on a regular basis, and is actually performed whenever records have been accumulated to be classified and the classification has not yet been done (as described hereinafter). Briefly illustrated is the basic units of the record classification program of FIG. 9. For instance, the record classification program 8 includes a first probe subroutine 9 which compares a sample record with five categories of signals, following which a decision subroutine 10 determines which of the five categories (if any) is likely to have been the one which occurred in the engine. Then a second probe subroutine 11 examines a record against the characteristics of seven categories and a decision subroutine 12 determines which of the seven categories is likely to have occurred in the engine. A third probe subroutine 13 examines the records from the third probe against characteristics of fourteen different categories and a decision subroutine 14 determines which of the fourteen categories (if any) is likely to have occurred in the engine. The process set forth illustratively with respect to the subroutines 9–14 is repeated until an indication 15 is provided that an entire group of records has been classified. Then, a distress analysis program 16 may be called to provide further, post-classification processing in a manner described more fully hereinafter with respect to FIG. 9 hereinafter. Thus, as record classification and distress analysis are being performed, acquisition of probe data, engine speed and noise continues by means of interruption of the record classification and distress analysis programs.

ENGINE SPEED—FIG. 3., FIG. 4

Referring now to FIG. 3, an engine speed request interrupt is issued on a real time basis, such as twice per second. This reaches an engine speed request interrupt program through an entry point 1 in FIG. 3. A pair of steps 2 cause an engine speed counter to be reset to all zeros and a tachometer I/O request to be issued. Then, a test 3 determines when the tachometer I/O has acknowledged the request with a handshake, and when it does, an affirmative result of test 3 reaches a pair of steps 4 in which a speed timer is started and the engine speed ready interrupt is enabled (if required). Then the program ends at point 5 and the program which was interrupted (if any) is resumed through ordinary, interrupt handling processes. When the speed timer started in steps 4 of FIG. 3 reaches a predetermined count (across which tachometer pulses are counted by the engine speed counter which was reset in steps 2), the speed timer will then issue an engine speed ready interrupt.

In FIG. 4, the engine speed ready interrupt reaches an engine speed ready interrupt program through an entry point 1. In a series of steps 2, the engine speed information is processed so as to provide a voltage threshold for one of the probes (such as the third probe in the present embodiment) which includes a component related to engine speed. In the steps 2, new engine speed (designated by "n") is set equal to the engine speed counter. The faster the engine was going, the higher the count. Then engine acceleration is determined by subtracting the old engine speed (designated by "m") from new engine speed. Then the threshold for the third probe is provided by multiplying the absolute value of engine acceleration (so as to be positive during either acceleration or deceleration) by some constant, and adding it to a fixed threshold value which is otherwise appropriate for that probe. Then the old engine speed is updated by making it equal to the new engine speed. Engine speed (or the preceding sequence of speeds) can also be recorded as one of the parameters in a record indicative of an event in the engine, as described hereinafter. This poses no problem since the new value of engine speed can be reached in a steady condition (not changing from old value to new value) at all times other than during the engine speed ready interrupt. When the steps 2 have been performed, the program is ended through an exit point 3. Then, any program which was interrupted by the engine speed ready interrupt is reverted to through ordinary interrupt handling processes. Engine speed may alternatively be derived using automatic hardware apparatus, rather than a clocked interrupt.

ILLUSTRATION OF DATA ACQUISITION—FIG. 5, FIG. 6

The manner in which the data acquisition interrupt 4 of FIG. 2 acquires samples from the probes is illustrated briefly at the bottom of FIG. 5. In FIG. 5, each of the probe A/Ds is interrogated once about every millisecond. During acquisitions of the data, the A/Ds for the successive probes are read in the order: probe 1, probe 2, probe 3. These are read as quickly as they can be (as closely as possible together) so that the data samples (1–104 in the present embodiment example) will relate very closely to the same time frame and therefore have correlative meaning. A sample rate on the order of 1000/second (1 millisecond between samples) has been found to be acceptable. This leaves approximately 750 milliseconds for processing (such as record classification and the like) as described with respect to FIG. 2 hereinbefore, between the sampling of triplets of data from the probes. As each probe is sampled, the digital value indicative of the magnitude of signal on the probe (illustration (f), FIG. 6) is stored in a corresponding, successive location in a portion of storage referred to herein as a history buffer (illustration (e), FIG. 6). The history buffer may have the capacity to hold 32 or 256 (or some other number of) triplets of data as illustrated in the bottom of FIG. 6. Therein, the data samples for probes 1–3 are indicated as having been stored in positions of the history buffer arbitrarily identified as numbers 31 through 62. The reading of data from the A/Ds into the history buffer goes on continuously, without regard to whether or not thresholds have been exceeded. When the history buffer is full, the corresponding history buffer pointers (one for each probe) simply cycle around to the lowest address thereof and continue to overwrite data in a cyclic manner. This data is of no significance except in the event that the value sensed on one of the probes exceeds the threshold for that probe; a threshold exceedance at any one of the probes causes the last 27 samples for all of the probes to be moved from the history buffer (illustration (e) of FIG. 6) into the record buffer (illustration (d) of FIG. 6). The record buffer is shown in an expanded format, and illustrates that 104 samples and other data relating to each probe, as well as additional data such as speed, power level angle and time, may be stored in each record which results from each threshold exceedance by any one of the three probes. The sample value number (1–29 . . . 104) thus becomes known only once a threshold is exceeded by the data sensed on one of the probes. The bottom portion of illustration (d) of the record buffer shows an exemplary complete record, identified as record number 61 in the middle portion of illustration (d) in FIG. 6. Capturing a complete record, whenever an event occurs in the engine as sensed on any one of the three probes, does not necessarily result in utilization of any of that data. This is because events occur occasionally even in a healthy engine, so analysis of the particular event is not necessarily an indication of abnormal engine wear. Instead, abnormal wear is indicated by the occurrence of some large number of threshold exceedances (such as ten times a normal number) within a given wear interval of time (which may be a fixed or variable interval of time). In the present embodiment, the wear interval is variable and is dependent upon the average value of R.M.S. noise on one of the probes at times other than when an event is occurring, as is described more fully with respect to FIG. 7 hereinafter. In the present embodiment, "M" is determined to be ten times the normal number of threshold exceedances which should occur during a wear interval in a healthy engine. This number may be, for instance, on the order of 20 or so. The value "N" is taken to be some arbitrary number of additional records, following the occurrence of ten times normal wear, which may be taken so as to complete a classification group of records to provide an indication of what sort of abnormal wear has occurred. In the present embodiment, N may be on the order of ten or so. As shown in the middle of illustration (d) of FIG. 6, a group of records is composed of M+N records numbered 60 through 90 totaling thirty records and comprising group 2. Groups 1–4 of the record buffer are shown in the upper portion of illustration (d). These groups of records are stored away in a fairly substantial record buffer which may contain on the order of 64 or 256 records. Depending upon the particular manner in which the present invention is utilized, records may be accumulated until the record buffer is full, after which no more records are taken. Or, the record buffer may be operated in a cyclic fashion (as described with respect to the history buffer hereinbefore) so when the maximum address for the highest group of records is reached, the pointers (R, R') which keep track of the record buffer revert to zero and begin to walk through the record buffer a second time. In the present embodiment, a cyclic record buffer of a suitable size is presumed to be desirable and provisions are made to prevent records from being overwritten until the data content thereof has been analyzed. In such a case, the results of analysis for any particular group of records may be stored in a group results portion of storage as shown in illustration (a) of FIG. 6. The amount of storage required to store the overall processed results for each group is extremely small compared to all of the sample records in each of the groups, and therefore a significantly large number of group results can be stored with relatively small amount of storage. In other embodiments, the classification may be done either off-line or in separate equipment (such as when data is collected by an airborne data acquisition unit and processed in a ground based classification unit). In such a case, the record buffer is preferably comprised of a nonvolatile storage, and when the record buffer is full with some reasonable number of groups of records, acquiring of further records ceases, as described more fully hereinafter. Other aspects of storage which are illustrated briefly in FIG. 6 are described hereinafter.

In FIG. 6, the groups 1-4 of records are shown as stored contiguously in the record buffer. However, the present embodiment retains records only in the event that M records occur within a wear interval. If a fewer number of records occur during a wear interval, this is taken to be normal wear and not worthy of being recorded. However, it cannot be known whether or not M records will occur during the wear interval until M number of records have been collected prior to completion of a wear interval.

Referring to the top of FIG. 5, four groups of M+N records are shown. The first group of records was started at some arbitrary point within the first wear interval. Since M records were accumulated before the end of the wear interval, a distress threshold (M) was exceeded and N more records were accumulated, even though some of these were accumulated in a following wear interval. At the time that M1 set of records were completed, the M counter was reset and additional records are collected in the N1 set; these records are also designated (simply by the mechanisms described hereinafter) as being applicable to the second group of records. But just after starting to collect the second group of records, the end of the first wear interval caused resetting of the M counter again so that counting of M records commenced anew (designated M2' in FIG. 5). Some of these records are the same records as are utilized in group 1 as well. Eventually M2' reaches the distress threshold and M is reset once again. The N2 set of records are collectd to finish the second group of records and some of these records are designated for the third group as well (M3 in FIG. 5). But before a distress threshold is reched for the third group, the end of the second wear interval occurs and resets the M counter again. Thus the taking of records for the third group of records commences anew at the begining of the third wear interval. As it were, the entire third wear interval did not have sufficient records to exceed the distress threshold in the example of FIG. 5, so the M counter is reset again at the end of the third wear interval. Beginning the the fourth wear interval, another set of M records is started for the third group (M3"). In the example of FIG. 5, apparently a large amount of activity occurs during the fourth wear interval so that M records are collected early in the interval and a fourth group is started. The third group is completed and M records for the fourth group are completed prior to the end of the fourth interval so that in fact two groups are completed mainly within the fourth wear interval.

Notice that the wear intervals are not of the same time duration: that is because in the present embodiment the wear intervals are determined by R.M.S. noise of the engine. Since the electrostatic noise effluent in an engine is very closely a linear function of engine wear, this provides a manner of indicating how much activity should occur in a given period of time to separate normal activity from abnormal wear activity.

In FIG. 5, notice that when the N sets of records to complete a group have been taken, this does not affect the allocation of some of those records to an M set for a following group. Notice also that the M counter is reset so as to start a new count at the end of each wear interval, but the records collected thereafter will be for the same group of records that has just been terminated. On the other hand, whenever a distress threshold is exceeded (that is M, number of records have been collected) not only is the M counter reset so as to start a new group, but N more records are collected for the current group. The time interval required for M or N thresholds is also variable, depending on how much activity there is in the engine. This is illustrated best in FIG. 5 by comparison of the third and fourth interval wherein much activity occurred in the fourth interval so that two records could be designated while at the same time insufficient records were created in the third interval so as to declare a record.

R.M.S. NOISE, WEAR INTERVAL—FIG. 7

Referring now to FIG. 7, the reading of R.M.S. noise from one of the probes and the provision of an R.M.S. noise wear interval (and accommodating the consequences thereof) is illustrated in an exemplary fashion. The noise interrupt 6 of FFF. 4 reaches the noise interrupt program of FIG. 7 through an entry point 1 and a first pair of tests 2, 3 determine if a record is in progress or not. If a record is in progress, it is because one of the probes has had a threshold exceedance within about 70 milliseconds of the noise interrupt. The threshold exceedance, being an abnormal event, is not indicative of ordinary R.M.S. noise currently in the engine. Therefore, a reading of R.M.S. noise is not made in the case where a record has been initiated or is still in progress as indicated by the tests 2, 3. But whenever a record is not in progress, negative results of steps 2 and 3 in FIG. 7 will reach a step 4 wherein the R.M.S. A/D 62 is started. Then a test 5 determines when the R.M.S. A/D is complete so that an R.M.S. value can be stored in a step 6. Whenever a record has been initiated or is in progress, the R.M.S. value previously stored in step 6 is not disturbed due to bypassing thereof by affirmative results of either test 2 or 3.

In FIG. 7, a step 7 provides an R.M.S. increment as the difference between the stored R.M.S. value and some R.M.S. threshold. The R.M.S. threshold is a value of electrostatic noise at the probe (e.g., the hoop, probe 3 in this embodiment) which is very low, and indicative of the normal noise level during low thrust operation of a healthy engine. The R.M.S. threshold can be chosen as being some value of R.M.S. noise which is sufficiently low that the contribution it would make (during a half-second of time) can be ignored completely in the R.M.S. interval. This makes a wear interval dependent only on excessive R.M.S. noise which therefore is more sensitive to current engine conditions. Thus if an engine has a relatively high normal noise level, the wear intervals need not necessarily be unduly short, thereby causing an excessive amount of uninteresting data to be accumulated; instead, the R.M.S. threshold for reading that particular engine can be raised, thereby providing a meaningful wear interval based on R.M.S. noise, even though R.M.S. noise (at a given power level) may vary considerably from one engine model to the next (or even from engine to engine of the same model), which is not likely. In FIG. 7, if the R.M.S. noise is greater than the threshold, an affirmative result of test 8 will reach the step 10 in which an R.M.S. integral is incremented by some constant times the R.M.S. increment. This is a typical integration function, except for the fact it is only performed if the R.M.S. noise exceeds the R.M.S. threshold.

In FIG. 7, the R.M.S. integral is compared against some basic wear interval in a step 12. The wear interval is not a unit of time, but rather a unit indicative of a variable period of time within which the engine will exert a certain amount of work (power for a period of time), in relation to the total work the engine may exert during normal engine life. The interval corresponds to a short flight or a half-hour test; ideally, it represents about three cycles of start-up, advance to maximum power, and shut down. The wear interval is described in terms of power and cycling in the aforementioned Couch article. During the variable wear interval, a given engine will have a normal amount of activity, such as the collection of two records (two events resulting in threshold exceedance), whereby the collection of ten times that number of records (such as 20) will be indicative of abnormal wear. If the R.M.S. integral has not exceeded the wear interval value therefor, a negative result of test 12 will reach the program end at a point 18. Similarly, if test 8 determines the increment to be negative, the subroutine not only bypasses step 10, but it bypasses the remaining steps since the wear interval (having not been exceeded in a prior pass through the subroutine) could not be exceeded with the unchanged integral. However, whenever the R.M.S. noise has integrated to a point where it exceeds the wear interval, an affirmative result of test 12 will reach a series of steps 13 in which the M counter is set equal to zero and an I pointer is incremented. The I pointer incremented in step 13 of FIG. 7 is utilized as an address component for distress counters in storage which are shown in illustration (b) of FIG. 6. As decribed more fully hereinafter, a threshold exceedance in the positive direction or in the negative direction for each of the probes connected with the engine is counted separately during each wear interval, and these counts may be saved as an indication of the temporal spectrum of wear which occurred (without regard particularly to what caused it in the general case) during the operation of the engine. Thus, in the course of forty hours of flying time, patterns of excessive wear indicated only by these counters will generally show increases in count in a sustained fashion within a period of time (e.g., tens of hours) just before severe engine distress could otherwise be noticed, such as by adverse operation, borescope inspection or the like.

In FIG. 7, a test 14 determines whether a distress flag has been set or not, described more fully hereinafter; the test 14 relates to whether or not M records have been sensed within a single wear interval, as is described with respect to the top of FIG. 5 hereinbefore. If M records have been collected during the wear interval, (such as at the end of interval 1, interval 2 and interval 4 in FIG. 5) then the first record in the next group (such as M2' in FIG. 5) will begin at the point in the record buffer where records are now being stored. Thus an affirmative result of test 14 will reach a step 16 wherein a temporary pointer (called Begin M) is set equal to the current value of an R pointer that keeps track of records being stored in the record buffer (illustration (d), FIG. 6). On the other hand, if distress has not been indicated (the distress threshold M not having been exceeded), different operation occurs. This is the case illustrated at the end of the second and third wear intervals at the top of FIG. 5. At the end of the second wear interval, the record buffer has been filled with M2' and N2' and thus storing of new data not related to the second group should begin at the end of the second group. But, the record buffer has been filled with some number of records designated as X.S. in the top of FIG. 5 which are of no value since they did not amount to an excessive number within the wear interval. These may be thrown away and therefore they may be written over by the third group. Therefore, the designation of the point in the record buffer where the third group of records may occur is a lower address number than the current address being used in storing of M3, at the end of the second wear interval.

With these factors in mind, a series of steps 17 in FIG. 7 will cause an R decrement to be generated equal to the difference between an R pointer and an N pointer. The R pointer is the current address being used to store the M3 records at the end of the second interval. The N pointer is a saved address indicative of the last address utilized in storing the N2 records of group 2. This allows sliding the record buffer address back so that the third group can be contiguous with the end of the second group. Then an R counter (a count which continues upwardly, rather than recycling back to a low address value as the R pointer does) is decremented by having the R decrement subtracted therefrom. The R pointer is then updated to equal the N pointer, thereby causing the address for the first record of the third group to be next higher than the address of the last record of the second group. And the beginning address for the particular group of records is recorded as being equal to the R pointer. Then the noise interrupt program of FIG. 7 ends at point 18, and any other program which had been interrupted thereby is returned to utilizing ordinary interrupt handling processes.

DATA ACQUISITION—FIG. 8

Referring to FIG. 8, a real time interrupt, once each millisecond, causes the sampling of all of the probes on the engine at the one kilohertz data acquisition rate. Ideally, the probes will be sampled simultaneously. But, hardware constraints, such as use of a single multiplexed A/D, or a single A/D bus system, may require successive sampling. In this embodiment, during each interrupt, all of the probes are sampled about one-tenth of a millisecond apart from each other. The data acquisition interrupt is reached through an entry point 1 in FIG. 8, and a first test 2 determines whether data acquisition operation has been initiated or not. Upon initial power-up, a negative result of test 2 will cause a series of steps 3 to: reset a group counter (G) to "one" (indicating that there has not as yet been collected a first group of threshold-exceeding samples indicating ten times normal wear); reset a group counter (G') to one (indicating that a first group of records has not yet been classified); reset a record pointer (R PTR) to "one" (indicating that the first record is about to be made as a consequence of one of the probes having a signal magnitude in excess of the record threshold); set a probe pointer (P) to the highest-numbered probe (3 in the present embodiment) so that when advanced, the probe pointer will be pointing at the first probe; set $I = 1$ (indicating the first wear interval is about to start); reset M and N to zero; and set the initialize flag. In all passes through data acquisition interrupt program of FIG. 7, subsequent to the first pass on power-up, the results of test 2 will be affirmative, thus bypassing the initializing steps 3.

Routine Sampling of Data

Once initialized, the iterative steps of the data acquisition interrupt program continue with steps 4 in which the P pointer is advanced and the A/D for probe P is started, after which a test 5 determines whether the A/D converter related to the probe identified by P pointer has completed the conversion, or not. The program hangs up on test 5 until the A/D converter for the P probe is complete, after which an affirmative result of test 5 reaches a series of steps 6 in which the A/D converter for the next probe (one in advance of probe P) is started, the history buffer for probe P has stored in it the A/D results from the A/D converter for probe P, and the history buffer pointer (designating the particular part of the cyclic history buffer) for probe P is advanced. The history buffer for each probe may be of any desired size, but in the example herein they must have at least 27 sample storage locations each, since the records of the present embodiment include 27 samples of history along with 77 samples which are captured on-the-fly following a threshold exceedance. Thus any available memory locations may be utilized as history buffers by means of address portions relating to the history buffer as a whole, address portions relating to the particular probe involved, and address portions corresponding to the history pointer for the particular probe (the probe's portion of the history buffer).

In FIG. 8, for each sample read into the history buffer in the steps 6, a test 7 determines whether a record is already in progress or not. If not, a negative result of test 7 reaches a test 8 which determines if a record has been initiated or not. The initiation of a record, as described below, occurs whenever a threshold is exceeded (on any one of the probes) for the first time following the completion of a previous record. A negative result of test 8 will reach a test 9 which determines if the last sample to be read exceeds the negative threshold for this probe, or not. If not, a test 10 determines if the most recent sample exceeds the positive threshold for this probe. If the most recent sample does not exceed the record threshold in either the positive or the negative direction, negative results of tests 9 and 10 combine to reach a test 11 to see if the third probe has been read during this iteration. If not, a negative result of test 11 returns the program to step 4 to cause reading of the next sample, and starting the A/D converter for the sample following the next sample. When all three probes have been sampled, an affirmative result of test 11 will reach a test 12 to see if a record has been declared. Since threshold exceedances only occur some tens of times per million interrupts, usually no record is declared and a negative result of test 12 reaches the program end point 14.

In cases where none of the samples exceed the threshold, passage through steps and tests 4–11 three times, (with the A/D converter for each probe being read once and the results thereof stored in the corresponding history buffer for the probe) and ending through test 12 is all that occurs. This can go on virtually indefinitely in subsequent passes through the data acquisition interrupt routine, so long as no threshold is exceeded. In such a case, all that occurs is that data is stored in the history buffer in a cyclical fashion. When each history pointer reaches maximum and returns to a minimum setting, the newly incoming data will simply be overwritten over the oldest data in the history buffer, in a cyclical fashion.

Declaring a Record

Eventually, one of the three probes may provide a signal in excess of its record threshold so that one of the tests 9, 10 in FIG. 8 will be affirmative. It does not matter which of the three probes does this; in any event a record is declared as a consequence of one of the three probes having a signal in excess of either its positive or negative threshold. In such a case, an affirmative result of test 9 will cause a step 15 to increment the negative distress counter for probe P within the current alarm interval (I) storage area. Or, an affirmative result of test 10 will cause a step 16 to increment a positive counter. Then, a series of steps 18 will record the source of the exceedance as the current probe, store the current threshold values for all three probes, and set the record initiated flag. If the first or second probe caused setting of the record initiated flag in steps 18, test 11 will again be negative so the program will return to step 4 until all three probes have been read during the present cycle. Once all three probes have been read, then tests 11 and 12 will be affirmative causing the program to advance to a test 19 to ensure that storage of a record at R in the record buffer will not write over a record that has not already been classified. In test 19, R Max is the total number of records that can be stored; the R counter keeps track of how many have been stored; and the R' counter keeps track of how many have been classified (and analyzed, if post classification analysis is utilized). If the buffer is full, a negative result of test 19 will reach a step 20 which resets the record initiated flag, thereby causing the record to become undeclared. If the buffer is not full, an affirmative result of test 19 reaches a series of steps 21 which initialize moving the history buffer for one of the probes to the record buffer for that probe.

Moving the History Data

Specifically, in steps 21, the P pointer is advanced (so during the first pass it will point to the first probe); the end of the history for the present record for the particular probe is stored as being equal to the current setting of the history pointer for that probe; this memorizes the point at which taking the history from the history buffer and putting it in the record buffer will be complete as described hereinafter; then the history pointer for the present probe is decremented by 26 samples so as to go back to a point in the history buffer which will include 27 samples of the present record (the pulse wave shape to be stored as a consequence of the last triplet of incoming data including one data magnitude which exceeded a threshold). Then in a series of steps 23, one sample of the record buffer for the current record, R (which is initialized as the first record in the steps 3), relating to the current probe, P, is set equal to the sample in the history buffer being pointed to by the history pointer. In the first pass through the steps 23, the first sample of the history buffer for probe 1 is moved into the first sample of the record buffer for probe 1, for the first record. Then the record buffer pointer for probe P is advanced and the history pointer for probe P is advanced. Then, in a test 24, it is determined whether or not all of the history has been moved into the record buffer for this particular probe by comparing the present state of the history pointer for probe P with the maximum history previously stored for probe P. If the complete history has not been moved to the record buffer, a negative result of test 16 causes the steps 15 to be repeated for successively advancing samples of the history buffer and the record buffer. Eventually, all of the history for probe P will have been moved to the record buffer for the first record for the first probe, in which case a negative result of test 24 will reach a test 25 to determine if all three probes have completed movement of samples from their history buffers to their record buffers. Initially, since the first probe has its history moved to the record buffer first, P will equal 1, so a negative result of test 17 will cause the steps and tests 21-25 to be repeated for the second probe and ultimately for the third probe. When the history for all three probes has been moved to the record buffer, an affirmative result of test 25 causes a series of steps 26 to be reached: a sample counter is set to 77 (indicative of the 77 samples of the record for each probe to be taken directly into the record buffer, as well as being stored in the history buffer); and, a record in progress flag is set and the record initiated flag is reset. At the conclusion of steps 26, the end of the program is reached at the point 14.

Capturing the Remaining Record On-The-Fly

In FIG. 10, the next time a data acquisition interrupt occurs, the result of test 2 will be affirmative, bypassing the steps 3 since initialization has already occurred. Once a threshold has been exceeded and a record declared, the next subsequent data acquisition interrupt will cause the routine of FIG. 8 to pass through an affirmative result of test 2 to the step 4 and P is advanced from the third probe to the first probe once again, and the A/D for the first probe is started. As soon as test 5 is affirmative, a series of steps 6 start the next subsequent A/D, store the current sample in the history buffer for the present probe, and advances the history buffer pointer for that probe for use in the next cycle. Now, however, test 7 will be affirmative because there is a record in progress (one of the previous samples having exceeded a threshold).

An affirmative result of test 7 in FIG. 8 reaches a pair of steps 30 in which the record buffer for the first record and the first probe is set equal to the A/D result for the first probe and the record buffer pointer for that probe is advanced for use in a subsequent cycle. Then a test 31 determines if all three probes have been sampled in this particular pass through the data acquisition interrupt program of FIG. 8. If not, the program reverts to step 4 to handle the sample of the next probe in sequence until all three probes have had their A/D samples read into the record buffer, and the record buffer pointer therefore has been advanced. When all three probes are complete, an affirmative result of test 31 reaches a step 32 which decrements the sample counter and then a test 33 which determines if the sample counter has reached zero, indicating that 77 samples subsequent to a threshold exceedance have been stored for all three probes. If not, the program ends at the point 14 for the current interrupt.

Successive data acquisition interrupts cause the program of FIG. 8 to continue to pass through the steps and tests 4–7 and 30–33 until, finally, the sample counter has been decremented from 77 all the way to zero. This indicates that 77 samples have not only been put into the history buffer but have been placed directly in the record buffer as well, for each of the three probes. This means that the record buffer now contains the original 27 samples transferred from the history buffer in steps 21 and 23 and the additional 77 samples taken directly into the record buffer in steps 30. During this time, the history buffer is maintained up-to-date in step 6 so that whenever there is a subsequent exceedance, the history will be available.

Completing a Record

Eventually, when all 77 on-the-fly samples have been stored in steps 30 of FIG. 8, for all three probes, an affirmative result of test 33 reaches a series of steps 35 in which the speed to be recorded with this record is set equal to the current engine speed (FIG. 4); the power lever angle (P.L.A.) for the record is the current value (not shown); the time is the current time; the record pointer (R PTR) is incremented (since a complete record of triplets of 104 samples each has been completed); the corresponding R counter is incremented (this keeps track of the total number of records stored, even after the R PTR reverts to the lowest address); a temporary count (M) of records is incremented (for use as described with respect to FIG. 5); and the record in progress flag is reset. If desired, a history of engine speed over the last 5 seconds or so may be recorded, for print-out with classification results, to aid in subsequent operator interpretation of engine conditions.

Testing for Abnormal Wear

In FIG. 8, a test 36 determines if a distress flag is set (as described hereinafter). Initially it is not, so a test 37 is reached wherein the number of records M (the number of times that a threshold exceedance has recently occurred) is compared against a distress threshold. As described briefly hereinbefore, the distres threshold is preferably taken to be some value on the order of ten times the normal amount of records which may occur in a healthy engine during a given test, flight, or other distress-related interval of time. The distress threshold is set equal to some given number of counts such as 20 or 30 counts. The distress threshold test 37 simply compares the number of records which have been taken since the last indication of distress or since the start of the current wear interval, with the number of records which are indicative of a distress value of wear (a unit of distress). In the case of the first few records taken, the result of test 37 will be negative causing the program to end at point 14.

Thus, as a consequence of having one probe sample exceed the threshold, a record of 104 samples for each of the three probes (along with other data) will have been placed in the record buffer and the record pointer incremented. Then, in a subsequent data acquisition interrupt after completion of the record, data acquisition continues as described hereinbefore. Ultimately, when some number of records indicative of distress have been made because of threshold exceedances, an affirmative result of test 37 in FIG. 8 will reach steps 40 in which a distress flag is set (indicating that the M portion of the record is complete); an N PTR (described hereinafter) is set equal to the current value of the R PTR; and the point where the next M records will be stored is marked by setting BEG M equal to the R PTR. And then the program ends through the point 14.

Completing a Group of M & N Records

As described briefly hereinbefore, once a distress threshold number, M, of records (ten times the normal number of records which should occur in a healthy engine within a given alarm interval) has been collected, an additional number, N, of records is collected to provide a complete classification group consisting of M+N records. To achieve this, data samples are continuously taken as described with respect to steps and tests 4-7 and compared against thresholds to determine if an exceedance requires declaring another record, as described with respect to steps and tests 8-11. When a record is declared, the related (26 prior and one current history) samples in the history buffer are moved to an appropriate portion of the record buffer, and the remainder of the record is taken on-the-fly as described with respect to steps and tests 4-7, and 30-33, hereinbefore. The next time that a record is completed as indicated by an affirmative result of test 33, the steps 35 are performed and test 36 is now affirmative since the distress flag was set in the steps 40 at the completion of the prior record, which was the Mth record for the present group. This causes steps 42 to be reached in which the number N is incremented and an N pointer is advanced. Since the R pointer is advanced in step 35 to be ready for the next record in sequence and the N pointer is set equal to the R pointer in the steps 40, the N pointer initially points to the first of the N subsequent records. The use of the N pointer keeps track of the advancing storage position within the record buffer where the N records are being stored.

In FIG. 8, a test 43 determines if the current, Nth record is the desired maximum number of N MAX records or not. If not, the routine of FIG. 8 ends at point 14. But when the required number of subsequent records is reached, an affirmative result of test 43 reaches a series of steps 44 where N is reset to zero, the designation of the current group, G, is incremented, the beginning record for the current group is identified as the beginning of the M portion of the group, as established either in the step 40 of FIG. 8 or in the step 16 of FIG. 7, as described hereinbefore. And the classification flag for group G is set meaning that group G has to be classified and has not yet been. The distress flag is reset so as to enable collecting a whole new group of records, and distress may be indicated to a pilot or test apparatus operator, as appropriate. Following the steps 44, the routine of FIG. 8 ends at point 14. This leaves the apparatus in condition where it has a group to be classified; however, sampling of the probes on a kilohertz (or so) rate, declaring records when any probe has a threshold exceedance, collecting complete records until a distress threshold number of them have been completed (within the given alarm interval) and adding an additional records thereto to provide a full classsification group, will continue on a real time interrupt basis as described with respect to FIG. 8 hereinbefore. Once a number of thresholds have been exceeded and the corresponding number of records of triplets, containing 104 samples each, for each of the three probes, have been made, the fact that a unit of distress has occurred (exceeding the distress threshold in test 37, FIG. 8) is indicated by the distress flag.

RECORD CLASSIFICATION—FIG. 9

The record classification routine of FIG. 9 is reached on a periodic basis in each pass through the major cycle of the computer, other than during interrupts (as described hereinbefore). Entry of the record classification routine through a point 1 in FIG. 9 reaches a test 2 to determine if classification of the G' group of records is required. If not, the program is ended through a point 3 without performing any further steps in the record classification routine of FIG. 9.

Whenever distress has been indicated and a group (G) of records (M+N in number) have been stored in the record buffer (as described with respect to FIG. 8), but the group (G') has not yet been classified, the record classification routine of FIG. 9 will see an affirmative result of test 2, reaching a plurality of steps 3: the maximum sample is set equal to the maximum sample in a given embodiment (which is established as 104 samples in the present example): a group counter (which counts the records within the current group as they are classified) is set equal to zero; and the record pointer (R' PTR) utilized in record classification (in distinction with that, R PTR, used for data acquisition, FIG. 8) is set to the beginning record of the group of distress records to be classified (the beginning record set in steps 17 of FIG. 7, or in steps 44 of FIG. 8), so that it will point to the first record of the group. This allows the accumulated records to be classified through the program of FIG. 9 interleaved with continuous acquisition of data in new records through the program of FIG. 8, on an ongoing basis, as shown in FIG. 2.

In FIG. 9, the iterative process begins in a series of steps 4 by advancing the R' pointer and incrementing the R' counter and setting the probe pointer, P', equal to the highest numbered probe, which in the present embodiment is three. Then a series of steps 5 advance the P' pointer (so that in the first pass it will point to probe 1), a sample buffer is set equal to the record buffer for the current record and probe (implying a data move of all 104 samples for one probe from the record buffer to a sample buffer used during analysis), a sample counter, S, is set to zero and a category counter, C, is set to zero. (The move of a record for a probe to the sample buffer is not required since all the data may be accessed, when desired, from the record buffer. However, the description is much simpler when reference to R' and P' is not required for each sample.) Then in a step 6, the sample counter is incremented to point to the first sample in the sample buffer. Then a test 8 determines if the absolute value of the magnitude of the first sample (a magnitude indicative of probe output voltage in the present embodiment) exceeds the record threshold for that probe (in general, the same threshold used in tests 9 and 10 and saved in steps 18 of FIG. 8). If not, a test 10 in FIG. 9 determines if all 104 samples have been tested or not. If not, a negative result of test 10 returns to step 6 to increment S and examine the next sample of the record for the particular probe, for threshold exceedance. Assuming that the first probe in the record being examined did not have any signals exceeding its threshold (meaning the record was declared as a consequence of activity on one of the other probes), eventually test 10 will be affirmative following 104 negative results of test 8. This will reach a step 11 where the category (the type of signal) for this probe within this record is set to zero, indicating that there is no record and therefore nothing to be categorized for this probe within this record. Then a test 12 is reached to determine if the samples for all three probes have been interrogated in this record or not. If not, a negative result of test 12 will return to the series of steps 5 in which P' is advanced and a new record of samples for the second probe is brought into the sample buffer from the record buffer, S and C are reset to zero and then step 6 increments S so as to point to the first sample in the record for the second probe. Depending upon whether there is any record at all for this probe, or if this probe has a syntactic pulse shape or is a gross signal, a threshold may or may not be exceeded. If not, the process will repeat through step 11 as described hereinbefore. If there is a threshold crossing as a result of one of the samples having a magnitude in excess of the record threshold for the particular probe, test 8 will eventually be affirmative leading to a step 13 where the sample at which threshold exceedance occurred is set equal to S, the current sample number. Then a test 14 determines if this is the first probe being interrogated or not. If it is, an affirmative result of test 14 will lead to a first probe routine 15 (described hereinafter with respect to FIG. 10) which compares the sample record with characteristics of various categories of signals which can be sensed on the first probe. If test 14 is negative, a test 16 will determine if the current sample record being interrogated is for probe 2 or not. If it is, the routine will advance to a second probe routine 18 (described hereinafter with respect to FIG. 11) which compares against the various types of signals which can be sensed on the second probe. But if test 16 is negative, then the routine of FIG. 9 advances to a third probe subroutine 20 (described hereinafter with respect to FIG. 12) which compares against the various types of signals which can be sensed on the third probe.

In FIG. 9, when the sample buffer has been loaded for each of the three probes and the corresponding sample records analyzed, eventually test 12 will be affirmative causing the program of FIG. 9 to reach a correlation subroutine 21 wherein an attempt is made to determine the causal event by combining raw analysis results (Qs) for the three probes, as described with respect to FIG. 12a, hereinafter; or, if that fails, by simply choosing the category one probe at a time in a decision subroutine called by the correlation subroutine and described with respect to FIG. 13, hereinafter. The group counter is incremented in a step 22 and a test 23 determines if the group counter has advanced to designate a full group of M+N records. If not, a negative result of test 23 causes the program of FIG. 9 to return to the series of steps 4 so as to advance the R' pointer, increment the R' counter and set P' equal to 3 so that the next record in the classification group can be passed through the iterative part of the routine of FIG. 9 to have the samples for each of the three probes categorized. When an entire group of records (such as thirty records or so), each having 104 samples for each of three probes, has been classified, test 23 will be affirmative causing the program of FIG. 9 to advance to a step 24 in which the classification flag for the G' group is reset. Then a test 25 determines if further distress analysis routines are available in the present embodiment of the invention, as determined by a permanent distress-analysis-available flag. If so, a temporary distress analysis flag is set in a step 26. In this embodiment, test 25 is negative, so G' is incremented in a step 27 so as to point to the next group in the sequence. Then the program will finally end at the point 3. An example of distress analysis appears in a commonly owned, copending U.S. patent application entitled "Statistically Correlated, Electrostatic Engine Diagnostics", U.S. Ser. No. 453,961, filed contemporaneously herewith by Zwicke et al.

In subsequent calling of the record classification program of FIG. 9, if all existing groups have been classified, test 2 of FIG. 9 will be negative causing the program to end at point 3. The utilization of the classification flag for the G' groups permits classification to be done asynchronously with acquisition of groups of records to be classified. Thus if the classification program falls behind the acquisition of new records (which is usually unlikely but might possibly happen during a highly active engine condition), so long as the record buffer is not full, data acquisition can continue.

FIRST PROBE SUBROUTINE—FIG. 10

The first probe subroutine 15 of FIG. 9 is reached in FIG. 10 through an entry point 1 and a first step 2 sets C MAX for the first probe (P') equal to 6, since the present embodiment has provision to discriminate between six different categories which may be sensed by the first probe. Of course, this number can vary, in any given embodiment. The iterative process of the first probe subroutine begins in FIG. 10 by a series of steps 3, the first of which increments the category counter, C, so as to advance it from the zero setting of steps 5 in FIG. 9 to cause the record set in the sample buffer in steps 5 of FIG. 9 to be examined for the first category (C=1) of the first probe in the subroutine of FIG. 10. Then a parameter buffer is loaded with the parameters shown in illustration (c) at the top of FIG. 6 for the first probe and the first category, as set forth in Table 2. A quality factor, Q, (an indication of how well a given sample record fits into a given category) is set to zeros, and a degrade factor (utilized in determining Q) is set to zeros.

In FIG. 10, a test 4 determines if the current category to test the sample against is the first category or not. Initially it is, so an affirmative result of test 4 reaches a step 5 in which a sign is set equal to plus. This sign value defines the polarity (+ or −) of the primary, threshold-exceeding pulse of a pulsatile category; a record with an opposite pulse cannot be of that category. This can be achieved by having a sign value which is set to a positive integer in contrast with being set to a negative integer, or in any other way as desired. Then a narrow pulse subroutine, described hereinafter with respect to FIG. 25, is called to determine if the current sample record is classifiable as an initially positive-going, narrow pulse indicative of metal rubbing on an abradable seal in the compressor, as exemplified in FIG. 57, by utilizing the parameters set forth in Table 2 for probe 1, category 1, fetched in steps 3. After completion of the narrow pulse subroutine 6, the quality factor Q determined in that subroutine is stored as the Q for category 1, in steps 7. If desired, and if suitable storage capacity is available, all of the results of the processing within the narrow pulse subroutine 6 may be stored at this point in the subroutine, if desired. Then a test 9 determines if the current category is the maximum category (6 for the first probe in the present embodiment). If not, the subroutine of FIG. 10 returns to the steps 3 to set up operation for testing the sample against the second category. The category counter, C, is incremented and new parameters are brought into the parameter buffer as illustrated in Table 2 for probe 1, category 2. Then, test 4 is negative and a test 10 is affirmative so that a step 11 sets the sign to a negative value and the narrow pulse subroutine 6 is again called utilizing the parameters for probe 1, category 2 to determine if the sample record for probe 1 is classifiable as an initially negative going, narrow pulse indicative of metal-to-metal rubbing in the compressor, as exemplified in FIG. 58.

The resulting quality factor is stored for the second category and test 9 determines if all categories have been checked or not. In this case, they have not, so a negative result of test 9 reaches the steps 3 one more time. C is incremented so that parameters illustrated in Table 4 for probe 1, category 3 are loaded into the parameter buffer. Q and degrade are reset to zeros and tests 4 and 10 are negative leading to a test 13 which will be affirmative. This reaches a surge subroutine described with respect to FIG. 43, hereinafter, which processes the current first probe sample record to see how closely it compares with a compressor surge record, an example of which is illustrated in FIG. 59. Then the quality factory Q is saved for the third category, results may be stored if desired, and the subroutine of FIG. 10 continues in a like manner for additional categories. Specifically, a test 15 determines a category 4 should reach a loose electrode subroutine 16, described with respect to FIG. 44 hereinafter, wherein the parameters of Table 5 are utilized to determine if the electrode within the first probe is loose as indicated by a signature exemplified in FIG. 60. And, finally, a negative result of test 15 will reach a loose probe/rub strip subroutine 17, described with respect to FIG. 54 hereinafter, to determine if probe 1 had a loose probe connector, as exemplified by the waveform of FIG. 61, using the parameters of Table 6 for probe 1, category 5. Then Q for the fifth category is set in steps 7; test 9 is negative, and C is incremented to 6 in steps 3. Again test 15 is negative, reaching the subroutine 17, but this time to determine if a rub strip (compressor abradable seal) has peeled off, by means of parameters illustrated in Table 6 for probe 1, category 6. An exemplar of the signature of a rub strip peeling off is illustrated in FIG. 62. When the sample record for the first probe has been compared against all six categories of the present embodiment, the record classification program of FIG. 9 is reverted to through a return point 18. In FIG. 9, the program reverts to the steps 5 for the next probe in the sequence, eventually reaching the second probe subroutine 18 as illustrated in FIG. 11.

SECOND PROBE SUBROUTINE—FIG. 11

In FIG. 11, the second probe subroutine is entered through a point 1 and a step 2 sets the maximum number of categories for the second probe equal to 8. These are the categories for which exemplary wave shapes are illustrated in FIG. 60–FIG. 67, respectively. The iterative part of the second probe routine of FIG. 11 is similar to that described for the first probe with respect to FIG. 10. Specifically, the steps 3 and 4 are the same but for the second probe, tests 5 and 6 call a wide pulse subroutine 7, described with respect to FIG. 34 hereinafter, after a step 8 sets the sign negative; a test 10 causes setting of a positive sign in a step 11 before calling the wide pulse subroutine 7. Then tests 12 and 13 cause categories 4 and 5 to be examined with plus and minus signs, as set in steps 14 and 15, by means of the narrow pulse subroutine 16. Test 17 causes the record to be examined in the loose electrode subroutine and causes the record to be compared against category 7 and then category 8, in the loose probe/rub strip subroutine 19. When the sample record has been compared against all eight categories, a test 20 causes the record classification program of FIG. 9 to be reverted to through a return point 21.

In FIG. 9, the third probe is handled by negative results of tests 14 and 16 in FFF. 9 reaching the third probe routine 20 of FIG. 12.

THIRD PROBE SUBROUTINE—FIG. 12

In FIG. 12, the third probe routine is reached through a point 1 and a step 2 sets the maximum number of categories equal to 14. In the iterative part of the program, the steps 3 are performed in the same fashion as in FIGS. 10 and 11 but fetch the parameters for the third probe categories. As in FIG. 10 and FIG. 11, a series of tests 4–16 cause the routine to examine the sample record for the third probe against 14 catgories, exemplary wave shapes for which are illustrated in FIG. 62 and in FIG. 68–FIG. 80 hereinafter. A series of steps 19–24 set the sign as appropriate and, depending upon the particular category, the sample record is examined for its likelihood of being in that category by the narrow pulse, wide pulse, and loose connector/rub strip subroutines 26–28 in the case of categories 1–3, 4–9 and 10, respectively. The sample record is examined for categories 11 and 12 by an abnormal A/B chop subroutine 30, described with respect to FIG. 54 hereinafter, for category 13 in a normal afterburner chop subroutine 31, described with respect to FIG. 55 hereinafter, and for category 14 in an acceleration/deceleration subroutine 32, described with respect to FIG. 56, hereinafter. In each pass through the routine of FIG. 12, the steps 33 are the same as steps 7 in FIG. 10 hereinbefore, except relating to the third probe, and when the record has been compared against all categories, a test 34 causes the record classification program of FIG. 9 to be reverted to through a return point 35.

Of course, if new categories are found to be useful for any probe, new subroutines and expansion of each probe subroutine can be made, as desired.

CORRELATION SUBROUTINE—FIG. 12a

In each of the subroutines called by the first probe, second probe, and third probe subroutines of FIG. 10– FIG. 12, the relative likelihood that the given sample record fits into the category related to the particular subroutine is manifested by the quality factor, Q. The manner in which this quality factor is developed, for each sample record as it is procesed through each subroutine, is described with respect to FIG. 24 through FIG. 56 hereinafter. In the present embodiment, the quality factors generally range from zero to one, although this may differ in dependence on the manner in which the present invention is implemented. For the purposes of describing the correlation subroutine illustrated in FIG. 12a and the decision subroutine illustrated in FIG. 13, it suffices to say that quality factors, Q, are assigned for each sample record of each probe with respect to each of the categories which may relate to that probe, and these quality factors range from zero to unity. Following completion of the individual probe subroutines 15, 18, 20 of FIG. 9, the record classification program calls the decision subroutine 21, illustrated in FIG. 13.

In this embodiment of the invention, interprobe correlation is performed by combining the quality factors (Q) determined for some of the categories on each of the three probes. These are categories that are known to have correlative significance for Q's between zero and 1 (as is the case herein). A combination of them that provides an increase over any of the individual Q's utilized, provided that there is some value to at least two of them, may be achieved by the well known geometric summation formula:

$$f(Q) = 1 - [(1-Qa)(1-Qb)(1-Qc)].$$

In case one of the Q's is zero (only two Q's being involved), the formula simplifies $$f(Q) = Qb + Qc - QbQc.$$

This formula is utilized in the correlation subroutine of FIG. 12a to correlate, if possible, the potential categories utilizing the raw Q values determined in the first, second and third probe subroutines. To do this, the values of Qa, Qb, and Qc are set equal to the Q's of the probes which may correlate with each other. As an example, in FIG. 12a the correlation subroutine is entered through a point 1 and in a series of steps 2 Qa is set equal to the value of Q for probe 1, category 5 which is a rub strip (abradable seal). Qb is set equal to the value of Q determined for probe 2, category 8 which is also rub strip; and Qc is set equal to the value of Q for the third probe, category 10 which is also rub strip. Then a local category number, C, is set equal to 1 and Q for that category is set equal to f(Q), as described hereinbefore. Assuming that each probe determined there was about a 30% chance of the event sensed thereby in that particular record being a rub strip, resulting in Q's of 0.3 for each probe, Q(C) for that category will end up at about 0.66, which is very indicative of a likelihood that the event was in fact a rub strip. The steps 2 are the only steps in FIG. 12a that utilize a value of Qa. The remaining correlations occur only between the second and the third probe. Therefore in steps 3, Qa is set equal to zero and remains so set throughout the remainder of the subroutine. Then Qb is set equal to the value of Q for the second probe, category 3 which is first high turbine rub, and Qc is set equal to the value of Q for the third probe, category 5 which is high turbine rub. Then C is set equal to 2 and Q(C) is determined as f(Q). This will provide a Q for category 2 of first high turbine rub. In steps 4, Qc is set equal to the Q for the third probe, category 7 which is high or low turbine impact-induced rub. Qb remains set as before so that the Q for the third category will relate to impact-induced turbine rub. In steps 5, Qb is set equal to the Q value of the second probe, category 4 which is second high turbine rub, and Qc is left set equal to probe 3, category 7 which is high or low turbine impact-induced rub. Thus the value of Q for the fourth category will also relate to impact-induced turbine rub. In step 6, Qc is set equal to the value of Q for the third probe, category 5 which is high turbine rub for comparison with probe 2, category 4 which is second high turbine rub. Thus the value of Q for the fifth category will be for second high turbine rub.

In FIG. 12a, steps 7 set Qb equal to the value of Q for second probe, category 1, first high turbine blade erosion and set Qc equal to the value of Q for probe 3, category 8 which is high turbine blade erosion. Thus the Q for the sixth category will be for high turbine blade erosion. In steps 8, Qb is set equal to the value of Q for the second probe, category 5 which is second high turbine blade or vane erosion for comparison with third probe, category 8 high turbine blade erosion. Thus the value of Q for the seventh correlated category will be for second high turbine blade erosion. Then in steps 9, Qc is set equal to the third probe, category 9 which is high turbine vane erosion. Thus the value of Q for the eighth correlation category will be second high turbine vane erosion. And in steps 10, the value of Qb is set equal to the value of Q for the second probe, category 2 which is first high turbine vane erosion for comparison with probe 3, category 9 high turbine vane erosion. Thus the value of Q for the ninth correlation category will be first high turbine vane erosion.

When steps 2 through 10 have been completed, it is not yet known whether any correlation has occurred at all. Therefore, a series of steps 11 set up the conditions to determine if any meaningful correlations have occurred. A local value C MAX is set equal to 9; a value Q MAX is preset to zero; and a category counter, C, is initialized at zero. Then in a step 12, C is incremented and a test 13 determines if the value of Q for category 1 is less than 0.5 (or any other threshold value which is chosen to be appropriate in any implementation of the invention). If it is less than the threshold amount, an affirmative result of test 13 will reach a step 14 which sets Q or C equal to zero. But if the value of Q for this category is equal to or greater than the threshold amount, a negative result of test 13 will reach a test 15 to determine if this value of Q is less than the previously determined Q MAX. The initial pass through test 15 will always be negative because Q MAX is initialized at zero in steps 11. A negative result of test 15 reaches steps 16 where Q MAX is set equal to the value of Q for the current category and the category (CAT) is set equal to the current category. A test 17 determines if the full complement of categories have been examined or not. If not, the steps and tests 12-16 are repeated until all nine categories have been examined. Concerning the test 13, it may be pointed out that for the values of Q involving only two probes (steps 3-10), if each has a Q value of 0.293, the result will be equal to 0.5 and the test will pass. The threshold can therefore be adjusted to suit the needs to which the invention is to be put.

The correlation subroutine continues in FIG. 12b with a test 20 which determines if Q MAX is non-zero. If Q MAX is zero, that means no correlation has occurred and regular probe by probe choosing of the highest Q value per probe must be performed utilizing the decision subroutine of FIG. 13, as is described hereinafter. Assuming a Q MAX has been chosen, a negative result of test 20 will reach a pair of steps 21 to set the category number, C, equal to zero and to reset a P1 flag (the purpose of which is described hereinafter). Then a step 22 increments C so as to point to the first category. And a test 23 determines if this is the category selected as having the highest Q value in the steps 16 of FIG. 12a. If not, a negative result of test 23 reaches a test 24 to determine if all of the categories have been tested. If not, step 22 will increment C and test 23 will determine if this was the winning category. Once the winning category is found, the subroutine of FIG. 12b proceeds through a series of tests 24-32 to see which category was selected. If test 24 is negative, that means category 1 was not selected and that, therefore, the first probe was not involved in correlated category selection. Therefore, a P1 flag is set in a step 33. This causes the category for the first probe to be selected utilizing the decision subroutine of FIG. 13 as described hereinafter. Depending upon which category has been selected, one of the tests 24-32 will be affirmative causing a corresponding one of a plurality of steps 34-42 to set the categories for the current record and the individual probes to those categories which were in fact correlated to the maximum Q value of the selected correlated category.

In FIG. 12b, a negative result of either step 24 or step 32 indicates something is wrong so a system error flag may be set in steps 44. And, since the classification by correlation has failed, the decision logic will be utilized. Thus in steps 44, P' is set equal to 4. Similarly, if no correlation category has been selected, test 20 will have been negative reaching a step 45 which sets P' equal to 4. Then a pair of steps 46 will decrement P' so as to point to the third probe (following either step 44 or 45) and fetch the Q values for all of the categories (including the unknown category which is designated as one more than the maximum category number for the involved probe. And then a decision subroutine 47 is called to select the highest Q value (if any) as described with respect to FIG. 13 hereinafter. A test 48 determines if probe 1 has passed through the decision subroutine 47 or not and if not, the routine reverts to the steps 46 to decrement P', fetch the Q values for the selected probe and call the decision subroutine 47 once again.

In the case where a correlation has occurred so that test 20 is negative, but it isn't the first correlation category so that test 24 is negative, the P1 flag is set in step 33. When the appropriate one of the steps 35–42 has been performed, a test 48 determines if the P1 flag has been set. If it has, this reaches a step 49 to set P' equal to 2 so that when decremented in step 46 P' will point to the first probe and cause it to be correlated by itself in the decision subroutine 47. Notice that the only time when the decision subroutine 47 is not called at least once is when correlation of rub strip has occurred so that test 24 has been affirmative. This causes a negative result of test 48 so that the record classification program of FIG. 9 is reverted to through a return point 50.

DECISION SUBROUTINE—FIG. 13

Figure 13:
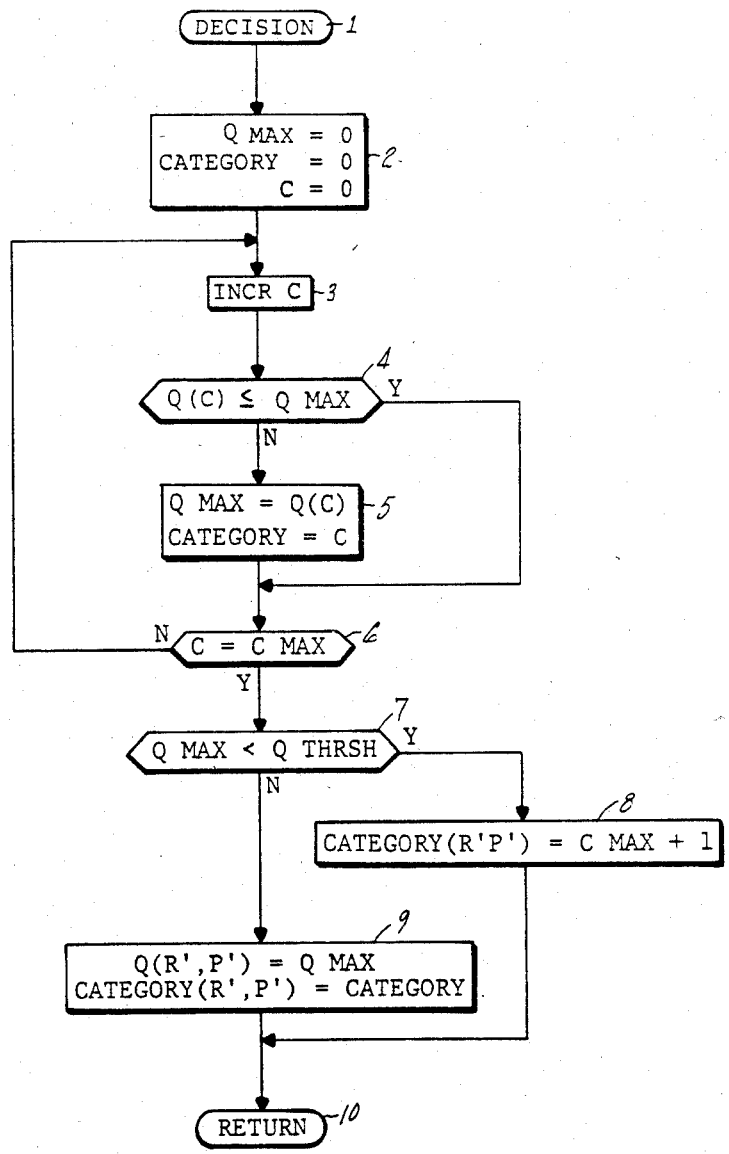

In FIG. 13, the decision subroutine is entered through a point 1 and a series of steps 2 set a temporary value, Q MAX, equal to zero; set the category equal to zero; and set the category counter, C, equal to zero. Then a first iterative part of the subroutine of FIG. 13 commences with a step 3 which increments C and a test 4 determines if the quality factor assigned to category C is less than or equal to the maximum quality factor. For the first category in the set of categories for any given probe, test 4 must be negative since Q MAX is set at zero in the steps 2. Thus Q MAX becomes set in one of the steps 5 to the Q for the current category and the category for the probe is set equal to C. That is to say, the winning category is set to be equal to the category (identified by C) for which Q MAX is most recently set equal to Q of the current category. Then a test 6 determines if C MAX (as set in step 2 of FIG. 10, FIG. 11 or FIG. 12) has been reached or not. If not, this means all of the categories for the given probe have not had their Q values examined against the others as yet, and a negative result of test 6 will cause the decision subroutine of FIG. 13 to revert to step 3, where C is incremented to identify the next category in the sequence. If its quality factor is not equal to or less than the previously determined maximum, its value is taken as the maximum and it is identified as the category for that probe in the steps 5. When all of the categories for the given probe have been examined, an affirmative result of test 6 will reach a test 7 in which Q MAX is compared against some threshold value for Q which may be established. For instance, the Q threshold may be set at 0.5, in the general case of the present exemplary embodiment. If a given category has too low a Q value, an affirmative result of test 7 will reach a step 8 in which the category for the record under test for the current probe is set equal to the maximum category number plus 1, which is used to define the record as of "unknown" characteristics. Thus for the first probe, if Q MAX is zero (meaning the particular sample record does not in any way resemble any of the six permitted categories for the first probe), or if the maximum Q is less than 0.5, the category for this sample record for this probe will be set (in step 8) to seven, meaning the category is unknown. On the other hand, if the highest Q value for the given sample record for the particular probe is equal to or greater than 0.5, a negative result of test 7 will reach steps 9 in which the quality factor, for the particular record involved and for the particular probe involved, is set equal to the Q MAX provided in the steps 5. And the category for the particular record and particular probe is set equal to the category determined in the steps 5. Following either steps 8 or 9, the correlation subroutine of FIG. 12a is reverted to through a return point 10 in FIG. 13.

BASIC SUBROUTINES—FIG. 15–FIG. 24

Each of the subroutines referred to in FIG. 10 through FIG. 12 which determine the likelihood that the record represents a wave shape indicative of a given category, utilize one or more basic (primitive or root) subroutines of FIG. 15–FIG. 24, an understanding of which is necessary as a precursor to the understanding of the subroutines of FIG. 25–FIG. 56. Each of these basic subroutines operate on the magnitude of the individual samples related to the given probe involved within the sample buffer record which is brought into the record classification program by steps 5 in FIG. 9. In these subroutines, S refers to the sample number (of the 104 samples in the given example) and V relates to the voltage, the value, or the magnitude of a given sample (which for the purposes of describing these subroutines can be taken to be the same thing). Further, in the case where no record has been sensed for a given probe, no classification is made of that record, the category being forced to zero (step 11, FIG. 9). Thus, all of the classification subroutines described herein are only called when there was a threshold crossing within the record and therefore some threshold-exceeding activity which can be compared in the subroutines.

Width/Peak—FIG. 14

Referring now to FIG. 14, a width/peak subroutine finds the width of a primary pulse of those categories which are pulse-like in nature, and determines the sample number and magnitude of the peak of the primary pulse. If a width A.G.C. request is made prior to calling the subroutine, the subroutine is performed a first time just to find the value of the primary pulse peak, and then a second time utilizing a width threshold which is a function of the magnitude of the peak found during the first execution of the subroutine.

In FIG. 14, the width/peak subroutine is reached through an entry point 1 and a series of steps 2 reset an A.G.C. once flag (which keeps track of when the second iteration has been made as a function of the peak magnitude, if used); the sample number of the peak is arbitrarily preset as the beginning sample (the number of the sample which crossed the probe threshold within the record under consideration); the value of the peak is arbitrarily set to equal that of the beginning sample; and a local sign value (SIN) is set positive. The local sign value is used so as not to overwrite the sign value set by one of the calling subroutines of FIG. 10–FIG. 12, which must be retained as indicative of the polarity which the primary pulse (that which caused the threshold crossing), must have for such category, as becomes more apparent in the description of other subroutines hereinafter.

In FIG. 14, a test 3 determines if the beginning sample is negative, and if so, an affirmative result reaches a step 4 in which the local sign is set negative. If the begining sample is not negative, step 4 is bypassed. Then a step 6 sets a sample counter equal to the begining sample (the sample which the subroutine has been commanded to begin with). A test 7 determines if the value of the beginning sample is greater in magnitude than the value of the heretofore arbitrarily set peak, in either the positive or the negative direction. That is, if the current sample is more negative than a previously established negative peak, test 7 will be affirmative; if the current sample is more positive than a positive peak, test 7 will be affirmative. If test 7 is positive, the new sample indicative of peak is set equal to the current sample, and the value of the peak is set equal to the value of the current sample, in steps 8. If test 7 is affirmative, steps 8 are bypassed.

Then, a test 10 determines if the value of the current sample is less than a threshold magnitude at which width is to be determined; by multiplying with the sign, positive sample values are retained positive and negative sample values are converted to positive, so that only positive thresholds need be used in the test 10. In the general case, the width threshold is quite low compared to the probe threshold which would recognize a pulse (such as compressor metal-on-metal rubbing, probe 1, category 2, FIG. 58, and the like). Therefore, in the initial few samples tested, test 10 is likely to be negative thereby reaching a test 12 wherein it is determined whether or not the sample is the first sample of a record (sample 1). Initially, such will not be the case and a negative result of test 12 will reach a step 13 which decrements S and reverts to test 7. In this manner, the steps and tests 7–13 begin at a point usually approximately equal to the 27th sample, (as set in step 13 of FIG. 9), stepping downwardly to the beginning of the record and looking to see if there are any peaks higher than the point of threshold crossing. In other cases, the width/peak subroutine may be called to examine the width of a following pulse; in such cases, the beginning sample is set at the sample which had been determined to have the peak value for the following pulse so that a similar situation exists: starting at the peak of the pulse and working downward through lower sample numbers, the steps and tests 7–13 look for any higher peak and for a crossing in the value below a width threshold.

In FIG. 14, in the event that the value of a given sample is less than the width threshold, an affirmative result of test 10 will cause a temporary beginning sample number, S(BEG), to be set equal to the current sample number. But if there is no affirmative result of test 10, starting with the beginning sample and ending up with the first, leftmost sample in the record, a negative result of test 10 followed by an affirmative result of test 12 will reach a step 15 in which the temporary beginning sample number is set equal to zero.

In FIG. 14, following steps 14 or 15, a similar process is repeated but starting just ahead of the beginning sample and working upwardly (to the right) to see if there are any peaks of a magnitude greater than the beginning sample and to determine when the pulse drops below the threshold value at the upper sample end thereof. Specifically, a step 17 sets the current sample number equal to one greater than the beginning sample. Then a test 18 determines if the value of the current sample is greater than the value of the previously determined highest valued (peak) sample, which may have been established in steps 8 or by the preset of steps 2. If the current value is higher, an affirmative result of test 18 will reach steps 19 to set the sample number for the peak equal to the current sample number and to set the value of the peak equal to the value of the current sample. But if the current sample does not exceed the previously established peak, a negative result of test 18 will bypass the steps 19. Then a test 20 determines if the upper end (higher sample number end) of the pulse has decreased below the width threshold value or not. If not, a negative result of test 20 reaches a test 22 which determines if the current sample number is equal to the maximum sample number of the record (sample number 104, in the example herein), or not. If not, the sample number is incremented in a step 23 and the steps and tests 18–20 are repeated again. When the value of the current sample decreases below threshold, an affirmative result of test 20 will reach a step 24 which causes a temporary end-of-pulse sample number, S(END), to be set equal to the current sample number. But if the maximum sample number is reached without ever decreasing below the threshold value, a negative result of test 20 followed by an affirmative result of test 22 will cause a step 26 to set the temporary end-of-pulse sample number to be set equal to one greater than the maximum sample (for purposes described hereinafter).

In FIG. 14, following steps 24 or 25, a test 27 determines if width A.G.C. had been commanded by the calling subroutine, which is the case when called by the narrow pulse subroutine and wide pulse subroutine with respect to the primary pulse of a record. If so, an affirmative result of test 27 reaches a test 28 to determine if the second pass through the width/peak subroutine has been accomplished for the purposes of examining width with a varied threshold, or not. If it has, an A.G.C. once flag will have been set, and an affirmative result of test 28 will cause bypassing of any further iterations through the subroutine of FIG. 14. On the first pass through, however, the test 28 is negative because the flag is reset in the steps 2. This reaches steps 30 in which the width threshold is used as a fraction to find the desired width threshold by multiplying it by the absolute value of the peak magnitude found for the pulse during the first pass through the subroutine. If A.G.C. is invoked, the initial value of THRSH is set in the calling program to be a decimal fraction (0.0 to 1.0) of the peak value found during the first pass through the subroutine. Step 30 then computes the absolute threshold by multiplying the percent-threshold by the peak value. In this mode of operation, the initial THRSH value is not critical (any low positive value will suffice) because the first pass is used solely to get V(PK), and not to get the exact width.

In FIG. 14, when the A.G.C. has been set up by steps 30, the steps and tests 6–25 are repeated, with the adjusted width threshold. The steps and tests 7, 8 and 18, 19 will be unproductive, since the highest peak has already been found and the change in threshold does not vary that at all. Thus, the iterative processes are to look to the left to find the left-most threshold by test 10 and to look to the right to find the right-most threshold by test 20.

When the second pass through the iterative processes of FIG. 14 is completed, if the width A.G.C. had been commanded, test 27 is again affirmative but test 28 is affirmative so that the subroutine advances to steps 32 to define the beginning sample of the pulse as that sample number which just falls below the threshold, by causing the beginning sample to be equal to S(BEG) as set in step 14 and set the end sample to be equal to the sample having a value just above the width threshold, by causing it to be set to equal one sample less than S(END) set in step 24. On the other hand, if thresholds were not crossed, the beginning sample will equal zero and the ending sample will equal the maximum sample, due to the combination of steps 15, 25 and 32. And, the width is then set equal to the difference between the end sample and the beginning sample. Then the program returns to the routine which called the width/peak subroutine of FIG. 14, through a return point 33.

FOLLOWING-PEAK SUBROUTINE—FIG. 15

The following-peak subroutine of FIG. 15 is utilized to find the location, S(PK) and the magnitude, V(PK), of the first peak exceeding a following-peak threshold in a sample interval extending from a beginning sample to an ending sample that is defined to the subroutine by the routine which calls it. If the absolute maximum peak of a following pulse is desired, the width/peak subroutine is called thereafter for that purpose. The subroutine can search leftward from high sample numbers to low sample numbers (reverse) or it can search rightward from low sample numbers to high sample numbers (forward). And, in either searching direction, the subroutine can be caused to look for just positive peaks, just negative peaks, or either, in dependence upon whether a sense command is set equal to $+1$, $-1$, or zero, respectively.

In FIG. 15, the following-peak subroutine is reached through an entry point 1 and the sample number and value of the peak are preset to zero in steps 2. If the calling program desires finding the first peak in a leftward or reverse search, it provides a reverse command to the subroutine of FIG. 15, which is sampled in a test 3. First, assuming that the reverse command has not been made, test 3 will be negative so a step 4 will set the sample counter S to the beginning sample, which may either be the first sample of the record in some cases or it may be the sample to the left of a pulse in other cases. The routine proceeds iteratively, simultaneously looking for both a negative peak and a positive peak. S is incremented in a step 5 and the value of S is compared with the value of the next lower sample in a test 6 to see if it is more positive than the next lower numbered sample. If it is, this means the next lower numbered sample is the first negative peak in the direction of scan, as in FIG. 16. An affirmative result of test 6 reaches a test 7 which determines if this negative peak value is at least as negative as a minus following-peak threshold. If it is not, the value of the next lower sample number is not accepted as a peak, as in FIG. 17. But if it is as negative as the minus following-peak threshold (FIG. 16), a negative result of test 7 reaches a test 8 to determine if negative peaks are of interest to the calling program. In test 8, the sense command may be either $-1$, 0 or $+1$. If it is $-1$ or 0, then negative peaks are of interest to the calling program and the sense command is equal to or less than zero, so that an affirmative result of test 8 will reach steps 10 in which the sample number of the peak is taken to be equal to one less than the current sample number and the value of the peak is set equal to the value thereof.

In FIG. 15, if either test 6 or 7 is negative, this means that a negative peak has not been identified by comparing the value of the current sample number with the value of the next lower sample number. Or if test 8 is negative, that means that only positive peaks are being looked for and a negative peak should be ignored (if found). In any of these situations, a test 12 determines if the value of the current sample number is less positive than the value of the next lower sample number. If it is, an affirmative result of test 12 reaches a test 13 to determine if the value of the next lower sample is more positive than a positive following peak threshold. If it is, this means that a positive peak of a sufficient magnitude has been located, as in FIG. 18. An affirmative result of both tests 12 and 13 reaches a test 14 which determines if positive peaks are being looked for. This is the case whenever the sense command is set at either zero or $+1$. If such is the case, an affirmative result of test 14 will reach the steps 10 to identify the sample number of the peak and its value as being those of the next lower sample.

In each iteration (for subsequent values of S) of the subroutine of FIG. 15, if a negative peak is not found, or when found is not desired, negative results of tests 6–8 will reach tests 12–14. If a positive peak is not found or is not desired, negative results of tests 12–14 will reach a test 18 to determine if the end sample defined by the calling program has been reached or not. The end sample may typically be the maximum sample (104 in the present example), but it need not be. If the end sample has not been reached, a negative result of test 18 causes the program to revert to step 5 where the S counter is incremented and the present sample is compared with the preceeding sample in the tests 6 and/or 12. A feature of the subroutine of FIG. 15 is utilizing the sense word to define whether a negative peak is being looked for, or a positive peak is being looked for, or any peak, whether positive or negative is being looked for. This permits examining wave shapes for opposing or non-opposing following peaks, in a simple manner.

When the forward portion of the subroutine of FIG. 15 has been completed, either by reaching the end sample or by finding a peak of a desired polarity, completion of steps 10 or a negative result of test 18 will cause the program to revert to the calling routine through a return point 20.

In FIG. 15, if the calling program desired to find the first peak to the left of some point, it will set the reverse flag and an affirmative result of test 3 will reach a step 22 where the sample counter is set equal to the end sample (the left-most sample) defined by the calling routine, to commence scanning in the reverse direction. Then a series of tests 23–25 look for a desired negative peak in the same fashion as tests 6–8. If a desired negative peak is found, steps 27 identify the sample and the value of the peak as those of the next higher numbered sample. On the other hand, if a negative peak of sufficient magnitude is not found or a negative peak is not desired, negative results of any of tests 24–26 will reach a series of tests 29–30 looking for a desired positive peak, as in FIG. 19. If one is found, steps 27 identify the sample and value of the peak. Normally, the first few samples will not indicate having crossed a peak, and negative results of tests 24 and 29 will reach a test 34 to determine if the beginning sample (where scanning is to end in the reverse scan case) has been reached or not. Notice in FIG. 19 that the following-peak threshold can be set to a value which will cause small peaks of no interest to be ignored; only a peak of interest is thus identified. If not, a negative result of test 34 reaches the step 23 and the process repeats until a peak has been found. An affirmative result of test 34, indicating that all the samples have been tested and no peak found, or passage through steps 27 which identify a peak, will cause the program to revert to the calling routine through the return point 20.

MULTIPLE PEAKS SUBROUTINE—FIG. 21

Figure 20:
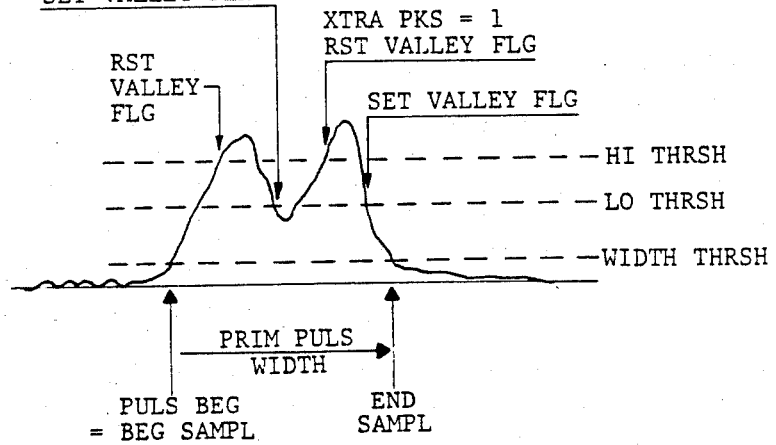

Referring to FIG. 21, a multiple peaks subroutine is reached through an entry point 1. The multiple peaks subroutine is utilized specifically to sense closely adjacent positive peaks of the same polarity, as occurs when there is an impact induced turbine rub, of the type illustrated in FIG. 74. However, the multiple peaks subroutine of FIG. 21 can detect any number of adjacent positive peaks. In a series of steps 2, an extra peaks value (a value indicative of how many peaks are found by the subroutine) is preset to zero; a valley flag used in the subroutine is reset; and the S counter is set equal to the beginning sample, which is identified by the calling program. The iterative part of the subroutine of FIG. 21 begins with a test 3 which determines if the value of the current sample is equal to or greater than a multiple peak high threshold which is provided to the subroutine by the calling program, as shown in FIG. 20. The multiple peak high threshold is a threshold value which a peak must exceed in order to be recognized as such. Since the beginning sample is normally set as the start of a wide pulse of some sort, the first few passes through the test 3 are likely to be negative, in the general case. This reaches a step 4 where S is incremented and a test 5 which determnines if S is set to the end sample (normally identified as the end of a wide pulse). If test 5 is negative, the next sample is tested to see if its value exceeds the multiple peak high threshold. This will continue until finally the value of the current sample does exceed the multiple peak high threshold, which causes an affirmative result of test 3. This reaches a test 7 which interrogates the valley flag; the first pass through test 7 is always negative because the valley flag is reset in the steps 2. Resetting of the valley flag is reinforced in step 8 and a test 9 determines if the current value is below a multiple peak low threshold. This is a threshold value that the pulse wave shape must dip down under to recognize the separation between the first peak and a subsequent peak. Initially, the first pass through test 9 has to be negative since the same sample cannot both be higher than the multiple peak high threshold and lower than the multiple peak low threshold. Thus an ensured negative result of test 9 will reach a step 10 which increments S and a test 11 which tests S to see if the end sample has been reached yet, or not. In the general case, it has not, so the next sample is tested in test 9 to see if its value is below the multiple peak low threshold. This process continues until the sample value dips below the multiple peak low threshold which causes an affirmative result of test 9 to reach a step 12 which sets the valley flag (see FIG. 20). Then the program returns to step 3 to look for the next subsequent peak. Initially, when the test 9 is affirmative, test 3 has to be negative because the sample cannot have a value which is both below the low threshold and above the high threshold. Therefore, a negative result of test 3 will again reach step 4 to increment S and test 5 to see if the end sample has been reached or not. This process repeats until once again the value of the sample exceeds the multiple peak high threshold (if there is an additional sample which will do so). When a second or subsequent peak is sensed, an affirmative result of test 3 finds step 7 affirmative and therefore reaches a step 14 which increments an extra peaks counter, thereby keeping track of how many peaks in excess of one have been sensed by the subroutine of FIG. 18. After sensing each peak through test 3, the routine reaches test 9 and looks for a following valley, sets the valley flag, and looks for a subsequent peak until the end sample is reached. This subroutine may be modified to look for multiple negative peaks, in an obvious manner. An affirmative result of either tests 5 or 11 will cause the calling routine to be reverted to through a return point 15.

ZERO CROSSINGS SUBROUTINE—FIG. 22

Referring now to FIG. 22, a zero crossings subroutine is reached through an entry point 1. This subroutine senses the number of times that the value of the samples changes from positive to negative, or vice versa, concurrently with the respective magnitudes of the two samples exhibiting the polarity change differing by some threshold amount. This threshold amount determines the degree of immunity to ordinary noise. In FIG. 22, a pair of steps 2 preset the number of zero crossings (which is the value that the subroutine of FIG. 22 determines) to zero, and the S counter is set equal to the beginning sample specified by the calling routine. In the iterative portion of FIG. 22, a series of steps 3 increment S and then take the product of the value of the current sample and the value of the preceding sample. If the two samples are both negative or both positive, the product will be positive. But if they are of opposite sign, the product will be negative. And, the difference is taken as the absolute value of the difference between the current sample value and the value of the next lower numbered sample. Then a test 4 determines if the product is positive. If it is, this means that the two samples are of the same sign and there has not been a zero crossing. An affirmative result of test 4 reaches a test 6 to determine if the end sample, as defined by the calling program has been reached. If not, the subroutine of FIG. 22 reverts to the steps 3 to compare the next pair of samples.

If a zero crossing has occurred, test 4 will be negative reaching a test 7 which determines if the difference is equal to or greater than a zero-crossing threshold, and thereby to be recognized as a zero crossing (rather than merely noise). If so, an affirmative result of test 7 will reach a step 8 wherein the number of zero crossings is incremented. Otherwise, step 8 is bypassed. When the end sample has been reached, an affirmative result of test 6 causes the program to revert to the calling subroutine through a return point 9. The number of zero crossings thus determined is indicative of frequency content of a gross signal, and can readily discriminate between relatively low frequency signals, such as that exemplified in FIG. 61, from relatively high frequency signals, such as that exemplified in FIG. 62. This provides a course indication of frequency content without the heavy computational burden required for other methods, such as the fast Fourier transform.

R.M.S. SUBROUTINE—FIG. 23

In FIG. 23, an R.M.S. subroutine is reached through an entry point 1 and a pair of steps 2 preset the intial R.M.S. value to zero and set the S counter to the beginning sample identified to the subroutine by the calling program. Then a step 3 adds to the R.M.S. value the square of the sample value. A test 4 determines if the end sample defined by the calling routine has been reached or not, and if not, a step 5 increments S and returns to step 3. When the end sample is reached, the R.M.S. value is set in a step 6 to be equal to the square root of the R.M.S. value divided by the sample interval. The interval includes the end sample minus the beginning sample, plus one, to account for the beginning sample. Then the calling program is reverted to through a return point 7.

DEGRADE SUBROUTINE—FIG. 24

In FIG. 24, a degrade subroutine is reached through an entry point 1 and a pair of steps 2 determine the variation in a measured parameter from a nominal value for that parameter, related to a given category against which a sample record is being compared. For instance, the measured value may be a pulse width which is compared against a nominal pulse width for the given category. Comparison of the exemplary wave shapes shown in FIG. 73 and 74 illustrates that pulse width can be a good discriminant between some categories, although it may not be with respect to others. In any event, in the steps 2, an increment is set equal to the ratio of the variation to the sensitivity raised to a degradation exponent. The exponent determines how nonlinearly the degradation value will increase as the variation increases. For instance, an exponent greater than unity will weight large variations more heavily than small variations. For example, for exponent=2 and variation=1, the net degradation is $1^2=1$; but for variation=2, the net degradation is $2^2=4$: a fourfold increase in degradation. The increment is truncated by having any decimal fractions stripped off. The sensitivity is in a sense an indication of a range of variation which is tolerable. Thus, if the variation is less than the sensitivity, the increment will be a fraction and the truncation will cause the increment to become zero. Thus there is no degradation as a consequence of some measured value varying from a nominal value within the tolerance range. But the sensitivity factor is also a granularity factor because of the truncation. Thus five-thirds (equaling about 1.66) is truncated to 1.0. If the initial variation were 3, 4 or 5 compared to a sensitivity of 3, the increment is truncated to 1. But if the variation is 6, 7 or 8 in this example, the increment is truncated to 2, etc. Thus, the rate of growth of increment per unit of variation (the incremental slope) is controlled by the sensitivity. The truncation of the increment also prevents there being any fractional increments. The final one of the steps 2 updates the degradation factor, "DEGRADE", by adding the increment to it. And then the calling routine is reverted to through a return point 3.

NARROW PULSE SUBROUTINE—FIG. 25

The narrow pulse subroutine is set forth in FIG. 25a–FIG. 25c. The routine is entered in FIG. 25a through an entry point 1 and a first step 2 determines whether or not the sign is correct. It does this by multiplying the value of the threshold sample (established in step 13 of the record classification program of FIG. 9) by the sign of the primary pulse of the category which is being examined for. The sign is set in any of: steps 5 or 11 in FIG. 10; steps 14 or 15 in FIG. 11; or steps 19 or 20 in FIG. 12. If the primary pulse is of the correct polarity, the product will be positive. If it is not, a negative result of test 2 will cause the calling routine to be reverted to through the return point 2a, eliminating the current category from contention for this sample record.

TABLE 2

| | NARROW PULSE SUBROUTINE | | | | | | |
|---|---|---|---|---|---|---|---|
| | PROB 1 | | PROB 2 | | | PROB 3 | |
| PARAMETERS | C1 | C2 | C4 | C5 | C1 | C2 | C3 |
| DEGRADE MAX | 11 | 18 | 11 | 18 | 11 | 11 | 11 |
| FOLWNG PULS DVSR | 2 | 2 | 2 | 4 | 2 | 2 | 5 |
| FOLWNG PULS NOMNL WIDTH | 0 | 2 | 0 | 4 | 0 | 1 | 10 |
| FOLWNG PULS WIDTH LIM | 9 | 10 | 6 | 8 | 8 | 8 | 10 |
| OPOS PULS ABSNT | 0 | 3 | 0 | 5 | 0 | 0 | 5 |
| OPOS SEP LO LIM | 3 | 3 | 3 | 3 | 3 | 3 | 3 |
| PEAK THRSH | 1 | 1 | 1 | 1 | 1 | 1 | 1 |
| PRE R.M.S. DVSR | .1 | .2 | .15 | 1.04 | .15 | .15 | .1 |
| PRIM PULS DVSR | 2 | 2 | 1 | 2 | 1 | 1 | 3 |
| PRIM PULS NOMNL WIDTH | 2 | 4 | 3 | 3 | 2 | 3 | 3 |
| PRIM PULS WIDTH LIM | 8 | 10 | 6 | 8 | 8 | 8 | 10 |
| POST R.M.S. DVSR | .1 | .3 | .15 | 1.06 | .15 | .15 | 1.05 |
| POST R.M.S. MAX INTVL | 26 | 26 | 26 | 26 | 26 | 26 | 26 |
| R.M.S. EXP | 1 | 1 | 1 | 1 | 1 | 1 | 1 |
| SAME SEP LO LIM | 10 | 13 | 13 | 13 | 7 | 13 | 13 |
| SEPRATN DVSR | 4 | 4 | 4 | 4 | 4 | 4 | 4 |
| SEPRATN EXP | 1 | 1 | 1 | 1 | 1 | 1 | 1 |
| SEPRATN HI LIM | 26 | 26 | 26 | 26 | 26 | 26 | 26 |
| WIDTH EXP | 1 | 1 | 1 | 1 | 1 | 1.5 | 1 |
| WIDTH THRSH | .05 | .05 | .08 | .08 | .05 | .03 | .03 |

TABLE 3

| | WIDE PULSE SUBROUTINE | | | | | | | | |
|---|---|---|---|---|---|---|---|---|---|
| | PROB 2 | | | PROB 3 | | | | | |
| PARAMETERS | C1 | C2 | C3 | C4 | C5 | C6 | C7 | C8 | C9 |
| DEGRADE MAX | 20 | 20 | 20 | 20 | 20 | 20 | 20 | 20 | 20 |
| FOLWING PULS DVSR | 0 | 0 | 0 | 0 | 3 | 4 | 4 | 0 | 0 |
| FOLWNG PULS NOMNL WIDTH | −1 | −1 | −1 | −1 | 20 | 40 | 40 | −1 | −1 |
| MULT PK HI THRSH | .8 | .8 | .8 | .8 | .8 | .8 | .8 | .8 | .8 |
| MULT PK LO THRSH | .3 | .3 | .3 | .3 | .3 | .3 | .3 | .3 | .3 |
| OPOS PULS ABSNT | 0 | 0 | 0 | 0 | 15 | 15 | 15 | 0 | 0 |
| OPOS PULS PRSNT | 5 | 5 | 5 | 7 | 0 | 0 | 0 | 5 | 5 |
| PEAK THRSH | 1 | 1 | 1 | 1 | .6 | .6 | .6 | 1 | 1 |
| POST R.M.S. MAX INTVL | 26 | 26 | 26 | 26 | 26 | 26 | 26 | 26 | 26 |
| PRIM PULS DVSR | 4 | 1 | 1 | 3 | 2 | 3 | 3 | 3 | 2 |
| PRIM PULS NOMNL WIDTH | 32 | 13 | 13 | 20 | 10 | 20 | 20 | 40 | 20 |
| PRIM PULS UPPER WIDTH LIM | 0 | 0 | 0 | 6 | 0 | 0 | 0 | 0 | 0 |
| R.M.S. DVSR | .06 | .06 | .06 | .05 | .06 | .06 | .06 | .04 | .05 |
| R.M.S. EXP | 1 | 1 | 1 | 1 | 1 | 1 | 1 | 1 | 1 |

TABLE 3-continued

WIDE PULSE SUBROUTINE

| PARAMETERS | PROB 2 | | | PROB 3 | | | | | |
|---|---|---|---|---|---|---|---|---|---|
| | C1 | C2 | C3 | C4 | C5 | C6 | C7 | C8 | C9 |
| SEPRATN DVSR | 5 | 5 | 5 | 5 | 5 | 5 | 5 | 5 | 5 |
| SEPRATN EXP | 2 | 2 | 2 | 2 | 2 | 2 | 2 | 2 | 2 |
| SEPRATN HI LIM | 26 | 26 | 26 | 26 | 26 | 26 | 26 | 26 | 26 |
| SEPRATN LO LIM | 7 | 4 | 4 | 7 | 5 | 5 | 5 | 7 | 7 |
| TOTL DVSR | 0 | 0 | 0 | 0 | 0 | 0 | 0 | 0 | 0 |
| TOTL EXP | 0 | 0 | 0 | 0 | 0 | 0 | 0 | 0 | 0 |
| TOTAL PULS | −1 | −1 | −1 | −1 | −1 | −1 | −1 | −1 | −1 |
| NOMNL WIDTH | | | | | | | | | |
| UPPER WIDTH THRSH | .6 | .6 | .6 | .6 | .6 | .6 | .6 | .6 | .6 |
| WIDTH EXP | 1.5 | 1 | 1 | 1 | 1 | 1 | 1 | 1 | 1 |
| WIDTH THRSH | .05 | .05 | .05 | .05 | .1 | .06 | .06 | .1 | .05 |
| XTRA PKS DESIRD | 0 | 0 | 0 | 0 | 0 | 0 | 1 | 0 | 0 |

TABLE 4

SURGE SUBROUTINE

| PARAMETERS | PROB 1, C3 |
|---|---|
| DEGRADE MAX | 10 |
| ZERO CROS DVSR | 1.5 |
| ZERO CROS EXP | 1 |
| ZERO CROS LO LIM | 2 |
| ZERO CROS NOMNL | 8 |
| ZERO CROS THRSH | 4 |

TABLE 5

LOOSE ELECTRODE SUBROUTINE

| PARAMETERS | PROB 1, C4 |
|---|---|
| DEGRADE MAX | 6 |
| FOLWNG PK THRSH | 1 |
| WIDTH LO LIM | 26 |
| WIDTH THRSH | .08 |
| ZERO CROS DVSR | 2 |
| ZERO CROS EXP | 1 |
| ZERO CROS HI LIM | 10 |
| ZERO CROS NOMNL | 2 |
| ZERO CROS THRSH | .1 |

TABLE 6

LOOSE PROBE/RUB STRIP SUBROUTINE

| PARAMETERS | PROB 1 | | PROB 2 | | PROB 3 |
|---|---|---|---|---|---|
| | C5 | C6 | C8 | C7 | C10 |
| DEGRADE MAX | 13 | 13 | 13 | 13 | 13 |
| R.M.S. DVSR | .15 | .1 | .1 | .15 | .1 |
| R.M.S. EXP | 1 | 1 | 1 | 1 | 1 |
| R.M.S. LO LIM | .5 | .3 | .3 | .5 | .3 |
| R.M.S. NOMNL | .1 | .5 | .5 | .1 | .5 |
| ZERO CROS DVSR | 2 | 4 | 4 | 2 | 4 |
| ZERO CROS EXP | 1 | 1 | 1 | 1 | 1 |
| ZERO CROS HI LIM | 35 | 99 | 99 | 35 | 99 |
| ZERO CROS LO LIM | 8 | 21 | 21 | 8 | 21 |
| ZERO CROS NOMNL | 21 | 45 | 45 | 21 | 60 |
| ZERO CROS THRSH | .3 | .3 | .3 | .3 | .3 |

TABLE 7

ABNORMAL A/B CHOP SUBROUTINE

| PARAMETERS | PROB 3 C11; C12 |
|---|---|
| DEGRADE MAX | 12 |
| HI NOISE LIM | 15 |
| HI NOISE NOMNL | 30 |
| HI NOISE THRSH | 1.06 |
| LO NOISE INTVL LIM | 22 |
| LO NOISE NOMNL | 5 |
| LO NOISE LIM | 10 |
| LO NOISE THRSH | 1.12 |
| PEAK THRSH | .8 |
| R.M.S. DVSR | .1 |

TABLE 7-continued

ABNORMAL A/B CHOP SUBROUTINE

| PARAMETERS | PROB 3 C11; C12 |
|---|---|
| R.M.S. EXP | .1 |
| R.M.S. NOMNL | .6 |
| R.M.S. LO LIM | .3 |
| ZERO CROS DVSR | 2 |
| ZERO CROS EXP | 1 |

TABLE 8

NORMAL A/B CHOP SUBROUTINE

| PARAMETERS | PROB 3 C13 |
|---|---|
| DEGRADE MAX | 15 |
| LO WIDTH DVSR | 5 |
| LO WIDTH EXP | 1 |
| LO WIDTH LIM | 8 |
| LO WIDTH NOMNL | 25 |
| LO WIDTH THRSH | .1 |
| PEAK THRSH | .5 |
| POST INTVL LO LIM | 26 |
| R.M.S. DVSR | .07 |
| R.M.S. EXP | .1 |
| R.M.S. HI LIM | .3 |
| R.M.S. NOMNL | 0 |
| UPPER WIDTH DVSR | 2 |
| UPPER WIDTH EXP | 1 |
| UPPER WIDTH LIM | 10 |
| UPPER WIDTH NOMNL | 4 |
| UPPER WIDTH THRSH | .6 |

TABLE 9

ACCEL/DECEL SUBROUTINE

| PARAMETERS | PROB 3 C14 |
|---|---|
| DEGRADE MAX | 10 |
| R.M.S. DVSR | .1 |
| R.M.S. EXP | 1 |
| R.M.S. NOMNL | .8 |
| WIDTH DGRD | 4 |
| WIDTH LO LIM | 6 |
| WIDTH THRSH | .08 |
| ZERO CROS DVSR | 2 |
| ZERO CROS EXP | 1 |
| ZERO CROS NOMNL | 10 |
| ZERO CROS THRSH | .1 |

Primary Pulse Width

If the sign is correct, an affirmative result of test 2 reaches a series of steps 3 in which: the beginning sample is set equal to the threshold sample; a threshold value for use in the width/peak subroutine 4 is set equal to the width threshold (which may vary as set forth in Table 2 hereinafter); and the width A.G.C. command is set. Then the width/peak subroutine 4 is called, the output of which includes the beginning sample of the primary pulse, the end sample of the primary pulse, and a threshold varied with A.G.C.. For use later in the narrow pulse subroutine, local factors are retained in a series of steps 5: a pulse beginning sample, an end sample, and A.G.C. threshold are set equal to the beginning sample; end sample, and A.G.C. threshold found in the subroutine 4. The final pair of steps 5 provide a beginning of the post-R.M.S. interval equal to the pulse end sample, and the end of the post-R.M.S. interval as a maximum sample, for use later on in the subroutine, regardless of which way the subroutine advances. Then a test 6 determines if a pre-R.M.S. divisor is greater than unity. Referring to Table 2, it can be seen that the parameters for probe 2, category 5 include a pre-R.M.S. divisor of 1.04. Having a value greater than one identifies the fractional portion of the pre-R.M.S. divisor as an A.G.C. multiplicand. Thus, if test 6 is affirmative (which it would be in the case of probe 2, category 5), a step 8 will provide, for internal use, a pre-R.M.S. divisor equal to the product of the fractional portion provided to the subroutine times the absolute value of the magnitude of the peak of the primary pulse found by the width/peak subroutine 4. The same applies with respect to the post-R.M.S. divisor which is greater than one for category 5 of probe 2 as well as for category 3 of probe 3. In such case an affirmative result of test 9 causes the post-R.M.S. divisor to be reconstituted in step 10 to be equal to the product of the fractional portion of the divisor times the absolute value of the magnitude of the peak of the primary pulse as determined by the width peak routine of FIG. 2. For other categories against which a sample record is being compared by the narrow pulse routine, the steps 8 and 10 are bypassed.

In FIG. 25a, a test 12 compares the width of the pulse determined by the width/peak subroutine 4 with a primary pulse width limit. If the pulse is too wide, an affirmative result of test 12 will cause the calling program to be reverted to through a return point 13. Otherwise, the category is degraded on width by a plurality of steps 14 setting: the measured parameter equal to the width of the pulse found by the width/peak subroutine 4; the nominal factor equal to the primary pulse nominal width of Table 2; the degradation equal to the width exponent of Table 2; and the sensitivity equal to the primary pulse divisor of Table 2. Then the degrade subroutine 15 is called and the degrade factor is updated for this sample record as a consequence.

Following Peak

In the next part of the narrow pulse subroutine in FIG. 25a, a search is made for a following peak. A series of steps 16 establish the criteria for the search: setting the local pulse end sample value equal to the end sample plus one (one sample higher in number than the sample identifying the end of the primary pulse as defined by the width/peak subroutine 4); setting the beginning sample for the search equal to the pulse end; setting the end sample for the search equal to the maximum sample (sample number 104 in the present example); resetting the reverse command (so that a forward search will be made at sucessively higher sample numbers); setting the sense command equal to zero, meaning that either positive or negative following pulses should be recognized; and setting the threshold equal to the following peak threshold of Table 2. Then the following peak subroutine 18 is called.

Figure 26:
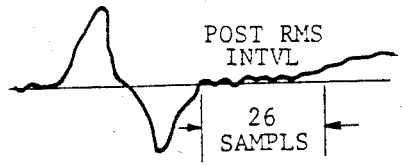
Figure 27:
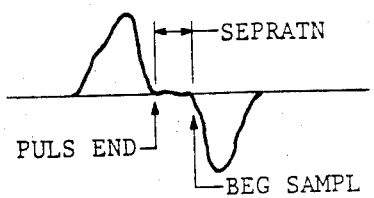

The program continues in FIG. 25b by a test 19 which determines if a following peak has been found. If S peak is equal to zero, this means no following peak has been found, so an affirmative result of test 19 will reach a step 20 in which the degradation value is updated by adding to it some penalty factor for the opposite pulse being absent, as in Table 2. In Table 2, only three categories show a desire for a following pulse of opposite polarity, the other four categories are indifferent to that fact. If there is a following peak, a negative result of test 19 will reach a series of steps 21 which set up the characteristics for performing the width/peak subroutine 22 with respect to the following pulse the beginning sample is set to the sample of the peak of the following pulse; the threshold is set equal to the A.G.C. threshold determined in performance of the width/peak subroutine 4 (FIG. 25a); and the width A.G.C. command is reset (so that the next performance of the width/peak subroutine 22 will not perform A.G.C. on the threshold and will only pass through one time). Following performance of the width/peak subroutine 22 in FIG. 25b, a step 23 defines the separation (as shown in FIG. 27) between the primary pulse and the following pulse as the difference between the beginning sample of the following pulse and the pulse end (one sample higher than the end of the primary pulse as set in step 5 of FIG. 25a). Then a step 24 determines if the following pulse is of the same polarity as the primary pulse (FIG. 28), or if it is of the opposite polarity thereto (FIG. 26). This is achieved by multiplying the sign of the primary pulse for the category being examined times the value of the peak of the following pulse. If they are of opposite polarity, the product will be negative and an affirmative result of test 24 will reach a test 25 to determine if the separation between the pulses is greater than an opposite pulse separation low limit (FIG. 27). This is because a following pulse of an opposite polarity in a recognized category (such as those illustrated, for example, in FIGS. 57 and 58) will typically be overshoots of the primary pulse. If they are overshoots, they should be very close together. Reference to Table 2 shows that a three sample limit has been found reasonable to test for overshoots. On the other hand, if the separation is greater than the opposite pulse separation low limit, this means that the following pulse is not related to the primary pulse, and that the primary pulse is therefore isolated.

Figure 28:
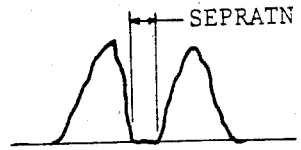
Figure 29:
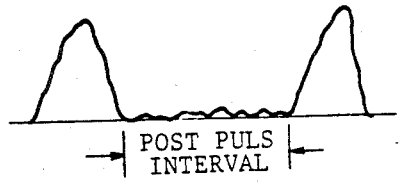
Figure 30:
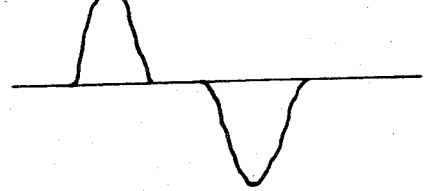

In FIG. 25b, if the result of test 24 is negative, a step 26 will degrade the pulse by the opposite pulse absent degradation factor, which is seen to be significant in three of seven categories in Table 2. These are categories which require overshoot in all cases. And then a test 27 determines if separation is less than a same polarity separation low limit, as seen in FIG. 28. Reference to Table 2 shows that this is a somewhat higher limit ranging from seven to thirteen samples in width. If pulses of the same polarity are too close together, this belies the isolated syntactic narrow pulse which relates to the categories which can satisfy the narrow pulse subroutine of FIG. 25. Therefore, an affirmative result of test 27 will cause the calling subroutine to be reverted to through a return point 28, rejecting the present category as a contender. But if the pulses are either of the same polarity and suitably separated, or if opposite polarity and suitably separated, then either a negative result of test 27 or an affirmative result of test 25 will reach a test 29 to see if the pulses are so sufficiently separated that no degradation results from having two isolated pulses in the same sample record, as shown for two positive pulses in FIG. 29. In test 29, the separation of the pulses is compared against a separation high limit, which is twenty six samples in all of the examples of Table 2. This is because any additional pulses which are truly separated from the primary pulse are of no interest in classifying the pulse one way or the other, they are simply additional events which have been sensed or they are rapid repeats of the same event. On the other hand, if the pulses are less than 26 samples apart as seen in FIG. 30, then degradation is effected, depending on how much closer than 26 samples apart they are, by a negative result of test 29 reaching a series of steps 30 which set up the characteristics for running the degrade subroutine 31. Specifically: the measured value is set equal to separation; the nominal value is set equal to the separation high limit (the same value used in test 29); the degradation is set equal to the separation exponent and the sensitivity is set equal to the separation divisor, all as set forth in Table 2 for the various categories. Then the sample record is degraded by the degrade subroutine 31.

Figure 31:

In FIG. 25b, if the pulses are of opposite polarity and sufficiently close together so as to be considered to be a primary pulse with an overshoot, a negative result of test 25 will reach a step 32 which updates the end of the pulse to be the end of the opposite polarity pulse by causing the pulse end to be set equal to one greater than the end sample determined for the following pulse in the width/peak subroutine 22. Since the primary pulse and the opposite polarity following pulse have been determined to be a single pulse, separation is not a degradation factor, but rather the width of the following pulse is. And then the width is compared in a test 33 against a following pulse width limit to be sure it is no wider than the permitted overshoot for the particular category under consideration. If the overshoot is too wide as shown in FIG. 31, then the calling program is reverted to through a return point 33a. But if the overshoot is within limits, a negative result of test 33 reaches a plurality of steps 34 to establish the characteristics for degrading the sample record on following-pulse-width by calling the degrade subroutine 35. In steps 34, the measured value is set equal to the width of the following pulse as found in the width/peak subroutine 22: the nominal value is set equal to the following pulse nominal width; the degradation is set equal to the width exponent; and the sensitivity is set equal to the following pulse divisor, all as set forth in Table 2 for the various categories. Then, the degrade subroutine 35 is called to degrade the pulse based upon the width of the overshoot.

Post Pulse R.M.S. Noise

In FIG. 25b, following either of the appropriate degrade subroutines 31, 35, the end of the post-pulse R.M.S. interval is redefined, in the case where there is a following pulse. If the following pulse is a separate pulse, the post-pulse R.M.S. interval is the separation between the two pulses. Therefore, in a step 36, the end of the post-R.M.S. interval is set equal to the minimum of either the maximum sample or one less than the beginning sample of the following pulse, as in FIG. 29. On the other hand, if the following pulse is simply an overshoot of the primary pulse, then the post-pulse R.M.S. interval extends beyond the overshoot. However, to guard against the case where the wave shape may have a slowly increasing D.C. component near the end of the sample record, a maximum post-R.M.S. interval (seen in Table 2 to be 26 samples for the exemplary categories herein) is examined. This begins at the end of the composite pulse (including the primary pulse and the following pulse overshoot) and can extend no farther than the post-R.M.S. maximum interval, as seen in FIG. 26. Thus, the minimum is taken in a step 37 because the post-R.M.S. interval added to the pulse end could possibly extend beyond the end of the entire record (particularly in the case of downstream probes whose records have been captured at a time frame dependent upon the exceedance of a threshold by an upstream probe). On the other hand, in FIG. 25b, if there were no following pulse, the affirmative result of test 19 passing through step 20 leaves the end of the post-pulse R.M.S. interval equal to the maximum sample as set in step 5 of FIG. 25a.

The narrow pulse subroutine continues in FIG. 25c by presetting the pre-pulse R.M.S. value and post-pulse R.M.S. value to zero, in steps 38. Then a test 39 determines if the pulse beginning is greater than 1. If it is not, there is no pre-pulse R.M.S. interval and so no R.M.S. value can be obtained therefor. But if it is greater than 1, steps 40 set the beginning sample equal to 1 and the end sample equal to the pulse beginning of the primary pulse, which was saved in the first of the steps 5 in FIG. 25a, following the first utilization of the width/peak subroutine 4. In FIG. 25c, following the steps 40, the R.M.S. program 41 is called to provide an indication of the magnitude of R.M.S. noise before the primary pulse. This is saved as the pre-pulse R.M.S. value in a step 42. Then a test 43 determines if the end of the post-R.M.S. interval is greater than either the end of the primary pulse which is established a pulse end in the second of the steps 5 in FIG. 25a, or the end of a composite pulse with overshoot, which is saved in a step 32 in FIG. 25b. If it is not, there is no post-R.M.S. interval so no R.M.S. value can be obtained. But if the end of the post-R.M.S. interval is at a higher sample number than the end of the primary or composite pulse, the beginning sample is set equal to the end of the pulse and the end sample is set equal to the end of the post-R.M.S. interval, in a pair of steps 44. Then the R.M.S. subroutine 45 is called and the R.M.S. noise value is saved in a step 46 as the post-pulse R.M.S. value.

Figure 32:
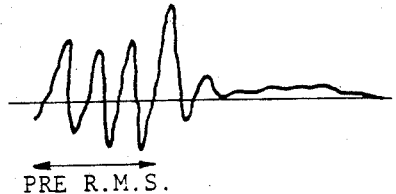
Figure 33:
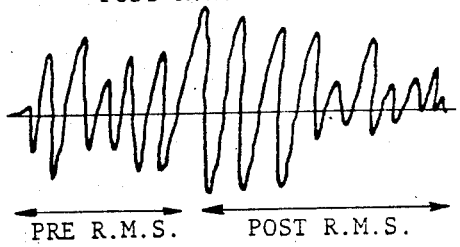

In FIG. 25c, a series of steps 47 set up the criteria for degrading the pulse on the basis of pre-pulse R.M.S.. The measured value is taken as the pre-pulse R.M.S. value: the nominal value is set equal to zero; the degradation is set equal to the R.M.S. exponent of Table 2; and the sensitivity is set equal to the pre-pulse R.M.S. divisor of Table 2. Then the degrade subroutine 48 is called. Degrading of the pulse on its post-pulse R.M.S. noise is achieved by steps 49 setting the measured quantity equal to the post-R.M.S. noise and the sensitivity equal to the post R.M.S. divisor, followed by calling the degrade subroutine 50 once again. The pre- and post-pulse R.M.S. noise provides a discriminant against gross signals with a sufficient, narrow pulse in them, such as shown in FIG. 32 and FIG. 33; these may be examples of abnormal afterburner chop (FIG. 78) and rub strip peel-off (FIG. 62), respectively.

In the narrow pulse subroutine of FIG. 25, degradation occurs, for any given record sample to which the subroutine is applied on four or five different parameters: first, the primary pulse width (14, 15); opposite pulse absent (20); or following pulse width (34, 35), or separation (30, 31); third, if there is a following pulse of the same polarity, it may additionally be degraded for opposite pulse absent (26); fourth, it is degraded for pre-and post-R.M.S. (47–50). Thus there may be a significant degradation number following the R.M.S. degradation in FIG. 25c.

In order to determine the relative degree to which any particular record sample fits a category for which the narrow pulse subroutine has been called, the quality factor, Q, is calculated in a step 51 in FIG. 25c. This is determined by subtracting from unity the ratio of the degradation which has occurred to the maximum degradation which can occur. The maximum degradation which can occur for the various categories is set forth at the top of Table 2. Then, in case the degradation has exceeded maximum degradation, a test 52 determines if Q is less than zero. If it is, a step 53 sets Q for the given category equal to zero; if not, a step 54 sets Q for the particular category equal to the value of Q calculated in step 51. And then the calling subroutine (one of FIG. 10–FIG. 12) is reverted to, through a return point 55.

WIDE PULSE SUBROUTINE—FIG. 34

Pulse Width

The wide pulse subroutine of FIG. 34 is similar to the narrow pulse subroutine of FIG. 25, in many respects. The wide pulse subroutine is reached in FIG. 25a through an entry point 1 and a plurality of steps 2: reset an opposite following pulse flag; set the width A.G.C. command; set the beginning sample equal to the sample of record threshold crossing; and set the threshold equal to the width threshold of Table 3, for the particular parameter being examined. Then a test 3 determines whether or not the present sample set is of the correct polarity for the category being tested for, as is set in steps 8 or 11 of FIG. 11 or steps 21 or 22 of FIG. 12, as the case may be. If the value at the threshold sample is of the wrong polarity, a negative result of test 3 will cause the program to revert to the calling routine through a return point 4, thus rejecting the particular category as a candidate for this record sample. But if the polarity is correct, an affirmative result of test 3 will reach the width/peak subroutine 5. The parameters determined in the width/peak subroutine 5 are saved for later use in the wide pulse subroutine, in a series of steps 6: the pulse beginning sample is set equal to the beginning sample determined in the subroutine 5; the pulse end sample is set equal to the end sample determined in the subroutine 4; the primary pulse width is set equal to the width determined in the subroutine 5; the primary pulse width is set equal to the width determined in the subroutine 5; the total pulse width is set equal to the width determined in the subroutine 5; an R.M.S. divisor is given A.G.C.-type treatment by multiplying it by the value of the peak found in the subroutine 5; the value of the peak of the primary pulse is set equal to the value of the peak sample found in the subroutine 5; and the A.G.C. width threshold is memorized as the threshold determined (with the width A.G.C. command set) in the subroutine 5. Then a test 7 determines if the primary pulse upper width limit is zero or not. Reference to Table 3 shows that only category 4 of probe 3 requires a minimum width at the upper extremity of the pulse since it is the only category of the present example which has a non-zero primary pulse upper width limit. An example of category 4 for probe 3 is illustrated in FIG. 72. If the primary pulse upper width limit is non-zero, a negative result of test 7 reaches a series of steps 8 wherein the beginning sample is set equal to the sample number of the peak found in the subroutine 5; the threshold is set equal to the upper width threshold times the absolute value of the magnitude of the peak found in the subroutine 5; and the width A.G.C. is reset. Then the width/peak subroutine 10 is called to determine the width of the upper part of the pulse. The width determined in the subroutine 10 is compared in a test 11 with the primary pulse upper width limit (see FIG. 35) as set forth in Table 3, which is a low limit on what should be a rather square pulse (e.g., the uncorrelated-2 category of FIG. 71), and if the width is not adequate, an affirmative result of test 11 will cause the calling routine to be reverted to through a return point 12. If desired for further discrimination between categories (e.g., to reject normal afterburner chop, FIG. 79), upper width limits may be added to more of the categories in Table 3. In the event that there is no constraint on the upper width, an affirmative result of test 7 will bypass the portion of the program 8–12 relating to the upper width.

Following Pulse

Figure 34A:
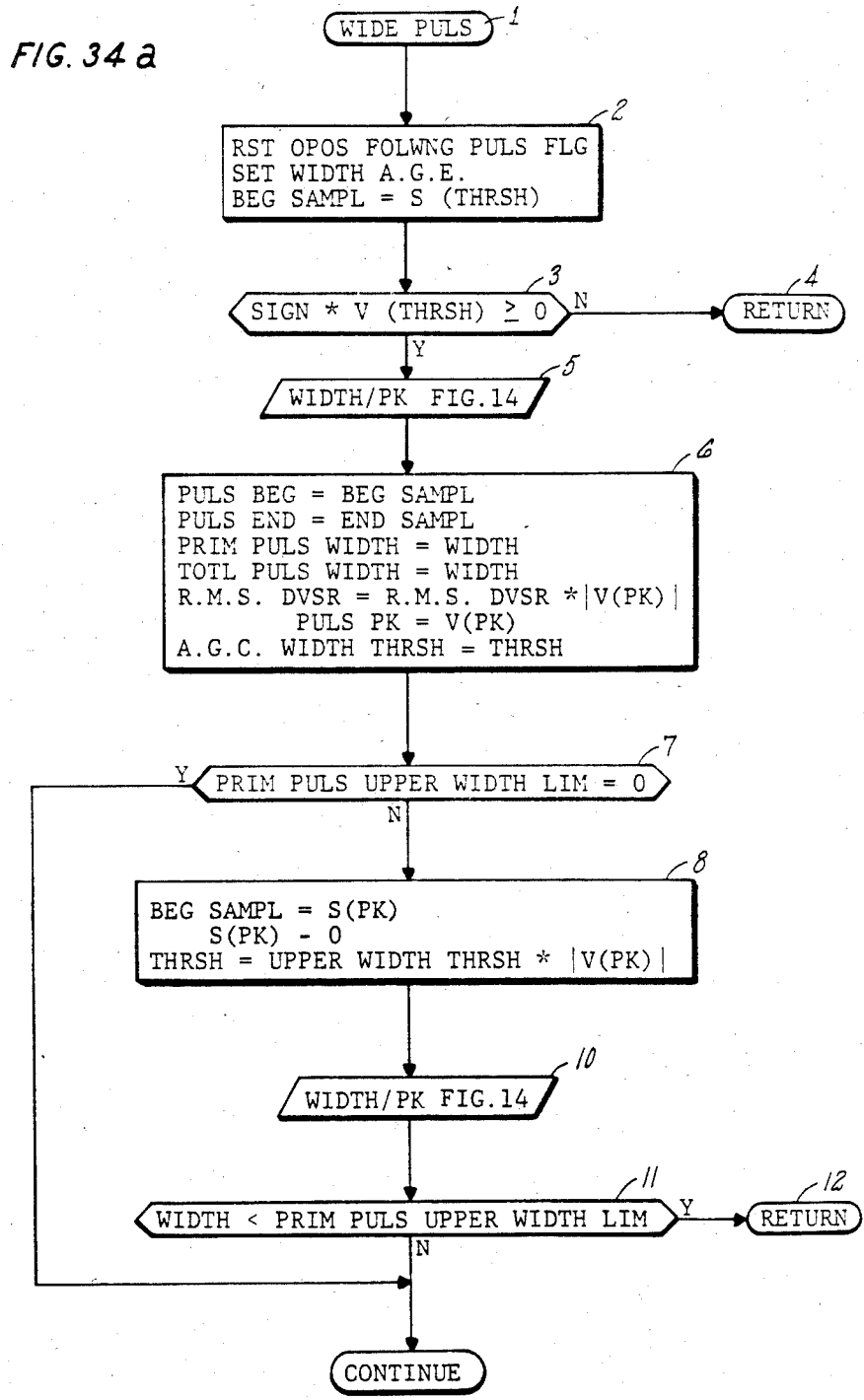
Figure 34B:
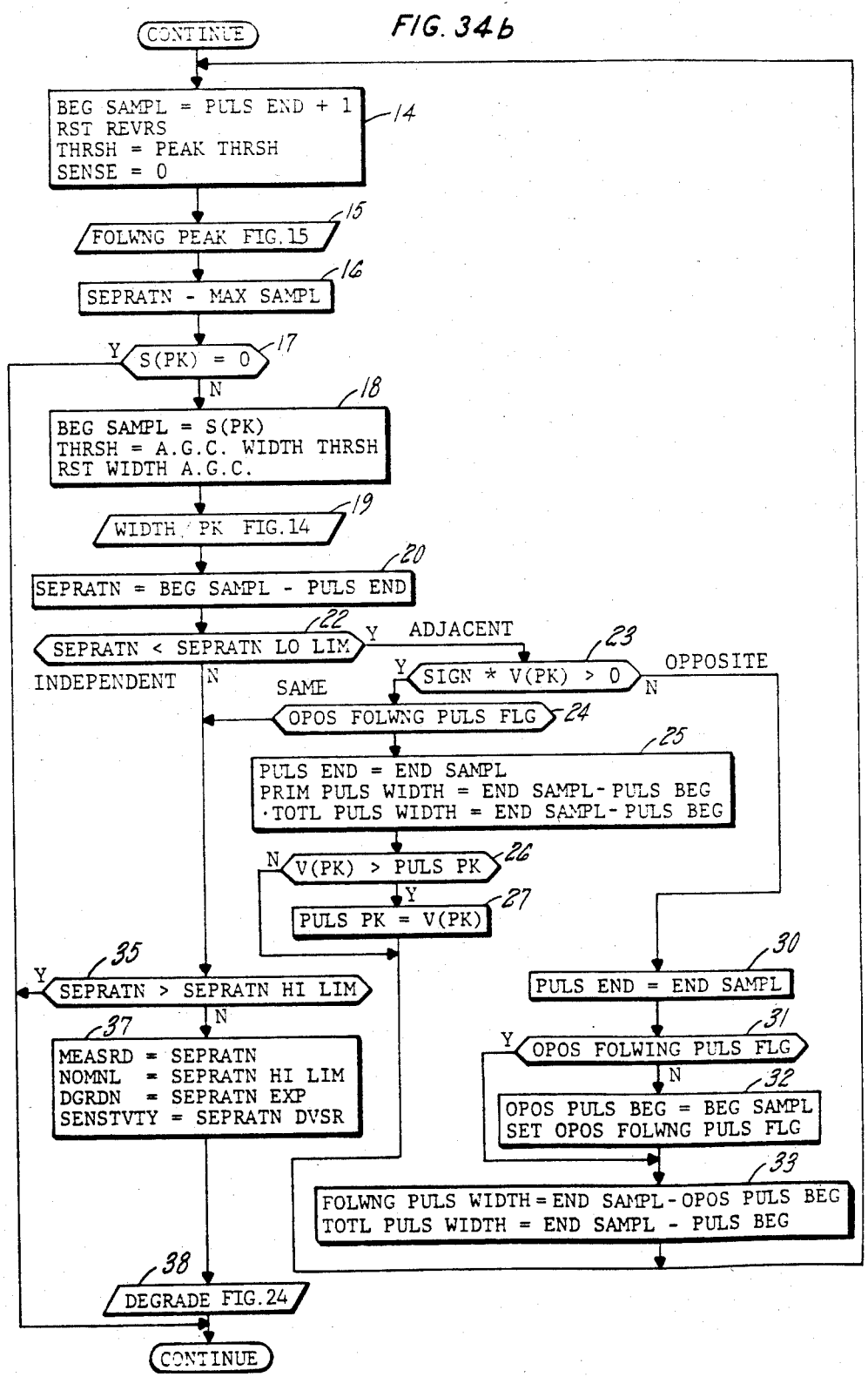

The wide pulse subroutine continues in FIG. 34b with a series of steps 14 that: set a beginning sample equal to one sample higher than the normal end of the primary pulse, as found in subroutine 5 and memorized in the second of the steps 6; the reverse flag is reset, so that the next peak to the right (or higher sample number) will be searched for; a threshold is set equal to the peak threshold of Table 3; and the sense command is set to zero, meaning that either a positive-going or a negative-going following pulse should be recognized; then the following peak subroutine 15 is called, after which separation is preset in a step 16 to be equal to the maximum sample (104 in this example).

In FIG. 34b, a test 17 determines if a following peak has been found or not. If the sample number of the peak is equal to zero, this means that no following peak has been found. Otherwise, a negative result of test 17 will reach a series of steps 18 in which: the beginning sample is set equal to the sample of the peak found for the following peak in the subroutine 15; the threshold is set equal to the A.G.C. width threshold provided by running the width/peak subroutine 5 in FIG. 34a; and the width A.G.C. is reset. Then the width/peak subroutine 19 is called and the separation is updated to be equal to the beginning sample of the following pulse (determined by the width/peak subroutine 19) minus the pulse end of the primary pulse (determined by the width/peak subroutine 5, FIG. 34a, and memorized in the second of the steps 6 in FIG. 34a in a step 20), as shown in FIG. 36.

The next portion of the wide pulse subroutine in FIG. 34b concerns itself with three aspects of pulse shapes in the sample record. First, the primary pulse may be wider than the width determined by the width/peak subroutine (5, FIG. 34a). This can occur if there is a false dip in the pulse as a consequence of noise. This phenomenon may be visualized by considering the wave shape of high turbine first stage blade erosion shown in FIG. 63. Therein, if the positive going spike in the middle of the negative pulse were a little more positive as in FIG. 82, it could fall within the pulse width threshold and the width would have been determined to be about half of the true width. Thus, the subroutine of FIG. 34b senses closely adjacent following pulses of the same polarity as being part of the primary pulses; it then concatenates the two pulses and recomputes the overall pulse width. A second feature which the subroutine of FIG. 34b is concerned with is that some categories (such as those shown in FIG. 63–FIG. 65) do not normally have following pulses, so the presence of a following pulse is utilized as a degradation factor for the given category, unless the following pulse is widely separated from the preceding pulse, in which case it can be ignored as a separate, unrelated event as in FIG. 38. And finally, if there is a following pulse of an opposite polarity, and then a third pulse of the original polarity, the third pulse is treated as an independent pulse, as in FIG. 39. Whenever two, closely adjacent pulses of the same polarity are concatenated (whether primary or opposite, following pulses), the search for further pulses must continue (as in FIG. 38).

In FIG. 34b, a test 22 determines if the separation between the primary pulse and the following pulse is less than a separation low limit provided from Table 3 by the calling routine. Generally, the wider the pulse of any category can be, the larger the separation can be and still consider the pulses to be adjacent. If the pulses are adjacent, an affirmative result of test 22 will reach a test 23 to see if the sign of the peak value of the following pulse is the same as the sign for the category being tested (remembering that the program exits at the top of FIG. 25a if the primary pulse is not of the correct category sign). Assuming that the pulses are of the same polarity, an affirmative result of test 23 reaches a test 24 which determines if this is a third pulse following a second pulse of opposite polarity to the primary pulse, as in FIG. 39. Initially, the opposite following pulse flag is always reset (steps 2, FIG. 34a) so that a negative result of test 24 will reach a series of steps 25 in FIG. 34b, to concatenate the pulses, as in FIG. 37. First, the pulse end (initially set at the end of the primary pulse) is now updated to be equal to the end sample of the following pulse, as determined by the width/peak subroutine 19 (FIG. 34b). The primary pulse width (previously retained in steps 6 as the width of the primary pulse found in the width/peak subroutine 5, FIG. 34a) is recomputed as being the interval from the end sample of the following pulse to the beginning sample of the primary pulse; the total pulse width is similarly recomputed. Then the peak magnitude of the following pulse (from the subroutine 19, FIG. 34b) is compared in a test 26 with the pulse peak retained as the peak value of the primary pulse (5, 6, FIG. 34a). If the second part of the pulse has a higher peak as in FIG. 38, the pulse peak is updated in a step 27; otherwise, step 27 is bypassed.

At this point of the subroutine of FIG. 34b, the description has assumed that there has been a pair of closely adjacent pulses of the same sign. Therefore, the primary pulse has been updated to include both of them. Now it is still necessary to determine if there are any true following pulses of either the same or opposite sign. In the case of second probe categories 1, 2 and 3 (shown in FIGS. 62-64) following pulses are not desirable; in the case of third probe categories 5, 6 and 7 (illustrated in FIGS. 73-75) following pulses of an opposite sign are mandatory. Since the wide pulse subroutine is used for all of these catagories, it has the capability of going forward and looking for additional pulses.

The subroutine of FIG. 34b thus reverts to the steps 14 where the beginning sample for searching for a following peak is set one sample higher than the pulse end of the concatenated composite pulse. The steps and tests 14-20 are repeated to find a following pulse, and to determine its width and its peak value. Assume again that a closely adjacent following pulse is found, so that test 22 is again affirmative. Assume further that this pulse is opposite to the polarity of the primary pulse as in FIG. 40, so that test 23 is negative. In those cases (e.g., FIG. 72-FIG. 74) which require contiguous pulses of opposite polarity, the end of the overall pulse will be the end of the following, opposite pulse. Thus, a step 30 updates the pulse end to equal the end sample of the following pulse found in the most recent pass through the width/peak subroutine 19. Then a test 31 determines if the opposite following pulse flag has been set or not. Initially, it has not, so a negative result of test 31 reaches a pair of steps 32 where the opposite pulse beginning sample is set equal to the beginning sample found for the following pulse in the most recent pass through the width/peak subroutine 19; and, the opposite following pulse flag is set. Then, in steps 33, the following pulse width is calculated (see FIG. 40) as equal to the end sample of the most recently found following pulse minus the opposite pulse beginning: and, the total pulse width is updated as being equal to the end sample of the most recently found following pulse minus the pulse beginning which was established for the primary pulse (5, 6, FIG. 34a).

In the example being considered, it is assumed that there were two closely adjacent positive pulses (which were concatenated into a single, wider positive pulse) followed by an adjacent negative pulse (or vice versa). It is still possible that there is another closely adjacent negative pulse (FIG. 41) which may be concatenated with the one which was just found, or there may be an additional positive pulse (FIG. 39) or an independent negative pulse (FIG. 42). Therefore, the program reverts again to the steps 14, now setting the beginning sample equal to the pulse end of the third pulse which has been found. Then the steps and tests 14-20 are again repeated looking for a fourth pulse. Assuming that a fourth pulse is found and it is closely adjacent to the third one, test 22 will be affirmative reaching test 23. If this pulse is also opposite to the primary pulse, it can be concatenated with the third pulse simply by updating pulse end, following pulse width and total pulse width, in the steps 30 and 33. But the original opposite pulse beginning will be retained (FIG. 41) since the opposite following pulse flag 31 will be set and bypass the steps 32. On the other hand, if a fourth pulse is found which is of the same polarity as the primary pulse, after a following pulse of an opposite polarity (FIG. 39), an affirmative result of test 23 will reach test 24 which is affirmative, thereby treating the additional pulse as being independent (just the same as if it were not adjacent to the opposite pulse). Whenever either test 22 (FIG. 42) or test 24 (FIG. 39) identifies an independent pulse (regardless of polarity), the subroutine of FIG. 34b reaches a test 35 which determines if the independent pulse is sufficiently separated from the pulses of interest to be irrelevant in the classifying process, as in FIG. 38. If so, the separation is greater than the separation high limit (Table 3), and an affirmative result of test 35 will bypass degradation as a function of an independent pulse. If the pulse is too close (less than the separation high limit) as in FIG. 42, then a negative result of test 35 causes a series of steps 37 to establish the characteristics for degrading this category inversely with the extent to which the separation between the pulses of interest and the independent pulse is less than the separation high limit. And the degrade subroutine 38 is called.

In FIG. 34b, any time the subroutine returns to the steps 14 and calls the following peak subroutine 15, if no peak is found, test 17 will be affirmative thus bypassing test 35 and the degradation 37, 38.

Figure 34C:
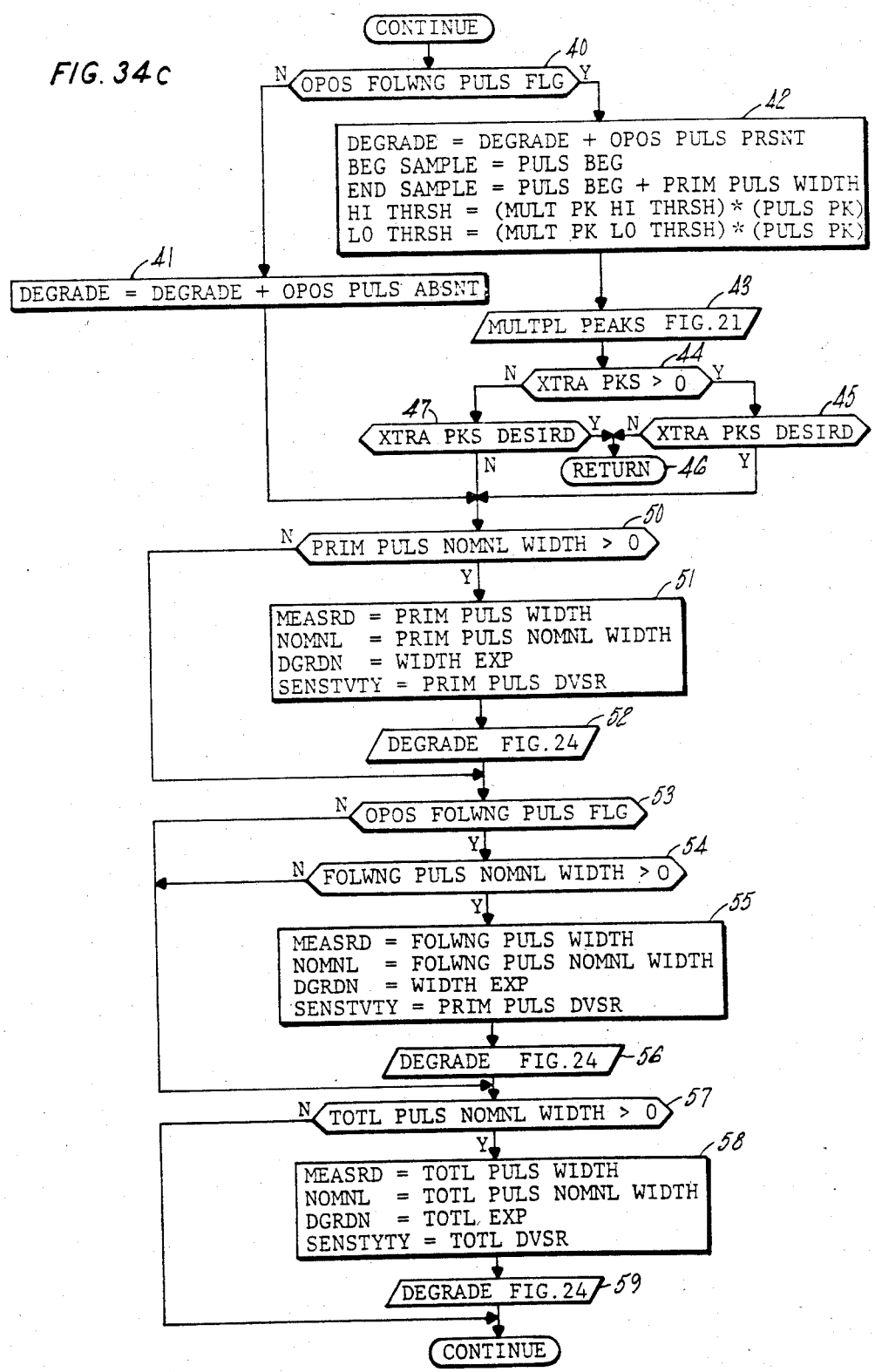

The wide pulse subroutine continues in FIG. 34c with a test 40 which determines if the opposite following pulse flag was set, or not. The third probe categories 5-7 (illustrated in FIGS. 73-75) are heavily dependent upon there being an opposite following pulse. Reference to Table 3 shows that the opposite pulse absent degradation factor is set equal to 15 for these categories, which is significant compared to the degrade maximum of 20 for these categories. A negative result of test 40 will reach a step 41 which will heavily degrade these three categories if there is no opposite following pulse. The other categories which utilize the wide pulse subroutine do not require opposite following pulses. In FIG. 34c, if test 40 is affirmative, this reaches a series of steps which will degrade the category for those parameters for which an opposite pulse is not normally present. Reference to Table 3 shows that the opposite pulse present degradation factor is significantly smaller than the opposite pulse absent degradation factor; this means simply that although these categories do not require an opposite following pulse, the presence of one is only moderately indicative of category exclusion, so only a minor degradation is performed.

Multiple Peak Check

In FIG. 34c, the remaining steps 42 establish the conditions for searching for multiple peaks, as is required for third probe category 7, impact induced turbine rub (FIG. 74). This acts as a discriminant against the third probe categories 5 and 6 (FIG. 72 and FIG. 73) which are normal turbine rubs, in contrast with turbine rub induced by impact, of an engine fragment or ingested object, on the turbine. In the steps 42: the beginning sample is set equal to the pulse beginning (the beginning of the primary pulse set in steps 6 of FIG. 34a); the end sample is set equal to the pulse beginning summed with primary pulse width, thereby defining that the multiple peaks subroutine 43 will be performed across the samples of the primary pulse, whether concatenated from two adjacent pulses of the same polarity as in FIG. 42, or not; then a high threshold and a low threshold are calculated as the product of the pulse peak (established in step 6, 23a for a unitary pulse, and possibly updated in step 27 of FIG. 34b for a concatenated primary pulse) multiplied by a multiple peak high threshold and a multiple peak low threshold set as in Table 3. Notice that thresholds are provided for all of the categories that use the wide pulse subroutine: this is an example of the discrimination process which requires looking for multiple peaks regardless of which category is under consideration since the presence of multiple peaks will absolutely rule out all of the categories except third probe category 7: the only category in which extra peaks are desired (bottom of Table 3). In FIG. 34c, the multiple peaks subroutine 43 is called and a test 44 determines if extra peaks have been found or not. If extra peaks have been found, then a test 45 examines the extra peaks desired parameter (bottom of Table 3) to see if the category being examined requires extra peaks or not. If not, this rejects the category under consideration and the calling subroutine is reverted to through a return point 46. On the other hand, if test 44 is negative, then a test 47 determines if extra peaks are desired. If no peaks have been found but third probe category 7 is being considered, this rejects this category so the calling subroutine is reverted to through the return point 46.

Width Degradation

The portion of the wide pulse subroutine shown in the remainder of FIG. 34c provides width degradation. Program flexibility is achieved by defining any nominal width of Table 3 which is negative as a flag indicative of the fact that width degradation is not to be performed. Thus a test 50 determines if the primary pulse nominal width (Table 3) is greater than zero. If it is, steps 51 establish the conditions for degrading the primary pulse width by calling the degrade subroutine 52. But if the primary pulse nominal width is negative, the steps 51 and degradation routine 52 are bypassed. Then a test 53 determines if the opposite following pulse flag has been set or not. If it has, a test 54 determines if the following pulse nominal width is positive. If it is, then a series of steps 55 set up the conditions for degrading the category as a function of the width of the following pulse, by calling the subroutine 56. If either test 53 or test 54 is negative, the degradation on following pulse width (55, 56) is bypassed. Then a test 57 determines if a total pulse nominal width is positive. If it is, a series of steps 58 set up the conditions for degrading on total pulse width by calling the degrade subroutine 59. But if test 57 is negative, degrading on total pulse width (58, 59) is bypassed. Notice in Table 3 that the total pulse nominal width is indicated as being −1 for all of the categories which are examined by the wide pulse subroutine. This is indicative of the flexibility of the present embodiment: total pulse width may in some cases be a useful, discriminating degradation factor, although in the present examples it is not.

R.M.S. Noise

Figure 34D:
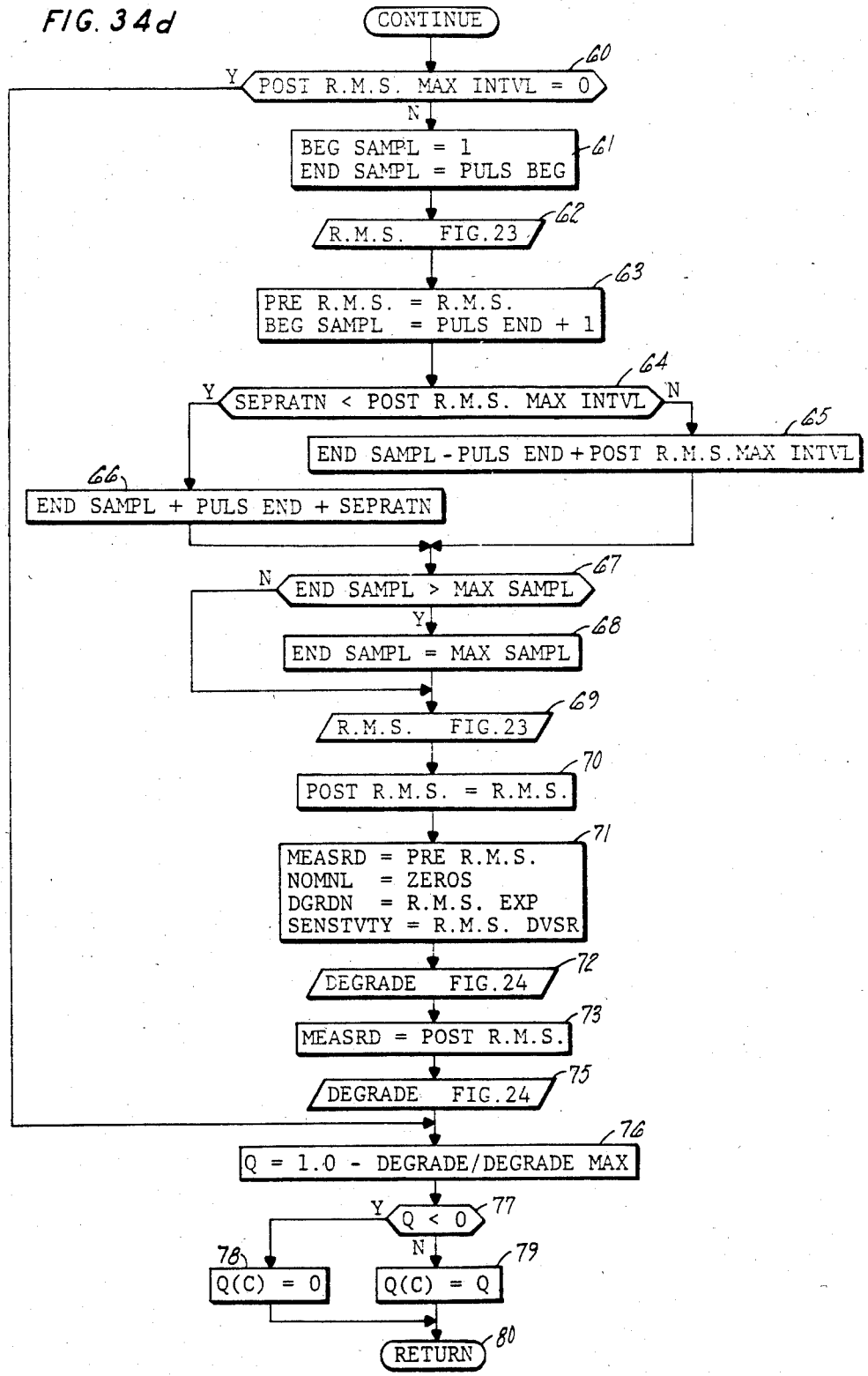

The remainder of the wide pulse subroutine illustrated in FIG. 34d is concerned with measuring the pre-pulse interval R.M.S. noise and the post-pulse interval R.M.S. noise. In the present example, pre and post-pulse R.M.S. noise is measured for all of the categories that utilize the wide pulse subroutine. However, such is not necessarily required; if R.M.S. noise is not of interest in some category other than the examples herein, measuring the R.M.S. noise and degrading the category accordingly can be sidestepped by setting the post-R.M.S. maximum interval (Table 3) to zero. Then a test 60 would be affirmative causing the subroutine of FIG. 34d to bypass the R.M.S. noise portions. In the examples herein, test 60 is negative and steps 61 set the beginning sample equal to 1 and the end sample equal the pulse beginning (of the primary pulse). This causes R.M.S. noise to be calculated by the subroutine 62 from the start of the record sample to the beginning of the primary pulse. In steps 63, the pre-R.M.S. interval is recorded as the R.M.S. value determined by the subroutine 62, and the beginning sample is updated to equal one sample greater than the pulse end. The pulse end is the end of the total pulse, and may be the end of a singular primary pulse as established in step 6 of FIG. 34a, or the end of a concatenated primary pulse as set in step 25 of FIG. 34b, or the end of a pair of opposite polarity, adjacent pulses as set in step 30 of FIG. 23b. The R.M.S. noise is polluted by the presence of an additional pulse following the pulse of interest. Therefore, the separation between pulses (if there is more than one pulse in a record) is compared with the post-R.M.S. maximum interval. The separation value used at this point in the subroutine may be 104 (the maximum sample) as set in step 16 of FIG. 34b, in the case where there are no independent pulses following a simple or concatenated primary pulse. When there is no independent following pulse, step 17 bypasses the remainder of FIG. 34b so the separation is set at the maximum sample (104 samples). On the other hand, when independent pulses are found by a negative result of test 22 or an affirmative result of test 24, the iterative process of FIG. 34b ends. Thus, any separation found in step 20 for concatenated or opposite pulses eventually is overwritten by the maximum sample of step 16, which is retained in the case that test 17 indicates no following peaks, or is further overwritten by step 20 when independent additional pulses are found. Thus it is, that the separation utilized in test 64 of FIG. 34d can only be the maximum sample or the separation between a pulse of interest and an independent pulse. In the general case, the separation will be that set in step 16 of FIG. 34b causing a negative result of test 64 to reach a step 65 in which the end sample is taken to be that which is separated from the end of the pulse by the post-R.M.S. maximum interval. The post-R.M.S. maximum interval is utilized to avoid taking R.M.S. noise at the highest sample numbers of a record sample having a relatively narrow pulse, since there is a tendency for an increase in D.C. drift that pollutes the R.M.S. noise factor at the high end of the sample (as described with respect to FIG. 26, hereinbefore).

If there is an independent following pulse, and if it is closer to the pulse of interest than the post-R.M.S. maximum interval, an affirmative result of test 64 in FIG. 34d will reach a step 66 in which the end sample is defined to be that just ahead of the following pulse. If either step 65 or step 66 sets the end sample too high, this will be detected by a test 67 which compares the defined end sample with the maximum sample. If it is too high, an affirmative result of test 67 will reach a step 68 where the end sample is simply set equal to the maximum sample. Otherwise, step 68 is bypassed. Then the R.M.S. subroutine 69 is called and the value determined therein is set as the post-R.M.S. value in a step 70. A plurality of steps 71 establish the conditions for degrading on the pre-pulse R.M.S. noise by calling the degrade subroutine 72, and then a step 73 establishes the same conditions but for degrading on post-pulse R.M.S. noise by calling the degrade subroutine 75.

In FIG. 34d, when R.M.S. noise has been considered, the sample record has its quality factor, Q, calculated in step 76 as unity minus the ratio of the accumulated degrade factor to the maximum degradation permitted for the category. If the degradation is more than the maximum, Q becomes negative, and a test 77 senses that and causes Q for the present category to be set equal to zero in a step 78. Otherwise, a negative result of test 77 reaches a step 79 where the Q for the category under consideration is set equal to the Q calculated in step 76. And then the calling program is reverted to through a return point 80.

SURGE SUBROUTINE—FIG. 43

The surge subroutine of FIG. 43 is utilized to recognize first probe category 3, compressor surge, as illustrated in FIG. 59. The waveform resulting from electrostatic charge during surge/stall conditions is characterized by a succession of large-amplitude swings, from positive to negative. Many of the swings are abrupt, occurring within one or two samples. It is detected by simply counting the number of swings of large amplitude (4 volts, Table 4). In FIG. 43, the surge subroutine is reached through an entry point 1 and a plurality of steps 2 set the beginning sample equal to the first sample of the record and the ending sample equal to the maximum sample; a threshold is set equal to the zero crossing threshold (Table 4) and the zero crossings subroutine 3 is called. The number of zero crossings determined by the subroutine 3 is compared in a step 4 with a zero crossing low limit (Table 4). If there are insufficient zero crossings, an affirmative result of test 4 causes the calling program to be reverted to through a return point 5, thus causing the Q for the surge category for the present record to remain zero.

In FIG. 43, if the record has an adequate number of zero crossings, a negative result of test 4 will reach a series of steps 5 to set up the conditions for degrading the category on the number of zero crossings by calling the degrade subroutine 6. And the quality factor for the surge category is determined as unity minus the ratio of the zero crossing degradation to the maximum degradation permitted for surge, in a step 7. Then a test 8 determines if the degradation has exceeded maximum, resulting in a negative value of Q. If so, an affirmative result of test 8 reaches a step 9 which sets Q for this category equal to zero. Otherwise, a negative result of test 8 reaches a step 10 where the value of Q for the surge category is set equal to the Q calculated in step 7. And then the calling program is reverted to through a return point 5.

Notice that the surge category is tested for only zero crossings. Comparison of the parameters in Table 4 for the surge subroutine with the parameters in Table 6 for the loose probe/rub strip subroutine indicate how surge can be recognized on the single parameter. Particularly, the frequency content is relatively low, having a nominal zero crossing of 8. Furthermore, the excursions must be rather violent, having a zero crossing threshold of 4 volts. This compares with much higher frequency content (nominal zero crossings of 45 and 60, etc.) with very low zero crossing thresholds (0.3) for the categories set forth in Table 6. Therefore, the soft degradation of the present invention becomes significant in determining whether first probe category 3 compressor surge or first probe category 5 abradable seal ingestion has been sensed by the first probe.

LOOSE ELECTRODE SUBROUTINE—FIG. 44

The loose electrode subroutine of FIG. 44 is utilized in searching for first probe category 4, as illustrated in FIG. 60, which is indicative of the electrode being loose within a probe (such as probes 1 and 2 in FIG. 1). The loose electrode wave shape is characterized by fairly long positive and negative excursions, at least one of which has to be longer than 20 milliseconds (26 samples, at a 1.3 KHz sampling rate), Table 5, WIDTH LO LIM. The excursions may be of varying magnitudes, and may have extremely low slopes of increasing and decreasing magnitude. The width detection is therefore difficult; this is accommodated by utilizing a width threshold which is a very small decimal fraction as an A.G.C. multiplicand against the value of the first peak of the pulse. Additionally, the portion of the wave shape which may have triggered the record threshold may be a very short duration excursion, the long duration excursion may follow it, as in the example set forth in FIG. 60: this is accommodated by looking for at least an additional pulse following the primary pulse.

In FIG. 44, the loose electrode subroutine is reached through an entry point 1, and a pair of steps 2 set the beginning sample equal to 1 and the end sample equal to maximum sample, for the purposes of performing the zero crossings subroutine 3. Then a series of steps 4 set the beginning sample equal to the sample number of the record threshold crossing, a threshold is set equal to the width threshold (of Table 5), and the width A.G.C. command is reset so that the width/peak subroutine 5 will only be passed through one time, simply to determine the peak value of the primary pulse. This is used in steps 6 to establish the threshold for actually determining the width of the primary pulse of the record, in a second calling of the width/peak subroutine 7. The steps 6 also reestablish the beginning sample for the width/peak subroutine 7 as the sample of the record threshold crossing (since the previous pass through the width/peak routine 5 established the beginning sample as the start of the pulse). And a following pulse flag, utilized elsewhere in FIG. 44 as described hereinafter, is reset. The A.G.C. threshold is provided externally of the width/peak subroutine to enable looking for the width of successive pulses, iteratively, in the subroutine 7. After the width/peak subroutine 7 is called, utilizing the A.G.C. width threshold, the width determined for the primary pulse is compared in a test 8 with a width low limit (Table 5). Assume for discussion that the width of the primary pulse is insufficient to identify a loose electrode wave shape. A negative result of test 8 will reach a test 9 to determine if the following pulse flag has been set or not. Initially, it has not been, because of having been reset in the steps 6. A negative result of test 9 reaches a series of steps 10 in which: the beginning sample (for the following pulse) is set equal to the end sample of the primary pulse determined from the preceding operation of the width/peak subroutine 7; the end sample is set equal to the maximum sample; the threshold is set equal to the following peak threshold; the sense command is set equal to zero, so that either positive or negative peaks can be found; and the reverse command is reset so that the following peak subroutine 11 will proceed rightwardly. If no following pulse is found by the subroutine 11, an affirmative result of a test 12 will cause the program to exit (thereby rejecting loose electrode as a possible category for the sample record. It does this by causing the calling program to be reverted to through a return point 13. On the other hand, if a following pulse is detected by the subroutine 11, a negative result of test 12 will reach steps 14 in which: the beginning sample is set equal to the sample of the peak so found; and the following pulse flag is set. Then the width peak subroutine 7 is called again, this time to determine the width of the following peak. If the width of the following peak is inadequate, a negative result of test 8 will reach test 9 which this time is affirmative, causing the calling program to be reverted to through the return point 13, thus rejecting loose electrode as a possible category for the present sample record. If desired, steps 14 could increment a counter and test 9 could compare the counter to reject a record after testing the width of 3, 4 or more narrow pulses. Such has not been found necessary, as yet.

If (in either the first or second pass through the subroutine 7) a width in excess of the width low limit is indicated, an affirmative result of test 8 reaches a test 16 in which the number of zero crossings (found by the subroutine 3) is compared against a zero crossing high limit. If there is too high a frequency content, an affirmative result of test 16 causes the calling program to be reverted to through the return point 13, thus rejecting loose electrode as a possible category for the current sample record. The number of zero crossings is used as a discriminant against other waveshapes which may have a wide first or second pulse, such as the surge waveshape of FIG. 59. If there were not found to be an excessive number of zero crossings, a negative result of test 16 will reach a series of steps 17 which set up the conditions for degrading the pulse record as a function of zero crossings in the degrade subroutine 18. Then the quality factor, Q, for the loose electrode category is established in a step 19 as unity minus the ratio of the degradation factor to the maximum degradation permitted for this category. Then a test 20 determines if the quality factor is negative; if it is, the quality factor for the current category is set equal to zero in a step 21; otherwise, the quality factor for this category is set in a step 22 to equal the value of Q established in step 19. And then the calling program is reverted to through the return point 13.

LOOSE PROBE/RUB STRIP SUBROUTINE—FIG. 45

Figure 46:
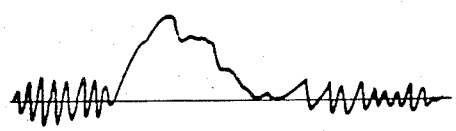
Figure 47:
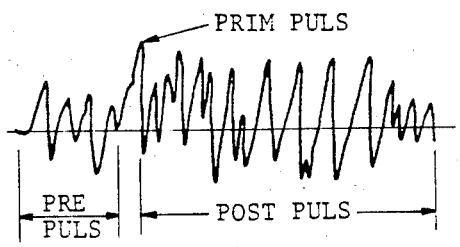

The loose probe/rub strip subroutine of FIG. 45 is utilized to sense a loose probe (such as probes 1 or 2 in FIG. 1) and to sense the ingestion of an abradable seal (rub strip) which has peeled loose from the compressor stage of the engine. The loose probe/signature (FIG. 61) is primarily random noise having a relatively low frequency structure. The rub strip results in a succession of very narrow pulses that merge into a high frequency signature (FIG. 62) with an R.M.S. level of nearly one volt. Thus, two parameters are utilized for these categories: one is R.M.S. noise and the other is the number of zero crossings (frequency content). In order to reduce the chance of falsely recognizing a wide or narrow pulse with a high noise content as being one of these two categories, the width of the primary pulse is excluded from the R.M.S. noise calculations. Referring to FIG. 46, a pulsatile signal with significant, high frequency noise could satisfy both the zero crossing and R.M.S. criteria of a loose probe or rub strip signature. Due to the energy of the pulse, the R.M.S. value over the 104 samples of the record could be around one volt. But, by excluding the pulse area from the R.M.S. calculation, the R.M.S. value will be very low and easily discriminated against. On the other hand, reference to FIG. 47 shows that exclusion of the primary pulse of either a loose probe or rub strip signature will have little effect on R.M.S. noise taken across the rest of the record.

R.M.S. Noise

The loose probe/rub strip subroutine is reached in FIG. 45a through an entry point 1, and a first series of steps 2 set the threshold for the width/peak subroutine 3 equal to one-tenth of a volt; the beginning sample is set equal to the sample of the probe threshold crossing; the width A.G.C. is reset; and the values of pre-pulse R.M.S. noise and post-pulse R.M.S. noise are both preset to zero. After calling the width/peak subroutine 3, in a series of steps 4, a pre-pulse interval is identified as being from the beginning of the record to the beginning sample of the pulse found by the width/peak subroutine 3, referred to as S1, which also identifies the end sample of the pre-pulse R.M.S. interval. The post-pulse R.M.S. interval is established in the second one of the steps 4 as S2, which is the entire sample record following the end sample of the pulse found by the width/peak subroutine 3; and the pulse end is memorized as the end sample found in the subroutine 3. Then a test 5 determines if S1 is greater than 1, meaning that there is in fact a pre-pulse R.M.S. interval. If it is, an affirmative result of test 5 reaches steps 6 in which the beginning sample is set equal to 1, and the end sample is set equal to S1 to establish the conditions for running the R.M.S. subroutine 7. The R.M.S. value found by the subroutine 7 is preserved as the pre-pulse R.M.S. in a step 8. If S1 is not greater than 1, a negative result of test 5 bypasses the pre-R.M.S. calculations 6–8.

To find the post-pulse R.M.S. value, a series of steps 9 set the beginning sample equal to the pulse end memorized in steps 4 and set the end sample equal to the maximum sample of the record. Then the R.M.S. routine 10 is called to provide the post-R.M.S. value, which is memorized in the first of a pair of steps 11. In the second of the steps 11, the pre-R.M.S. value and post-R.M.S. value are added, quadratically (since they cannot be added linearly). Thus the total R.M.S. value is found as the square root of the proportionate contribution of the pre-R.M.S. and post-R.M.S. intervals as set forth in steps 11, all in a well known fashion. Then a test 12 determines if the total R.M.S. noise is less than an R.M.S. low limit as set forth in Table 6. If it is, an affirmative result of test 12 will cause the calling program to be reverted to through a return point 13, thus rejecting either loose probe or rub strip (as the case may be) as a potential category for the record being tested. If the R.M.S. is above the low limit, a series of steps 14 establish the conditions for degradation on R.M.S. noise by the degrade subroutine 15.

Zero Crossings

The loose probe/rub strip subroutine continues in FIG. 45b with a series of steps 17 which set up the conditions for calling the zero crossings subroutine 18: the beginning and ending samples are set equal to the first and last samples of the record, and the threshold is set equal to the zero crossing threshold of Table 6. The number of zero crossings found by the zero crossing subroutine 18 is compared in a test 19 to see if it is lower than a zero crossing low limit set forth in Table 6. If it is, an affirmative result of test 19 will cause the calling program to be reverted to through a return point 20, thereby rejecting the appropriate category as a candidate for the record under test. But if there is a sufficient number of zero crossings, then a test 21 determines if there are too many zero crossings (too high a frequency content). If the number of zero crossings exceeds the zero crossing high limit (Table 6) an affirmative result of test 21 will cause the calling program to be reverted to through the return point 20. If the number of zero crossings is suitably within the desired range, negative results of both tests 19 and 21 will reach a series of steps 22 in which the conditions are established for degrading the category on zero crossings in the degrade subroutine 23. Then, the quality factor, Q, for the category under test is established as unity minus the ratio of the total degradation (effected by running the degrade subroutine 15, 23 for both R.M.S. noise and zero crossings) to the maximum degradation permitted for the given parameter. Then a test 25 determines if the degradation has exceeded the maximum, and if so, a step 26 sets the quality factor for the current category equal to zero. Otherwise, a step 27 sets the quality factor for the current parameter equal to the value of Q established in the step 24. And then the calling program is reverted to through a return point 28.

ABNORMAL AFTERBURNER CHOP SUBROUTINE—FIG. 54

The abnormal afterburner chop subroutine of FIG. 54 is utilized to identify probe 3, category 11 and category 12. Both the beginning and the ending of an abnormal afterburner chop, believed (although not known with certainty) to be related to rubbing of a nozzle member during nozzle closure, are characterized by intervals of high noise and intervals of low noise. During the start of the abnormal afterburner chop, the low noise interval is followed by a high noise interval that begins abruptly with a negative excursion. At the end of the abonormal afterburner chop, a high noise interval ending abruptly in a positive excursion is followed by a low noise interval. The abnormal afterburner chop subroutine of FIG. 54 utilizes the R.M.S. noise in the high noise interval, and the zero crossings in the high noise interval separately from the zero crossings in the low noise interval in order to identify these categories.

Figure 48:
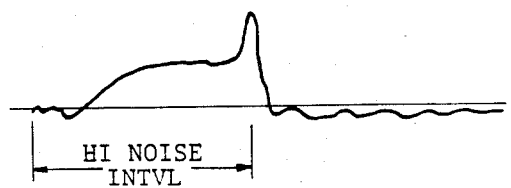
Figure 49:
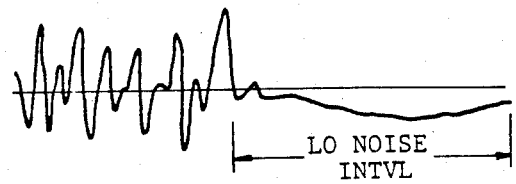
Figure 50:
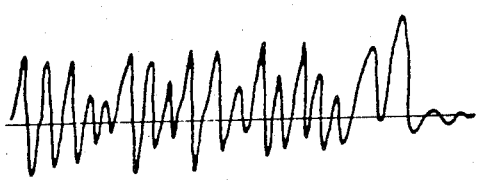

Referring to FIG. 48, a normal afterburner chop (as in FIG. 79), but with a suitably wide, high amplitude pedestal could provide a high R.M.S. noise value in the high noise interval, and could otherwise meet the criteria of the end of abnormal chop (FIG. 78). However, by requiring a minimum frequency content in the high noise region, the signature of FIG. 48 can be discriminated and rejected from consideration as start of abnormal chop. To discriminate against rub strip (FIG. 62) or acel/decel (FIG. 80), the absence of activity in the low noise region is of interest. Referring to FIG. 49, D.C. drift could provide a high R.M.S. value in the low noise interval of a valid abnormal afterburner chop signature. Therefore, low R.M.S. noise cannot be used to discriminate against other gross signals. Instead, a low zero crossing count (based on a suitable threshold) eliminates gross signals (FIG. 62 and FIG. 80). Referring to FIG. 50, the signature in question could have its final, positive pulse too close to the end of the record to indicate whether it is a rub strip (FIG. 51) or an abnormal A/B chop (FIG. 52). Therefore, a minimum post-pulse, low noise interval is required, or the pulse is rejected.

The abnormal afterburner chop subroutine is reached in FIG. 54a through an entry point 1 and in a first test 2, examines the sign set in step 23 or 24 of the third probe subroutine of FIG. 12 to determine whether the beginning of chop or end of chop is being looked for. If the sign is negative, this means the beginning of chop is being looked for and searching for the high noise region should begin at the lowest sample number and proceed to the right. Therefore, a negative result of test 2 reaches a step 3 to reset the reverse flag that is utilized in the following peak subroutine. If the sign is positive, an affirmative result of test 2 reaches a step 4 to set the reverse flag. Then a series of steps 5 establish the conditions for running the following peak subroutine 7: the beginning sample is set equal to 1; the end sample is set equal to the maximum sample; and the threshold is set equal to the peak threshold set forth in Table 7. In the case of the end of abnormal chop, because the reverse flag is set, the search for the following peak begins at the MAX sample and ends at the first sample of the record, as described with respect to FIG. 15, hereinbefore.

In FIG. 54a, after running the following peak subroutine 7, if no peak in fact has been found, an affirmative result of a test 8 will cause the calling program to be reverted to through a return point 9, thus rejecting abnormal afterburner chop as a category for the current sample record. But if a peak has been found, a negative result of test 8 reaches a test 9a to determine if the high noise threshold (Table 7) is greater than unity, or not. If it is, the program definition of a threshold exceeding unity causes a step 10 to use only the decimal fraction portion thereof as a multiplicand against the magnitude of the peak found by the subroutine 7, so as to provide an A.G.C. high noise threshold related to the peak value of either the beginning or ending of the high noise region. Otherwise, step 10 could be bypassed, if desired. Similarly, steps and tests 12–17 will convert the low noise threshold, the R.M.S. low limit, and the R.M.S. nominal value to A.G.C. values if they are provided to the abnormal A/B chop subroutine as values greater than unity; otherwise, the conversion steps are bypassed. In the present example, the R.M.S. low limit and R.M.S. nominal values are less than unity and therefore they are not converted to A.G.C. values as a function of the peak value of the end excursion of the high noise interval.

The abnormal A/B chop subroutine continues in FIG. 54b with a test 19 which determines if beginning or ending of chop is involved. If the sign is negative, a negative result of test 19 reaches a series of steps 20 which set: the beginning of the high noise interval equal to the sample of the peak found by the following peak subroutine 7; the end of the high noise interval equal to the maximum sample; the beginning of the low noise interval equal to the first sample; and the end of the low noise interval equal to one sample less than the sample of the peak found for the first excursion of the high noise interval.

On the other hand, if the sign is positive, an affirmative result of test 19 will reach a series of steps 21 in which: the beginning of the high noise interval is set equal to the first sample, the end of the high noise interval is set equal to the sample of the peak of the final excursion; the beginning of the low noise interval is set equal to one sample higher than the peak of the final excursion; and the end of the low noise interval is taken as the maximum sample. Then in a series of steps 22: the high noise interval is defined as the end of the high noise interval minus the beginning of the high noise interval; the low noise interval is set equal to the end of the low noise interval minus the beginning of the low noise interval; the beginning sample is set equal to the beginning of the high noise interval; the ending sample is set equal to the ending of the high noise interval; and the threshold is set equal to the high noise threshold. Then the zero crossing subroutine 23 is called. The number of high noise interval zero crossings is set in a step 24 to be equal to the number of zero crossings found by running the subroutine 23. Then, using the same beginning and ending sample, the R.M.S. subroutine 26 is called. Then, in steps 27, the beginning sample is set to the beginning of the low noise interval and the ending sample is set to the end of the low noise interval. The zero crossing subroutine 28 is called with respect to the low noise interval and the number of zero crossings found in the low noise interval is set, in step 29, to equal the number of zero crossings found in the second running of the zero crossing subroutine 28. Then a test 31 compares the low noise interval with a low noise interval limit, which is shown in Table 7 to be 22 samples. The reason for this is if the low noise interval is too short, the signature could be a non-chop gross signal (as in FIG. 51); the region must be long enough to verify a low noise region. If the low noise interval is too small, an affirmative result of test 31 will cause the calling program to be reverted to through a return point 32, thus rejecting abnormal afterburner chop as a candidate category for the record under test. If there is a suitable low noise interval, a negative result of test 31 will reach a test 34 to determine if the R.M.S. noise in the high noise interval is less than an R.M.S. low limit set forth in Table 7.

If it is, the calling program is reverted to through the return point 32, thus rejecting abnormal afterburner chop as a candidate category. If there is a suitable low noise interval and suitable high noise interval R.M.S. value, a series of steps 35 set up the conditions for degrading the record on R.M.S. noise by calling the degrade program 36.

The abnormal afterburner chop subroutine continues in FIG. 54c with a series of steps 37 that normalize the nominal and limit values of high noise interval and low noise interval zero crossings counts to the length of the interval in which they are counted. This is done by providing values on a full-record basis (Table 7), and taking the ratio thereof for the appropriate interval. Then, a test 38 compares the zero crossings in the high noise region against the high noise limit provided in steps 37. If there are insufficient zero crossings, an affirmative result of test 38 causes the calling program to be reverted to through a return point 39, thus rejecting abnormal afterburner chop as a candidate category for the record under test. Otherwise, a negative result of test 38 reaches a series of steps 40 which establish the conditions for degrading the record as a function of high noise interval zero crossings by calling the degrade subroutine 41, using the nominal value calculated in steps 37. Then a test 42 determines if the low noise zero crossings are greater in number than a low noise limit calculated in steps 37. If so, the calling routine is reverted to through the return point 39. The purpose of comparing on the high and low limits in an opposite fashion is because any abnormal afterburner chop must have an active high noise region and a fairly quiet low noise region. If the number of zero crossings in the low noise region is not excessive, then a series of steps 44 establish the conditions for degrading the sample record on the number of zero crossings in the low noise region by calling the degrade subroutine 45, using the nominal value calculated in steps 37. And then, the quality factor, Q, for either of the abnormal afterburner chop categories, as the case may be, is determined in step 46, as unity minus the ratio of total degradation to maximum degradation permitted. Then a test 47 determines if excessive degradation has resulted in a negative Q; if it has, a step 48 sets Q for the category equal to zero; otherwise, a step 49 sets Q for the category equal to the value of Q found in step 46. Then the calling program is reverted to through a return point 50.

NORMAL AFTERBURNER CHOP SUBROUTINE—FIG. 55

The normal afterburner chop subroutine of FIG. 55 looks for a peculiar spike that occurs contemporaneously with minimum nozzle area as the nozzle is closed in shutting down the afterburner. As illustrated in FIG. 79, this pulse has a rather narrow peak sitting atop a rather wide pedestal. And the pulse is also characterized by a low R.M.S. noise level following the pedestal. The normal afterburner chop subroutine is reached in FIG. 55a through an entry point 1 and a first test 2 determines if the record under test has a positive record threshold crossing. If not, an affirmative result of test 2 will cause the calling program to be reverted to through a return point 3, thus eliminating normal afterburner chop as a candidate category for the record under test. Then a series of steps 4 set up the conditions for testing the width of the pedestal in the width/peak subroutine 5: the beginning sample is set to the sample of the probe threshold crossing; the width threshold is set equal to the low width threshold (of Table 8); and the width A.G.C. is reset, so that the width/peak subroutine 5 is passed through only one time with a fixed width threshold. After the width/peak subroutine 5 concludes, in a series of steps 6: the pulse end sample is identified as one sample greater than the end of the primary pulse found by the subroutine 5; the low width of the pulse (the width of the pedestal) is set equal to the width of the primary pulse found by the subroutine 5; the width threshold is calculated as the upper width threshold times the absolute value of the magnitude of the peak found in the subroutine 5; the R.M.S. divisor (for degrading the record on noise level) is calculated as the R.M.S. divisor times the absolute value of the magnitude of the found in the subroutine 5; and the beginning sample for running the width/peak subroutine 7 is set equal to the sample of the peak found in the subroutine 5. The width/peak subroutine 7 is thus run to determine the width of the narrow, upper portion of the pulse. The narrow upper width constraint discriminates against single positive pulses followed by low noise, such as that shown in FIG. 71. In steps 8: the upper width is set equal to the width found in the subroutine 7; the beginning sample is set equal to the pulse end of the pedestal, as found in running the subroutine 5; the end sample is set equal to the maximum sample; the threshold is set equal to the peak threshold; the reverse command is reset; and the sense command is set equal to zero. Then the following peak subroutine 9 is called, looking for any positive or negative peak beginning at the end of the pedestal and searching to the right to the end of the sample. If any peak is found, the record is probably a strange example of acel/decel (FIG. 80), so an affirmative result of a test 10 will cause the calling program to be reverted to through a return point 11, thus eliminating normal afterburner chop as a candidate category for the record under test.

Figure 51:
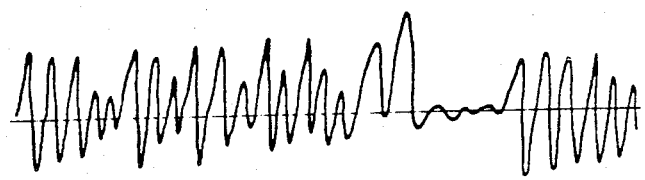
Figure 52:
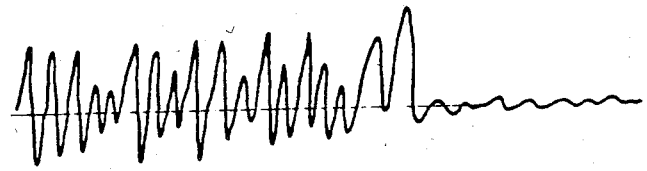
Figure 53:
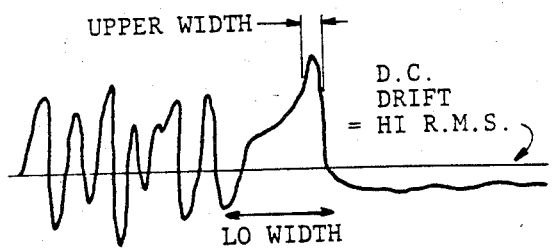

In FIG. 55a, a test 13 determines if the number of samples between the right-hand end of the pedestal and the end of the sample record is sufficient to confirm low R.M.S. noise, as described with respect to FIG. 50—FIG. 52, hereinbefore, by comparing it with a post-pulse R.M.S. interval low limit (Table 8). If there is an insufficient R.M.S. interval, an affirmative result of test 13 will bypass the measuring of R.M.S. noise and degradation thereon. But if there is a sufficient interval, a negative result of test 13 reaches the R.M.S. subroutine 14, utilizing the beginning and ending samples established in the steps 8. A high post-pulse R.M.S. noise could be indicative of an abnormal chop, as in FIG. 53, because abnormal chops frequently have high post-pulse D.C. drift, whereas normal chops do not. If the value of R.M.S. noise determined by the subroutine 14 exceeds an R.M.S. high limit, an affirmative result of a test 15 will cause the calling program to be reverted to through a return point 16, thus eliminating normal afterburner chop as a potential category for the record under test. But if the R.M.S. noise is within limit, a negative result of test 15 reaches a series of steps 17 which set up the conditions for degrading the pulse record on R.M.S. noise by calling the degrade subroutine 18.

The normal afterburner chop subroutine continues in FIG. 55b with a test 20 which determines if the necessarily narrow pulse atop the pedestal is wider than an upper width limit. And a test 21 determines if the necessarily wide pedestal is narrower than a low width limit. If either of these conditions exist, the record cannot result from a normal afterburner chop. Therefore, an affirmative result of either test 20 or test 21 will cause the calling program to be reverted to through a return point 22, eliminating normal afterburner chop as a category candidate for the record under test. Then, a series of steps 24 set up the conditions for degrading the sample record on the width of the pedestal by calling the degrade subroutine 25. And a series of steps 26 set up the conditions for degrading the record on the width of the pulse atop the pedestal by calling the degrade subroutine 27. In step 28, the quality factor, Q, is calculated as unity minus the ratio of the sum of the three degradations to the maximum degradation permitted for this category. A test 29 determines if the degradation has exceeded maximum. If it has, an affirmative result of test 29 reaches a step 30 where the Q for the category is set equal to zero. Otherwise, a negative result of test 29 reaches a step 31 where Q for the category is set equal to the value of Q determined in step 28. And then the calling program is reverted to through a return point 32.

ACEL/DECEL SUBROUTINE—FIG. 56

The acel/decel subroutine of FIG. 56 is utilized to recognize generally normal acceleration/deceleration noise, as illustrated in FIG. 80. Depending upon the voltage threshold utilized for the third probe, the acel/decel subroutine can be used to recognize only excessive acceleration/deceleration noise. This may be achieved by utilizing a voltage threshold on the third probe which is based at least in part upon the noise charactertistics of the engine, as described hereinbefore with respect to FIG. 7. If the threshold varies with engine noise, acceleration or deceleration noise should not trip the threshold; if it does trip the threshold, and acceleration/deceleration noise is the indicated category, this provides an indication of some abnormality in the engine, such as may occur if there is a cracked engine case or the like. On the other hand, if a fixed threshold is utilized for the third probe, and under rapid acceleration or deceleration the noise can exceed the threshold, then categorizing the result as normal acceleration/deceleration is an indication of the lack of engine distress (rather than a category identifying distress). The electrostatic signature of normal acceleration or deceleration is correlated noise on the order of 1 volt R.M.S. level, and on the order of 100 Hz. It has no narrow spikes, but it may contain several positive or negative excursions of 10ms-20ms duration. To decrease the possibility of falsely categorizing some other, large narrow spike with a high noise content (such as a rub strip, FIG. 62, or abnormal chop, FIG. 77 or FIG. 78) as acel/decel noise, the record is checked at the point of threshold crossing for a narrow spike; if one exists, the record is degraded.

The acel/decel subroutine is reached in FIG. 56 through an entry point 1, and a series of steps 2 set up the conditions to look for a very narrow spike by calling the width/peak subroutine 3: the beginning sample is set as the sample of record threshold crossing; the width A.G.C. is set; and the threshold is set equal to the width threshold of Table 9. As described with respect to FIG. 14, the width/peak subroutine 3 is run first to find the peak value of the primary pulse, after which the A.G.C. width threshold is calculated internally as a function thereof, and then the width at the A.G.C. level is found in a second pass therethrough. This relative width is a better measure of the undesirable narrow spike than a fixed threshold width would be. When the width/peak subroutine 3 concludes, the width at the A.G.C. threshold crossing is checked in a test 4 to determine if it is less than a width low limit of Table 9. If it is, an affirmative result of test 4 reaches a step 5 in which the record is degraded by a width degrade factor, which is seen in Table 9 to be 40% of the maximum degradation. Then a series of steps 7 establish the conditions for testing the record for R.M.S. noise by calling the R.M.S. subroutine 8: the beginning sample is set to one sample higher than the end of the pulse found in the subroutine 3, and the end sample is set equal to the maximum sample. After calculating R.M.S. in the subroutine 8, a series of steps 10 establish the conditions for determining the number of zero crossings by calling the zero crossing subroutine 11: the beginning sample is set equal to the first sample of the record (the end sample remains the maximum sample as set in steps 7); and a threshold is set equal to the zero crossing threshold of Table 9. After the zero crossings are determined, a series of steps 12 set up the conditions for degrading the sample record on the number of zero crossings by calling the degrade subroutine 13. Then a series of steps 14 set up the conditions for degrading the sample record on the R.M.S. noise level by calling the degrade subroutine 15. And the quality factor, Q, is calculated in a step 16 as unity minus the ratio of the three components of degradation to the maximum degradation permitted for this category. If the degradation is excessive, an affirmative result of a test 17 will reach a step 18 wherein the Q for the present category is set equal to zero. Otherwise, a negative result of test 17 reaches a step 19 wherein Q for ths category is set equal to the value of Q determined in step 16. And then, the calling program is reverted to through a return point 20.

A simpler embodiment of the present invention takes into account certain characteristics of waveshapes at one probe vs. characteristics of waveshapes at another probe that allow interprobe correlation in a much simpler fashion than that which has been described hereinbefore. In general, the characteristics differ depending upon whether a pocket of charge is caused by a metal/nonmetal rub (such as a compressor blade rubbing on an abradable seal), a metal-to-metal rub, or an erosion (high temperature corrosion). Although it is not fully understood nor proven beyond peradventure as yet, it is believed that metal/abradable rubs are similar to erosions. A negative pocket theory is believed to have been proven conclusively for erosions. Under this theory, a microscopic surface burn creates a pocket of very hot particles in the 5 to 100 micron range of size. The particles are hot enough to thermionically emit electrons, leaving the particles positive; the emitted electrons rapidly attach to air molecules making negative ions. This results in a mixture of positive particles and negative ions, with no excess charge, as yet. However, the particles are much heavier than the ions and have a difficult time following the gas stream of the engine. The particulate matter, therefore, hits vanes, blades and other engine walls and is neutralized. But the ions, of molecular size, are sufficiently light that they must follow the gas flow stream through the engine. This results in a pocket of net negative charge. A noninsulated probe (such as probes 1 and 2 herein) may actually be contacted by the particulate matter, prior to the particulate matter contacting blades, vanes or other walls of the engine. As a newly formed pocket passes such a probe, the lighter ions will not contact the probe; the heavier particles actually contacting the probe cause the probe to be positive (the negative ions in the vicinity of the probe being masked thereby). Thus, a probe which is located immediately downstream of an erosion will sense the erosion as a very sharp, initially positive pulse, as illustrated in FIG. 67. However, if an erosion occurs sufficiently upstream of the probe so that the particles can discharge to the blades, vanes and other engine walls prior to the pocket passing by the probe, the pocket will then simply be a group of negative ions and will cause an erosion to be sensed as a wider, negative pulse as in FIG. 63 and FIG. 64. The difference is that the probe 2 is located immediately downstream of the second high turbine blade and thus senses second high turbine erosions by impact from the particles themselves, but is more remote from the first high turbine, the particulates having been neutralized on the engine walls prior to reaching probe 2 when originating in the first high turbine. Further, the second high turbine blade or vane erosion of FIG. 67 is a sharp, positive pulse, but all of the erosion pulses become negative before reaching probe 3, as illustrated in FIG. 75 and FIG. 76.

The foregoing theory holds equally well for metal-on-metal rubs. The difference is that the rubs initially make a mixture of negative particles and positive ions. The reason for this is not yet understood. However, comparison of second high turbine rub illustrated in FIG. 66 with the high turbine rub illustrated in FIG. 72 show the same polarity reversal as a consequence of the particles being neutralized at the walls of the engine, whereas the ions being of molecular size, follow the gas flow stream and do not become neutralized. In the simpler embodiments of the invention, the foregoing considerations of the initial pulse polarity (the polarity of the waveform as it first crosses the threshold) are utilized together with the fact that the probes are displaced from each other along the flow of the gas stream. For instance, if a pocket of charge passes by all three probes, it may cause a threshold crossing at probe 2 within a time frame (based on the 1.3 kilohertz sampling rate) of between 2 and 8 samples after passing probe 1. Similarly, it may cause a threshold crossing at probe 3 on the order of 8 to 20 samples after causing a threshold crossing at probe 2, as shown in FIG. 81. High turbine vane erosion is illustrated in FIG. 82.

Referring now to FIG. 83, a data acquisition interrupt routine of a second, simple embodiment of the invention is reached through an entry point 1 and a test 2 determines if the routine has been initialized or not. On first power-up, test 2 will be negative reaching a series of steps 3 that reset 8 category counters (for 7 categories that can be identified in this embodiment together with an unknown category); reset a record classification flag; set the probe number equal to 3; set a noise counter equal to zero; and then set the initialize flag. Thereafter, each time there is a data acquisition interrupt, the initializing steps 3 are bypassed due to an affirmative result of step 2.

In the iterative part of the data acquisition interrupt of FIG. 83, the P pointer is advanced to the next higher numbered probe (initially, probe 1) and the A/D for that probe is started in steps 4. Then a test 5 determines when the conversion is complete in the A/D of the particular probe and a test 6 determines if a record is in progress, or not. Initially, there is no record in progress, so a negative result of test 6 will reach a test 7 to determine if a record has been initiated, or not. Initially it will not, so a negative result of test 7 reaches a test 8 to determine if the current probe is probe 1. Initially it is, and an affirmative result of test 8 reaches a step 9 to set the time frame, T, equal to 1. The time frames T=1, T=2, and T=3, respectively relate to the times at which a record having threshold crossings at all three probes will occur for the respective probes. Thus if there is a threshold crossing at probe 1, it is defined to occur at T=1; then, if this is a record of an event seen by all three probes (as in FIG. 81), probe 2 should have a threshold crossing from 2 to 8 samples later which is defined as T=2, and the third probe should have a threshold crossing 12 to 24 samples later (than probe 1), which is defined as T=3. On the other hand, if the events occur downstream of probe 1, and therefore are only seen in probes 2 and 3, a short record is declared so that the initial threshold crossing at probe 2 occurs in T=2, and within 8 to 20 samples later, a threshold crossing for probe 3 will occur in T=3 (as in FIG. 82). Following step 9, a test 11 determines if the digital value at the given probe is greater than a positive threshold for that probe; if so, an affirmative result of test 11 reaches a step 12 to set a plus flag for that probe and time frame. If not, a negative result of test 11 reaches a step 13 to determine if the current A/D has a value less than the negative threshold for the particular probe in question. If so, a step 14 sets a minus flag for the particular probe and time frame. If not, a negative result of test 13 reaches a test 15 to determine if all three probes have been sampled or not. If not, the routine of FIG. 83 reverts to steps 4 to advance the probe pointer to the next probe and start its A/D. Assuming no threshold crossing has occurred for the first probe, no record will be in progress or initiated so that tests 6 and 7 will again be negative, but this time test 8 will be negative. This reaches a test 16 to see if the current probe is probe 2. If so, a step 17 sets a short record flag, indicating that if there is a record it will only have threshold crossings at probes 2 and 3 (since probe 1 did not have a threshold crossing). And the time frame is set to 2 in a step 18 to identify the normal time frame for signals to appear at probe 2 (along the gas stream flow). Then the tests 11 and/or 13 are repeated. Assuming both of them are negative, test 15 will be reached and since probe 3 has not yet been tested, its result will be negative as well. This causes steps 4 to be reached to advance the P pointer and start the A/D converter for the third probe. When it is complete, tests 6 and 7 will again be negative since neither the first nor second probe had declared a record. This causes test 8 to be reached and since the current probe setting is 3, there will be a negative result of test 8 as well as a negative result of test 16 so that a step 19 sets S=24 (for reasons described hereinafter and a step 20 sets the time frame to 3. Then, threshold crossings are examined in tests 11 and 13 for the third probe. This time test 15 is affirmative reaching a test 21 to determine if a record has been initiated or not. In the example being considered, no record has been initiated so a negative result of test 21 will cause the data acquisition interrupt routine of FIG. 83 to end at a point 22.

In the next data acquisition interrupt (about 80 milliseconds later, at the 1.3 kilohertz sampling rate), assume that there is a threshold crossing for probe 1. This causes one of the flags to be set for probe 1, time 1 in one of the steps 12, 14. And then a test 23 is reached to determine if a record is in progress. Initially, the record is not in progress but this reaches a step 24 to set a record initiated flag. Then test 15 is reached and a negative result of that causes the steps 4 to be reached to advance the P pointer to the second probe and to start its A/D converter. A record has not been fully declared so the record in progress test 6 is still negative; but a record has been initiated in the present example, so test 7 is affirmative, bypassing the initiation steps and tests 8-9, 16-20, setting the sample number, S, equal to 1 in a step 24 and allowing probe 2 to be sampled in the tests 11 and 13 while the time frame is still set at 1. Since a record has been initiated, the presence or absence of the signal in the first time frame from the second probe is indicative not of classification, but of fault (since the same engine event cannot occur at probes 1 and 2 in the same time frame). This is described more fully with respect to FIG. 84, hereinafter. If there is a threshold crossing, one of the tests 11, 13 will cause a corresponding step 12, 14 to set the appropriate flag. This would reach test 23 which is still negative, and cause reenforcing of the setting of the record initiated flag in step 24 (but since it was already set, this is irrelevant). Then test 15 is negative causing steps 4 to advance P to the third probe and start its A/D. When complete, an affirmative result of test 5 causes test 6 to be reached once more. The record has not yet been fully declared so a negative result of test 6 reaches test 7. Test 7 is affirmative because probe 1 initiated the record; this allows the third probe to be sampled for a threshold crossing with respect to the first time frame. If there is a threshold crossing in the third probe, it will cause one of the steps 12, 14 to set an appropriate flag and again reach the test 22 which is still negative, reaching step 23. If there were no threshold crossings, the negative result of test 13 would cause test 15 to be reached. This time test 15 is affirmative reaching test 21 which is also affirmative. An affirmative result of test 21 reaches a pair of steps 25 which set the record in progress flag and reset the record initiated flag, and then the data acquisition interrupt routine ends at the point 22.

As a consequence of the next following data aquisition interrupt, the program of FIG. 83 proceeds differently. When the first probe A/D is complete as indicated by an affirmative result of test 5, test 6 is reached; test 6 is now affirmative reaching a test 26 to see if probe 1 is current; if so, this reaches step 27 which increments S, the sample number. Then a test 28 is reached to determine if a short record has been declared or not. In the example given, probe 1 had a threshold exceedance which declared the record, so the step 17 was never reached due to the fact that test 7 caused it to be bypassed. Therefore, test 28 will be negative reaching a test 29 to determine if the current sample number is between 2 and 8. In the example given, the sample number has been incremented (in step 27) from 1 (set in step 24) to 2. Thus, test 28 will be affirmative reaching step 18 to set the time frame equal to 2. This defines the permissible range of times (between samples 2 and 8) when valid data of a three pulse record can be received at the second probe. On the other hand, if data is received on the first probe, flags could be set for probe 1, second time frame if in fact there continues to be a threshold exceedance on probe 1. However, this poses no problem since the information is simply ignored, thereby enabling a simpler embodiment (rather than complicating the issue and not recognizing a threshold crossing for probe 1 during the second time frame). If the second probe did not have a threshold crossing, negative results of tests 11 and 13 reach test 15 which is negative, thereby reverting to steps 4. On the other hand, if there were any threshold crossing (even though it will be ignored as described hereinafter), an affirmative result of either test 11 or 13 will pass through one of the steps 12, 14 to the test 23. Since a record is currently in progress, an affirmative result of test 23 will reach the test 15 to determine if all three probes have been sampled or not. A negative result of test 15 reverts to the steps 4. For the second probe, when steps 4 advance the P pointer to the second probe, and its A/D conversion is complete, step 6 is affirmative reaching test 26, which now is negative since the second probe is being pointed to by the P pointer. Thus step 27 is bypassed and S is not incremented. Test 28 is negative but test 29 is affirmative, so the second probe threshold crossing is tested for the second time frame. If the second probe has a threshold crossing during the second sample of the record, one of the tests 11, 13 will cause a corresponding step 12, 14 to set an appropriate flag. And then an affirmative result of test 22 will reach test 15; if there is no threshold crossing, steps 11 and 13 being negative will reach step 15, the negative result of which will cause steps 4 to be reverted to. For the third probe, the operation is the same as for the second probe. That is, test 6 is affirmative, test 26 is negative, test 28 is negative, test 29 is affirmative, so that the third probe has its value tested for a threshold crossing for the second time frame in sample period 2. When all three probes have been tested during sample period 2 of a declared record, test 15 is affirmative and test 21 is negative causing the data acquisition interrupt routine of FIG. 83 to end at the point 21.

During the next six data acquisition interrupts in a row, test 6 is affirmative; test 26 will be affirmative for the first probe only, reaching step 27 which increments S; and in the example under consideration, test 28 is negative and test 29 will be affirmative. Thus all three probes are checked for threshold crossings during sample numbers 3-8. If any of these probes have threshold crossings in more than one threshold period, it simply reenforces the setting of the plus or minus flag. Of course, it is possible that during samples 2 through 8 a given probe may first cross the negative threshold and then cross the positive threshold (or vice versa); however, this is irrelevant in the case of system fault (as described with respect to FIG. 84, hereinafter). And, in the case of the pulses of interest, since probe 1 is compared only with probe 2 and probe 2 is compared only with probe 3, it can be seen that, in the expanse of sample numbers of interest for the higher numbered probe, there is little likelihood of a threshold crossing phase reversal. Specifically, if the first probe declares a record, it is a full record and the very next sample will change the time frame from $T=1$ to $T=2$. In the pulses of interest, such as that illustrated in FIG. 81, a phase reversal within samples 2 through 8 on probe 2 is unlikely. Similarly, if probe 2 initiates a record, no further sampling occurs until sample 8 when the time frame is advanced from $T=2$ to $T=3$ and there is little likelihood of a phase reversal on the third probe within the 8 to 20 samples where it is sensed.

The data acquisition interrupt of FIG. 83 proceeds after the eighth sample with a negative result of test 29 reaching a test 30 to determine if the sample number is between 12 and 24. During sample numbers 9, 10 and 11, a negative result of test 30 will reach a test 32 to determine if all three probes have been considered (although no threshold checks are made when both steps 29 and 30 are negative. And then, for sample numbers 12 through 24, test 30 is affirmative, reaching the step 10 which sets the time frame, $T=3$. Each of the three probes have their thresholds compared and when test 15 is affirmative, this reaches test 20 which is negative causing the interrupt routine to end at point 22.

Assuming that a record was not initiated by the first probe, then a negative result of test 8 and an affirmative result of test 16 reach the step 12 to set the short record flag. In such cases, once the record is in progress, on each pass through the data acquisition interrupt routine of FIG. 83, test 28 is affirmative, so the threshold checks are only made between sample numbers 8 and 20 as a consequence of a test 34.

In the case where neither the first nor second probe initiated a record, negative results of tests 8 and 16 reach a step 19 which sets the sample number, S, equal to 24. In all subsequent passes through the data acquisition interrupt routine of FIG. 83, when P is set equal to 1, test 26 will reach step 27 to increment S. Thus S is automatically higher than 24, so that test 30 will be negative in every pass of a record which is initiated by the third probe. During each pass through the data acquisition interrupt routine of FIG. 83 in which no threshold comparisons are made due to negative results of tests 29, 30 or 34, test 32 is reached to determine when all three probes have had their A/Ds started, even though no thresholds were checked for these probes. Whenever test 32 is affirmative, it reaches a test 37 to determine if the sample number is greater than 50. In the earlier parts of each record, test 37 will be negative causing the subroutine to end at point 22. Toward the end of any record, however, the sample number will eventually be incremented to 50 causing an affirmative result of test 37. This will reach a step 38 which starts the R.M.S. A/D and a test 39 that determines when the analog-to-digital conversion is complete in the R.M.S. A/D. When the conversion is complete, a test 40 determines if the R.M.S. A/D has a value higher than some noise limit (which may or may not be on the same order of magnitude as the probe thresholds). If a pulse-like record on one or more probes is in fact in progress, this means that other types of phenomenon (such as a rub strip or excessive acel/decel noise) are not involved. Stated alternatively, testing the high end of a record for the absence of noise is a good indication of a pulse-like record on one or more of the probes. If the R.M.S. noise is lower than the limit, an affirmative result of test 40 will reach a test 41 to determine if the sample number has reached 70 or not. If not, the data acquisition interrupt routine of FIG. 83 exits at point 22. If the noise is excessive, a negative result of test 40 will reach a step 42 which increments the noise counter. Then a test 43 determines if the noise counter has incremented to some value, such as 2 or 3, and if it has, this is taken as an indication that pulse-like waveforms are not being sensed, but rather gross waveforms are being sensed. Thus no classification can be made in the present embodiment. An affirmative result of test 43 will reach a series of steps 44 which reset the plus and minus flags; reset the record in progress flag; and restore the noise counter to a zero setting. But if the noise counter has not been incremented to 3, a negative result of test 43 causes the program to exit through the end point 22. If the noise is checked from sample number 50 through sample number 70 with no more than two exceedances, eventually test 41 will be affirmative causing a step 46 to set the record classification flag. This is an indication that the flag settings of steps 12 and 14 for all three probes now comprise a record which can be classified.

In the present embodiment, not only is simple interprobe correlation carried out, but also simultaneous signals on a pair of probes are taken as an indication of fault. This can only be carried out in a single direction: that is, if the second probe has a threshold crossing simultaneously with the initial threshold crossing of the first probe, this is an indication that something is wrong in the system, since pockets of charge normally will not reach threshold crossing magnitude at both probes simultaneously. On the other hand, the fact that the first probe may still have a threshold exceedance at the time that the second probe crosses the threshold is not indicative of fault because of the width of a pulse at the first probe causing its threshold to possibly be exceeded for several samples.

Referring now to FIG. 84, a rudimentary system fault subroutine is reached through an entry point 1 and a first test 2 determines if the record classification flag has been set or not. If not, the system fault routine simply ends at a point 11. If a record has been completed and the record classification flag has been set at step 46 of FIG. 83, an affirmative result of test 2 in FIG. 84 will reach a pair of steps 3 which set P equal to 1 and T equal to 1. Then a test 4 determines if there has been a plus flag set for probe 1 in time frame 1. If not, a test 5 determines if a minus flag has been set for probe 1 during time frame 1. If either test 4 or 5 is affirmative, this reaches a step 6 which sets the probe equal to 2. Then tests 7 or 8 determine if a plus or minus flag has been set for probe 2 in time frame 1. If so, an affirmative result of either test 7 or 8 will reach steps 10 in which the record classification flag is reset and system fault is indicated. This is possible because the second probe should never have a threshold exceedance concurrently with the first threshold exceedance of the first probe (defined as time 1 herein). And the routine then ends at point 11.

In FIG. 84, if both tests 4 and 5 are negative, a step 12 sets the probe equal to 2 and then reaches a step 14 to set the time frame equal to 2. Step 14 can also be reached if both tests 7 and 8 are negative (indicating no concurrence between the first and second probe). Then tests 15 and 16 determine if there was a plus or minus flag set for probe 2 during time 2. If so, an affirmative result of tests 15 or 16 will reach a step 17 to set the probe equal to 3 thereby causing tests 18 and 19 to determine if the third probe had a threshold exceedance during the second time frame. If it did, an affirmative result of either test 18 or 19 will reach the steps 10 to reset the record classification flag and to indicate system fault. On the other hand, if affirmative results of tests 7, 8, 18 or 19 are not reached, the record classification remains set.

Referring now to FIG. 85, the record classification routine is reached through an entry point 1 and a first test 2 determines if M, the number of records collected in the wear interval (FIG. 5-FIG. 7 hereinbefore) is zero or not, as described more fully hereinafter. Then, a test 3 determines if the record classification flag is set or not. It may never have been set (that is no record having been declared) or it may have been reset by the system fault routine of FIG. 84. If test 3 is negative, the record classification routine ends at a point 36. But if the record is to be classified, an affirmative result of test 2 reaches a pair of steps 4 in which P and T are both set equal to 1. Then a test 5 determines if a plus flag has been set for P=1, T=1. If it has, this may be indicative of compressor metal on abradable rub as illustrated in FIG. 57. An affirmative result of test 5 reaches a pair of steps 6 in which P and T are both set equal to 2. Then a test 7 determines if a minus flag has been set for the second probe in time frame 2. If it has, this is indicative of compressor metal on abradable rub, as indicated in FIG. 81 for the second probe. An affirmative result of test 7 reaches a step 8 to increment a counter for a first category, C, (defined in FIG. 86 as compressor metal/abradable rub). But if test 7 is negative, this means the two probes do not correlate to that category, and a negative result of test 7 will reach a step 9 which increments the counter for the eighth category, defined as unknown.

In FIG. 85, if the plus flag has not been set for the first probe in the first time frame, a negative result of test 5 will reach a step 10 to determine if the negative flag had been set for the first probe in the first time frame. If it had, this might be indicative of compressor metal-on-metal rub, as illustrated in FIG. 58. An affirmative result of test 10 reaches a pair of steps 11 in which P and T are both set equal to 2. Then a test 12 determines if a positive flag has been set for the second probe in the second time frame. If it has, this may be indicative of a rub pocket (such as that illustrated in FIG. 72 and FIG. 73) being sensed on the second probe (not otherwise illustrated herein). Thus an affirmative result of test 12 will reach a step 13 to increment a counter for a second category in this embodiment, which is identified in FIG. 86 as compressor metal-to-metal rub. But if the plus flag has not been set for the second probe in the second time frame, a negative result of test 12 reaches the step 9 to increment the unknown counter.

In FIG. 85, a negative result of test 10 reaches a pair of steps 14 which set P and T both equal to 2. Then a test 15 determines if the plus flag has been set for the second probe during the second time frame. If it has, this may be indicative of either first high turbine rub illustrated in FIG. 6548, or second high turbine blade or vane erosion as illustrated in FIG. 67. To determine which, if either, of these may have occurred, an affirmative result of test 15 reaches a pair of steps 16 which set P and T both equal to 3. Then a test 17 determines if the positive flag has been set for the third probe during the third time frame. If so, this may be indicative of one of the turbine rub categories illustrated in FIG. 72, FIG. 73 or FIG. 74. In such case, an affirmative result of test 17 will reach a step 18 to increment a counter for a third category identified in FIG. 86 as first high turbine rub. If test 17 is negative, however, that will reach a test 19 which determines if the minus flag has been set for the third probe in the third time frame. If it has, this may be indicative of one of the turbine erosions illustrated in FIG. 75 and FIG. 76. In such case, an affirmative result of test 19 reaches a step 20 which increments a counter for a fourth category identified in FIG. 86 as second high turbine erosion.

In FIG. 85, a negative result of test 15 reaches a test 22 to determine if the minus flag has been set for the second probe in the second time frame. If it has, this may be indicative of either of the erosions illustrated in FIG. 63 and FIG. 64, or it may be indicative of second high turbine rub illustrated in FIG. 66. In such a case, an affirmative result of test 22 reaches a pair of steps 23 wherein the probe and time frame are both set equal to 3. Then a test 24 determines if the plus flag has been set for probe 3 during the third time frame. If it has, this may be indicative of one of the turbine rubs illustrated in FIG. 72, FIG. 73, or FIG. 74. In such case, an affirmative result of test 24 reaches a step 25 to increment a counter for a fifth category identified in FIG. 86 as second high turbine rub. But if not, a negative result of test 24 reaches a test 25 which determines if a minus flag has been set for the third probe in the third time frame. If it has, this may be indicative of one of the high turbine erosions illustrated in FIG. 75 or FIG. 76. In such case, an affirmative result of test 26 reaches a step 27 which increments a counter for a sixth category identified in FIG. 86 as first high turbine erosion. But if not, a negative result of test 26 reaches step 9 to increment the unknown counter.

In FIG. 85, a negative result of test 22 reaches a pair of steps 30 which set the probe and time frame equal to 3 and a test 31 determines if the plus flag has been set for probe 3, time 3 in the absence of any other probes having pulses. If so, this could only be a low turbine rub illustrated in FIG. 7356, because it occurred downstream of probe 2. In such a case, a step 32 increments a counter for a seventh category identified in FIG. 86 as low turbine rub. But if test 31 is negative, this reaches the step 9 to increment the unknown category counter. Thus regardless of what the circumstances are, if record classification is to be performed, one of the incrementing steps 8, 13...9 of FIG. 85 will be reached, after which a series of steps 33 will reset the plus and minus flags that are set in steps 12 and 14 of FIG. 83 and utilized in FIG. 85; reset the record in progress flag so that a new record may be obtained; and increment the M counter (as described more fully with respect to FIG. 7 and FIG. 8 hereinbefore). Then a test 34 determines if M has exceeded the distress threshold; if it has, an affirmative result of test 34 reaches a step 35 to set the distress analysis flag; otherwise, step 35 is bypassed. And then the routine is ended at the point 36.

As described hereinbefore, if M becomes reset at the end of a wear interval prior to reaching the distress threshold, counting of records will begin anew. When this occurs, all of the category counters 8, 13...9 of FIG. 85 must be reset. Therefore, whenever the record classification routine is entered, if the test 2 is affirmative, this reaches a step 40 which resets all of the counters for categories 1 through 8. Whenever the record classification routine is entered and no classification has been ordered, a negative result of test 3 will cause the program to end at point 36.

Referring now to FIG. 86, the distress analysis routine is reached through an entry point 1 and a first test 2 determines if distress analysis has been ordered by the subroutine of FIG. 85, or not. If not, the routine simply ends at a point 3. But if so, a local value, C MAX, indicative of the category with the highest count, is initialized at zero and a category counter, C, is set equal to zero in a series of steps 4. Then a step 5 increments C and a test 6 determines if the counter for category C is higher than C MAX, and an affirmative result of test 6 will reach steps 7 wherein C MAX is set equal to the setting of counter C and the category, CAT, is set equal to C. Otherwise, steps 7 are bypassed. Then a test 8 determines if all 8 category counters have been considered. If not, the steps and tests 5-7 are repeated. Eventually, all eight categories will have been considered, and the category (CAT) will be set equal to the category number having the highest count in the counter. An affirmative result of test 8 reaches a test 9 to see if the category is 1. If it is, an affirmative result of test 9 reaches a step 10 wherein an indicator, a flag or some other utilization device is set to indicate that the abnormal wear which did occur during a wear interval was determined to be compressor metal on abradable rub. If test 9 is negative, a test 11 determines if the category is 2. If so, a step 11 causes an indication of compressor metal-on-metal rub. If test 11 is negative, a test 13 determines if the category is 3. If so, a step 14 provides an indication that the abnormal wear is first high turbine rub. If test 13 is negative, a test 15 determines if the category is 4. If so, a step 16 provides an indication that the abnormal wear is second high turbine erosion. In a similar fashion, a plurality of tests 17-20 determine if the category is 5-8 and if so, set a corresponding indication 21-24. If something goes wrong, and test 20 is negative, then an indication of system error may be provided in a step 25. And then G is incremented and the distress analysis flag is reset in steps 26, and the program ends through the point 3.

An even simpler embodiment of the interprobe correlation of the present invention employs no digital processing at all. Instead, the probes are fed through amplifiers and filters to positive and negative Schmidt triggers; if either Schmidt trigger fires for the given probe, it locks out the other one for 60 milliseconds, thereby recognizing only a single polarity of pulse in a given time frame. In addition, for the presence or absence of a positive or negative pulse to be sensed, the R.M.S. noise following the pulse is checked. Only if it is sufficiently low (as in FIG. 83) will the Schmidt trigger activity be taken as being indicative of pulses, rather than gross signals of some kind.

Referring to FIG. 87, the general arrangement for all three probes is illustrated. The probe 10 is connected by a line 11 to a terminating impedance 12 and to an R.M.S. detector 13. The impedance is connected to an amplifier 14, the output of which is fed through a suitable bandpass filter 15. The filtered probe signal on a line 16 is fed to a positive Schmidt trigger 17 and a negative Schmidt trigger 18. The Schmidt triggers may be provided with suitable thresholds of the type described with respect to other embodiments hereinbefore. The output of the positive Schmidt trigger is fed to an AND circuit 20 that feeds a 60 millisecond single shot 21. As depicted herein, the single shot 21 is assumed to normally have, in its quiescent condition, a "NOT" signal on a line 22; when the single shot is fired by the AND circuit 20, the signal on the line 22 disappears and a signal appears on a line 23 for 60 milliseconds after the single shot is triggered. In a similar fashion, the negative Schmidt trigger 18 is fed to an AND circuit 25 which feeds a single shot 26 which normally has a "NOT" signal on a line 27 and, when activated, instead provides a signal on a line 28. The signal on the line 22 is fed to the AND circuit 25 to prevent recognizing negative signals after the positive Schmidt trigger has fired; similarly, the signal on the line 27 is fed to the AND circuit 20 to prevent the positive Schmidt trigger from firing after the negative Schmidt trigger has fired. Thus whenever there is either a positive or a negative threshold exceedance, one of the single shots will fire and remain up for 60 milliseconds. This time period is chosen since pulses having significance in the present embodiment normally will not last any longer than 60 milliseconds, so that is a long enough shutoff for the opposite Schmidt trigger.

In order to recognize only signals which are likely to be pulsatile in nature, and thereby have some meaning in the present embodiment, the R.M.S. detector 13 in FIG. 87 is fed to a comparator 30, the output of which on a line 31 is only present when the R.M.S. noise is less than some predetermined threshold. This signal is fed to an AND circuit 32 along with the "NOT" signal on a line 34 from a 50 millisecond single shot 35 that is operated by an OR circuit 36 whenever one of the Schmidt triggers 17, 18 fires. As soon as one of the Schmidt triggers fires, the NOT signal on the line 34 disappears thereby blocking the AND circuit 32. Only after 50 milliseconds will the signal reappear and enable the AND circuit 32. The outputs of the 60 millisecond single shots 21, 26 are fed to corresponding AND circuits 40-43. The condition of the single shots is tested by the AND circuits 40 in the event of low noise 50 milliseconds after firing one of the Schmidt triggers 17, 18. Thus if the positive single shot has fired but there is a gross noisy signal, none of the AND circuits 40, 43 will operate. On the other hand, if a pulsatile signal is involved, with relatively low noise following the pulse, then the AND circuit 32 will gate the AND circuit 40 and the AND circuit 43 providing indications of P+(meaning a positive signal on this probe) and NOT P−(indicating not a negative signal on this probe). The reason for providing the NOT signals is that the lack of either signal can be utilized in the signal classification which follows, as described with respect to FIG. 88 hereinafter. All of the apparatus 11-43 comprises a signal conditioner 45 that provides output signals on lines 46-49.

Referring to FIG. 88, three probes 10 are shown as numbered 1 through 3. Each of these probes feeds a signal conditioner 45 that provides plus, not plus, minus and not minus signals on corresponding lines 46-49. The signals from probe 1 are fed to related twenty millisecond single shots 50 so as to provide 1 plus, not 1 plus, 1 minus, and not 1 minus signals on corresponding ones of a plurality of lines 52; the signals from probe 2 are fed through eighteen millisecond single shots 54 so as to provide 2 plus, not 2 plus, 2 minus, and not 2 minus signals on corresponding ones of the lines 52; and the signals from the third probe are fed through two millisecond single shots 56 so as to provide 3 plus, not 3 plus, 3 minus, and not 3 minus signals on corresponding ones of the lines 52. The signals on the lines 52 are fed selectively to a plurality of AND circuits 61-67, each of which corresponds to one of the categories 1-7 in FIG. 85 and FIG. 86, hereinbefore, an AND circuit 68 corresponding to a negative result of test 15 in FIG. 85. These provide corresponding category signals on related lines 71-77, in an obvious fashion in view of the description of FIG. 85 hereinbefore. Although not shown herein, if desired, the lines 71-77 may be utilized to increment corresponding counters to provide an indication of the category most prevelant, across any particular interval of time. And, the utilization of the M counter, which could be reset by the integral of the output of an R.M.S. detector (such as the detector 13 in FIG. 87) may be utilized in a fashion which should be obvious in view of the teachings of the other embodiments hereinbefore, if desired.

There has thus been shown three embodiments of interprobe correlation according to the present invention; two of the embodiments are far less sophisticated, and do not necessarily provide accurate results. However, when utilized with statistical distress analysis of the type illustrated in FIG. 86 herein and described more fully in a commonly owned, copending U.S. patent application entitled "Statistically Correlated Electrostatic Engine Diagnostics", Ser. No. 453,961 filed contemporaneously herewith by Zwicke et al, it is clear that whenever abnormal engine wear occurs, 90% of the signals will be caused by the same type of event, and the other 10% of the signals will be caused by a wide variety of events. Thus, use of statistical analysis even with the relatively less sophisticated embodiments described herein can form a very useful, low cost, lightweight, portable diagnostic tool, either digital or analog.

The advantages of the invention, in addition to providing the capability for low cost units, include the additional reliability which comes by correlating the probes to one another, rather than relying on the difficulty of classifying each probe as carefully as need be if only one probe were to be relied upon. This allows much looser discrimination since loose discrimination may give rise to a pair of possible categories on any given probe, but not the same pair on two probes. The positive and negative aspect which is quite obvious with reference to the right-hand side of FIG. 88 also indicates how unlikely it is that interprobe correlation will fail to clarify which possible candidates are correct when the potential candidates for two probes are compared. Since polarity discrimination is significant in both the wide pulse and narrow pulse subroutines of the aforementioned copending U.S. patent application Ser. No. 454,124, becomes nearly impossible for potential candidates on a given probe, recognized as such by their waveshapes as commencing with either positive or negative primary pulses, to be cross correlated erroneously. Thus the combination of waveshape recognition and cross correlation provides a nearly foolproof system, even when the discrimination parameters are chosen to provide relatively loose discrimination (a greater chance of recognizing two potential categories).

The present invention is shown as it may be implemented utilizing features described and claimed in other commonly owned, copending U.S. patent applications. However, the invention may be practiced without utilizing such features. For instance: a different type of pulse record data capture may be used; acceleration related thresholds need not be used in a large digital embodiment; the normalizing of engine wear (the wear interval) may be accomplished as described in the aforementioned Couch article; the N extra samples need not be used in the large digital embodiment; statistical correlation may or may not be used, although it is preferable to do so; and system fault detection (FIG. 84) need not be used if not desired. Similarly, different waveform discrimination than that described herein may be utilized in a large digital embodiment, if desired. It should also be understood that the various factors set forth herein are exemplary merely, the various times, voltage values and the like may be altered to suit any given usage to which the present invention may be put. Particularly, the timing between probes will vary in dependence on which probes are utilized. Obviously, if a flameholder in an afterburning engine is used in place of the hoop described hereinbefore, the timing, or numbers of samples, between the second and third probes would be significantly less than as described herein.

The invention herein is shown as including a number of features which are not essential to the practice of of the present invention. Some of these features are disclosed and claimed in other, commonly owned, copending U.S. patent applications, and some of the features are not. As an example, a normal wear interval is disclosed herein as being related to the integral of R.M.S. noise as disclosed in a commonly owned, copending U.S. patent application entitled "Normalizing Engine Wear Indication With R.M.S. Noise", Ser. No. 453,966 filed contemporaneously herewith by Rosenbush and Couch; if desired, the wear integral may be established as a function of D.C. ion current in the exhaust and the time derivative of the square of engine fan speed as described in the aforementioned Couch article. The invention discloses use of a variable threshold of the type described and claimed in a commonly owned, copending U.S. patent application entitled "Electrostatic Engine Diagnostics With Acceleration Related Threshold", Ser. No. 453,962, filed contemporaneously herewith by Rosenbush and Couch; on the other hand, a fixed threshold, determined on a test-by-test, engine-by-engine, or other basis, or a variable threshold dependent upon current R.M.S. noise level, as described in the aforementioned U.S. Pat. No. 3,775,763, may be utilized if desired in conjunction with the present invention. The embodiment herein includes the "M+N" groups of records disclosed and claimed in a commonly owned, copending U.S. patent application entitled "Expanded Classification Sample In Electrostatic Engine Diagnostics", Ser. No. 453,967 filed contemporaneously herewith by Couch as an analysis set. Other sets of before "warning" and after "warning" quantities of records can be used to practice this invention.

The invention is disclosed herein as utilizing a variety of probes disposed at a variety of points in the gas stream of a gas turbine engine. The invention may be practiced using a rod probe of the type described and claimed in a commonly owned, copending U.S. patent application entitled "Gas Turbine Access, Port Plug Electrostatic Probe", Ser. No. 454,113 filed contemporaneously herewith by Shattuck et al; but other rod type probes may be utilized if desired. The exhaust probe disclosed herein is of the type disclosed and claimed in a commonly owned, copending U.S. patent application entitled "Noncontact Electrostatic Hoop Probe For Combustion Engines", Ser. No. 432,507, filed Oct. 4, 1982 by Couch; however, the invention may be practiced utilizing other probes disclosed in said Couch application, or either the grid or the ring or both described in the aforementioned Couch article. The invention may be utilized with still other types of probes, such as that disclosed in a commonly owned, copending U.S. patent application entitled "Afterburner Flameholder Ion Probe", Ser. No. 454,116, filed contemporaneously herewith by Couch.

The invention may be practiced utilizing a variable probes, in dependence upon the particular use to which the invention is to be put. The invention is described as it may be implemented in ground test equipment, employing a free standing hoop probe disposed aft of the engine, but it is readily implemented in a manner suitable for airborne use, to monitor the engine (with or without additional engine-responsive apparatus and/or functions) while the aircraft is in flight.

Similarly, although the invention has been shown and described with respect to exemplary embodiments thereof, it should be understood by those skilled in the art that the foregoing and various other changes, additions and omissions may be made therein and thereto, without departing from the spirit and the scope of the invention.

We claim:

1. Electrostatic diagnostic apparatus for distinctly recognizing different events occuring in an operating gas turbine engine, comprising:

a plurality of electrostatic signal means, each including a probe to be disposed in the gas stream of an engine, for providing, when said probe is disposed in the gas stream of an operating engine, a probe signal having amplitude variations indicative of the magnitude and polarity of electrostatic charge flowing in the gas stream in the vicinity of said probe, said probes being spaced apart from one another along the gas stream of said engine, whereby the gas stream of the engine flows past said probes sequentially;

signal processing means connected for response to each of said electrostatic signal means, for selectively providing a particular engine event identifying signal selected from among a plurality thereof in response to said amplitude variations of more than one of said probe signals having characteristics correlated to an engine event corresponding to said selected identifying signal.

2. Electrostatic diagnostic apparatus according to claim 1 wherein said signal processing means provides said particular engine event identifying signal in dependence on said probe signals having a magnitude in excess of a threshold magnitude and a particular polarity relationship.

3. Electrostatic diagnostic apparatus for distinctly recognizing different events occurring in an operating gas turbine engine, comprising:

a plurality of electrostatic signal means, each including a probe adapted to be disposed in the gas stream of an engine, for providing, when said probe is disposed in the gas stream of an operating engine, a probe signal having a waveshape defined by amplitude variations thereof across a time interval of a given duration in response to electrostatic charge flowing in the gas stream in the vicinity of said probe, said probes being spaced apart from one another along the gas stream of said engine whereby the gas stream of the engine flows past said probes sequentially;

signal processing means connected for response to each of said electrostatic signal means, for selectively providing for each of said probes quality signals indicative of the likelihood of the waveshapes of said probe signals having characteristics correlated to each of a plurality of causal engine events, for combining the quality signals related to each engine event for one probe with the quality signals for each engine event of another probe, and for selectively providing a particular engine event identifying signal in dependence on the combined quality signals.

* * * * *